United States Patent
Chen et al.

(10) Patent No.: US 10,351,622 B2
(45) Date of Patent: *Jul. 16, 2019

(54) PRODUCTION CELL LINE ENHANCERS

(71) Applicant: Regeneron Pharmaceuticals, Inc., Tarrytown, NY (US)

(72) Inventors: Gang Chen, Yorktown Heights, NY (US); Darya Burakov, Yonkers, NY (US); Dipali Deshpande, White Plains, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 165 days.

This patent is subject to a terminal disclaimer.

(21) Appl. No.: 15/624,982

(22) Filed: Jun. 16, 2017

(65) Prior Publication Data

US 2017/0291938 A1    Oct. 12, 2017

Related U.S. Application Data

(60) Continuation of application No. 15/201,104, filed on Jul. 1, 2016, now Pat. No. 9,688,751, which is a division of application No. 14/555,220, filed on Nov. 26, 2014, now Pat. No. 9,382,315, which is a continuation-in-part of application No. PCT/US2013/043116, filed on May 29, 2013, and a division of application No. 13/904,587, filed on May 29, 2013, now Pat. No. 9,079,954, said application No. PCT/US2013/043116 is a continuation of application No. 13/904,587, filed on May 29, 2013, now Pat. No. 9,079,954, application No. 15/624,982, which is a continuation of application No. 14/737,090, filed on Jun. 11, 2015, which is a continuation of application No. 13/904,587, filed on May 29, 2013, now Pat. No. 9,079,954.

(60) Provisional application No. 61/652,549, filed on May 29, 2012.

(51) Int. Cl.
| | |
|---|---|
| C07K 16/22 | (2006.01) |
| C12N 15/85 | (2006.01) |
| C07K 14/47 | (2006.01) |
| C12N 15/79 | (2006.01) |
| C07K 16/00 | (2006.01) |
| C12N 9/24 | (2006.01) |
| C12N 15/09 | (2006.01) |
| C12N 15/63 | (2006.01) |

(52) U.S. Cl.
CPC ............ *C07K 16/22* (2013.01); *C07K 14/47* (2013.01); *C07K 14/4705* (2013.01); *C07K 16/00* (2013.01); *C12N 9/2488* (2013.01); *C12N 15/09* (2013.01); *C12N 15/79* (2013.01); *C12N 15/85* (2013.01); *C12Y 302/01* (2013.01); *C07K 2317/14* (2013.01); *C07K 2317/51* (2013.01); *C07K 2317/515* (2013.01); *C12N 15/63* (2013.01); *C12N 2015/8518* (2013.01)

(58) Field of Classification Search
None
See application file for complete search history.

(56) References Cited

U.S. PATENT DOCUMENTS

| | | | |
|---|---|---|---|
| 7,479,379 B2 * | 1/2009 | Rycyzyn | C07K 14/47 435/69.1 |
| 7,514,237 B2 | 4/2009 | Gao et al. | |
| 9,079,954 B2 | 7/2015 | Chen et al. | |
| 9,193,786 B2 | 11/2015 | Chen et al. | |
| 9,228,012 B2 | 1/2016 | Chen et al. | |
| 9,476,081 B2 | 10/2016 | Cain et al. | |
| 9,950,047 B2 | 4/2018 | Bae et al. | |
| 2004/0170622 A1 | 9/2004 | Glimcher et al. | |
| 2005/0106222 A1 | 5/2005 | Ailor et al. | |
| 2010/0144013 A1 | 6/2010 | Goedegebuur et al. | |
| 2011/0027286 A1 | 2/2011 | Thurston et al. | |
| 2011/0142799 A1 | 6/2011 | Glimcher et al. | |
| 2011/0159015 A1 | 6/2011 | Sleeman et al. | |

(Continued)

FOREIGN PATENT DOCUMENTS

| | | |
|---|---|---|
| CN | 101426812 A | 5/2009 |
| JP | 2007-537728 A | 12/2007 |

(Continued)

OTHER PUBLICATIONS

Slominska-Wojewodzka M, The role of EDEM2 compared with EDEM1 in ricin transport from the endoplasmic reticulum to the cytosol, NCBI GenBank Accession ID:NM_145537.2, Feb. 15, 2015.
Cain K. et al., "A CHO Cell Line Engineered to Express XBP1 and ERO1—Lα Has Increased Levels of Transient Protein Expression", Biotechnol. Prog. 29(3):697-706 (May-Jun. 2013).
Byun et al., Biochem. Biophys. Res. Comm. Jul. 1, 2005; 332(2): 518-23.

(Continued)

*Primary Examiner* — Suzanne M Noakes
*Assistant Examiner* — Jae W Lee
(74) *Attorney, Agent, or Firm* — Scully, Scott, Murphy & Presser, P.C.; Kristan Lansbery

(57) ABSTRACT

The present invention relates to discovery of the ectopic expression of EDEM2 in a production cell to improve the yield of a useful multi-subunit protein. Thus, the present invention provides for production cell lines, such as the canonical mammalian biopharmaceutical production cell, the CHO cell, containing recombinant polynucleotides encoding EDEM2. Also disclosed is a production cell containing both an EDEM2-encoding polynucleotide as well an XBP1-encoding polynucleotide. Improved titers of antibodies produced by these cell lines are disclosed, as well as the improved cell densities attained by these cells in culture.

35 Claims, 3 Drawing Sheets

Specification includes a Sequence Listing.

(56) References Cited

U.S. PATENT DOCUMENTS

| | | |
|---|---|---|
| 2011/0293630 A1 | 12/2011 | Stitt et al. |
| 2013/0323788 A1 | 12/2013 | Chen et al. |
| 2015/0175688 A1 | 6/2015 | Chen et al. |
| 2015/0299309 A1 | 10/2015 | Chen et al. |
| 2015/0299310 A1 | 10/2015 | Chen et al. |
| 2015/0353634 A1 | 12/2015 | Chen et al. |

FOREIGN PATENT DOCUMENTS

| | | |
|---|---|---|
| JP | 2008-507531 A | 3/2008 |
| JP | 2008-513465 A | 5/2008 |
| JP | 2011-504096 A | 2/2011 |
| JP | 2012-504943 A | 3/2012 |
| WO | 2004/111194 A2 | 12/2004 |
| WO | 2005/094355 A2 | 10/2005 |
| WO | 2006/014678 A2 | 2/2006 |
| WO | 2006/031931 A2 | 3/2006 |
| WO | 2009/058346 A1 | 5/2009 |
| WO | 2009/062789 A1 | 5/2009 |
| WO | 2010/040508 A1 | 4/2010 |
| WO | 2011079257 A2 | 6/2011 |
| WO | 2011150008 A1 | 12/2011 |

OTHER PUBLICATIONS

Eriksson, et al., 2004, "EDEM Contributes to Maintenance of Protein Folding Efficiency and Secretory Capacity", J Biol Chem 279(43): pp. 44600-44605.

Hansen, J. et al., 2003, "A large-scale, gene-driven mutagenesis approach for the functional analysis of the mouse genome", Proc Nail Acad Sci U.S.A. 100(17): 9918-9922.

Mast, SW et al., 2005, "Human EDEM2, a novel homolog of family 47 glycosidases, is involved in ER-associated degradation of glycoproteins", Glycobiology 15(4): 421-436.

Olivari, S. et al., 2005, "A Novel Stress-induced EDEM Variant Regulating Endoplasmic Reticulum-associated Glycoprotein Degradation", JBC 208(4): 2424-2428.

Olivari and Molinari, 2007, "Glycoprotein folding and the role of EDEM1, EDEM2 and EDEM3 in degradation of folding-defective glycoproteins", FEBS Lett. 581: 3658-3664.

Schorpp et al., Nucleic Acids Research, 1996, vol. 24, No. 9, pp. 1787-1788.

Strausberg, RL, et al., 2002, "Generation and initial analysis of more than 15,000 full-length human and mouse cDNA sequences", Proc Nail Acad Sci U.S.A. 99(26): 16899-903. Epub Dec. 1, 2002.

Vembar, S.S. and Brodsky, J.L. 2008, "One step at a time: endoplasmic reticulum-associated degradation", Nature Rev Mol Cell Bio 9(12): 944-957. Published online Nov. 12, 2008.

Yoshida, H., et al., 2003, "A time-dependent phase shift in the mammalian unfolded protein response", Dev Cell. 4(2): 265-271.

Yoshida, H. et al., 2006, "XBP1 is critical to protect cells from endoplasmic reticulum stress: evidence from Site-2 protease-deficient Chinese hamster ovary cells", Cell Structure and Function 31(2): 117-125. Epub Nov. 17, 2006.

Ma, Y. and Hendershot, L.M. 2003, "The stressful road to antibody secretion." Nature 4(4):310-311.

Canadian Office Action dated Jun. 29, 2018 received in Canadian Patent Application No. 2,873,131.

Becker E. et al., "Evaluation of a Combinatorial Cell Engineering Approach to Overcome Apoptotic Effects in XBP-1(s) Expressing Cells", Journal of Biotechnology, doi:10.1016/j.jbiotec.2009.11.018 (2008).

Becker E. et al., "A XBP-1 Dependent Bottle-Neck in Production of IgG Subtype Antibodies in Chemically Defined Serum-Free Chinese Hamster Ovary (CHO) Fed-Batch Processes", Journal of Biotechnology, doi:10.1016/j.biotec.2008.03.008 (2007).

Gulis G. et al., "Optimization of Heterologous Protein Production in Chinese Hamster Ovary Cells Under Overexpression of Spliced Form of Human X-Box Binding Protein", BMC Biotechnology 14:26 (2014).

Japanese Notice of Reasons for Rejection dated Mar. 20, 2019 received in Japanese Patent Application No. 2018-030324, together with an English-language translation.

\* cited by examiner

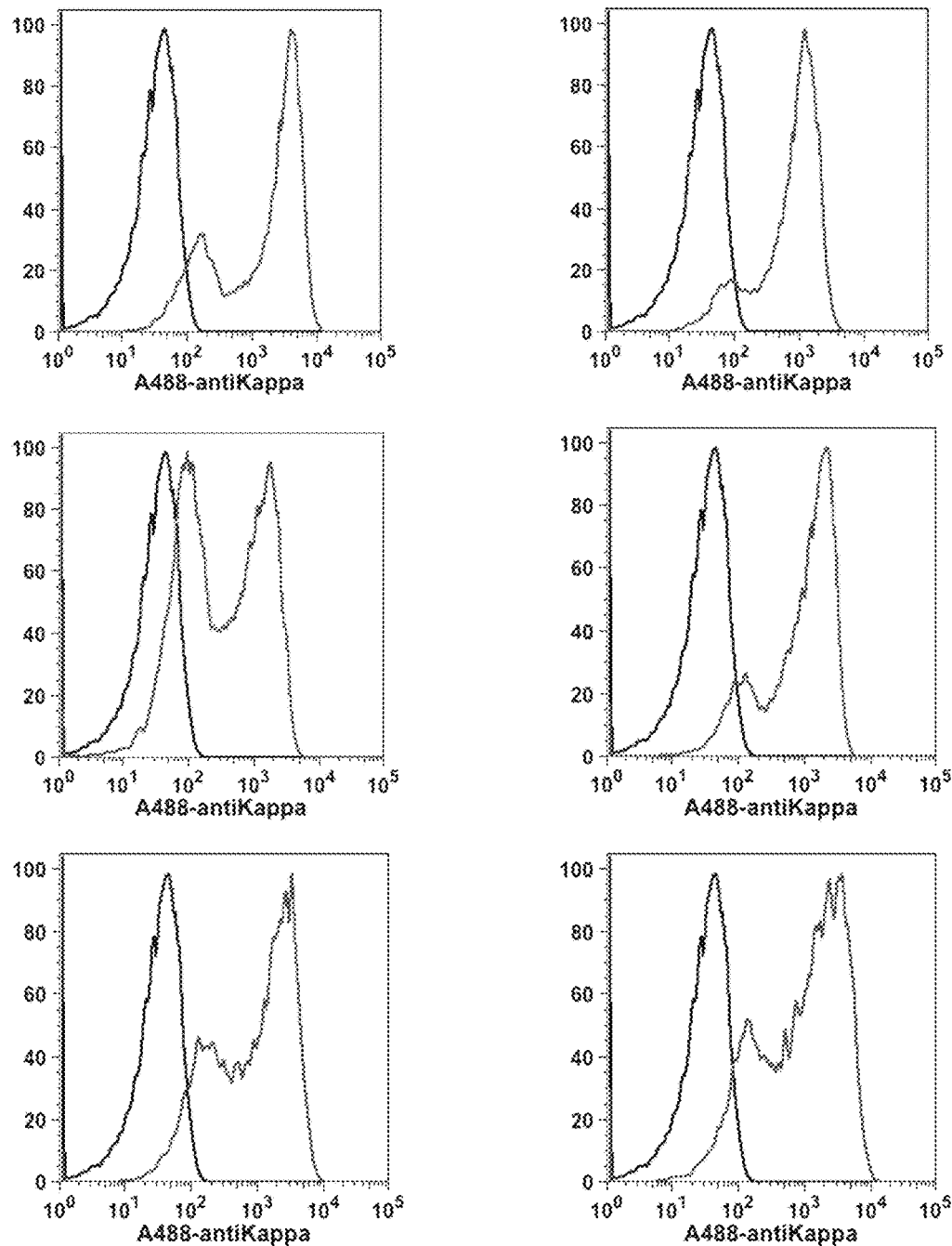
Fig. 2A Clone stability of XBP1-expressing cells

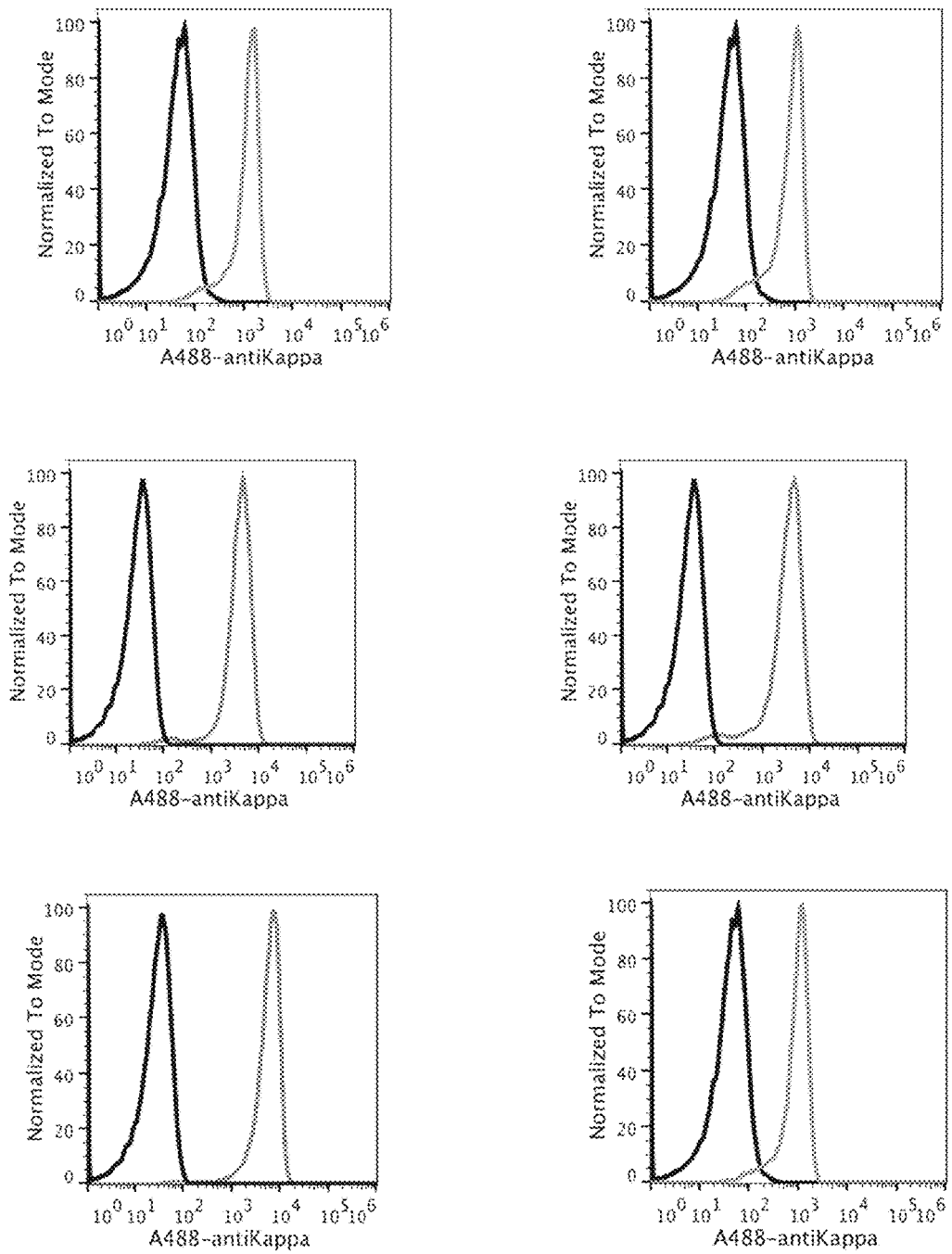
Fig. 2B Clone stability of EDEM2-expressing cells

SEQUENCE LISTING

<160> NUMBER OF SEQ ID NOS: 46

<210> SEQ ID NO 1
<211> LENGTH: 577
<212> TYPE: PRT
<213> ORGANISM: Mus musculus

<400> SEQUENCE: 1

```
Met Pro Phe Arg Leu Leu Ile Pro Leu Gly Leu Val Cys Val Leu Leu
1               5                   10                  15

Pro Leu His His Gly Ala Pro Gly Pro Asp Gly Thr Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Tyr Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Thr Ser Glu Phe Gln Arg
                85                  90                  95

Val Val Glu Val Leu Gln Asp Asn Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270
```

Asp Lys Lys Leu Met Ala Met Phe Leu Glu Tyr Asn Lys Ala Ile Arg
            275                 280                 285

Asn Tyr Thr His Phe Asp Asp Trp Tyr Leu Trp Val Gln Met Tyr Lys
        290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe His Pro Asn Asn Phe Ile His
        435                 440                 445

Asn Asn Gly Ser Thr Phe Asp Ser Val Met Thr Pro His Gly Glu Cys
        450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Arg Arg Leu Lys Glu Glu Gln Trp
                485                 490                 495

Glu Val Glu Asp Leu Ile Lys Glu Phe Tyr Ser Leu Lys Gln Ser Arg
            500                 505                 510

Pro Lys Arg Ala Gln Arg Lys Thr Val Arg Ser Gly Pro Trp Glu Pro
        515                 520                 525

Gln Ser Gly Pro Ala Thr Leu Ser Ser Pro Ala Asn Gln Pro Arg Glu
530                 535                 540

Lys Gln Pro Ala Gln Gln Arg Thr Pro Leu Leu Ser Cys Pro Ser Gln
545                 550                 555                 560

Pro Phe Thr Ser Lys Leu Ala Leu Leu Gly Gln Val Phe Leu Asp Ser
                565                 570                 575

Ser

<210> SEQ ID NO 2
<211> LENGTH: 576
<212> TYPE: PRT
<213> ORGANISM: Rattus norvegicus

<400> SEQUENCE: 2

Met Pro Phe Arg Leu Leu Ile Pro Leu Gly Leu Val Cys Val Leu Leu
1               5                   10                  15

Pro Leu His His Gly Ala Pro Gly Pro Glu Gly Thr Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Tyr Asp Glu Leu Arg Pro Leu Thr
    50                  55                  60

-continued

```
Cys Asp Gly His Asp Thr Trp Gly Ser Phe Ser Leu Thr Leu Ile Asp
 65                  70                  75                  80

Ala Leu Asp Thr Leu Leu Ile Leu Gly Asn Thr Ser Glu Phe Gln Arg
                 85                  90                  95

Val Val Glu Val Leu Gln Asp Asn Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
        275                 280                 285

Asn Tyr Thr His Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe His Pro Asn Asn Phe Ile His
        435                 440                 445

Asn Asn Gly Ser Thr Phe Asp Ser Val Met Thr Pro His Gly Glu Cys
    450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Arg Arg Leu Lys Glu Glu Gln Trp
```

```
                    485                 490                 495
Glu Val Glu Asp Leu Ile Lys Glu Phe Tyr Ser Leu Arg Gln Ser Arg
                500                 505                 510

Ser Arg Ala Gln Arg Lys Thr Val Ser Ser Gly Pro Trp Glu Pro Pro
            515                 520                 525

Ala Gly Pro Gly Thr Leu Ser Ser Pro Glu Asn Gln Pro Arg Glu Lys
        530                 535                 540

Gln Pro Ala Arg Gln Arg Ala Pro Leu Leu Ser Cys Pro Ser Gln Pro
545                 550                 555                 560

Phe Thr Ser Lys Leu Ala Leu Leu Gly Gln Val Phe Leu Asp Ser Ser
                565                 570                 575

<210> SEQ ID NO 3
<211> LENGTH: 578
<212> TYPE: PRT
<213> ORGANISM: Cricetulus griseus

<400> SEQUENCE: 3

Met Pro Phe Arg Leu Leu Ile Pro Leu Gly Leu Val Cys Val Phe Leu
1               5                   10                  15

Pro Leu His His Gly Ala Pro Gly Pro Asp Gly Thr Ala Pro Asp Pro
            20                  25                  30

Ala His Tyr Arg Glu Arg Val Lys Ala Met Phe His Ala Tyr Asp
        35                  40                  45

Ser Tyr Leu Glu Asn Ala Phe Pro Tyr Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Thr Ser Glu Phe Gln Arg
                85                  90                  95

Val Val Glu Val Leu Gln Asp Asn Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Leu Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Arg Ala Ile Arg
        275                 280                 285
```

```
Asn Tyr Thr His Phe Asp Asp Trp Tyr Leu Trp Val Gln Met Tyr Lys
    290                 295                 300
Gly Thr Val Ser Met Pro Val Phe Gln Ser Leu Glu Ala Tyr Trp Pro
305                 310                 315                 320
Gly Leu Gln Ser Leu Ile Gly Asp Ile Asp Asn Ala Met Arg Thr Phe
                325                 330                 335
Leu Asn Tyr Tyr Thr Val Trp Lys Gln Phe Gly Gly Leu Pro Glu Phe
            340                 345                 350
Tyr Asn Ile Ala Gln Gly Tyr Thr Val Glu Lys Arg Glu Gly Tyr Pro
        355                 360                 365
Leu Arg Pro Glu Leu Ile Glu Ser Ala Met Tyr Leu Tyr Arg Ala Thr
    370                 375                 380
Gly Asp Pro Thr Leu Leu Glu Leu Gly Arg Asp Ala Val Glu Ser Ile
385                 390                 395                 400
Glu Lys Ile Ser Lys Val Glu Cys Gly Phe Ala Thr Ile Lys Asp Leu
                405                 410                 415
Arg Asp His Lys Leu Asp Asn Arg Met Glu Ser Phe Phe Leu Ala Glu
            420                 425                 430
Thr Val Lys Tyr Leu Tyr Leu Leu Phe His Pro Asn Asn Phe Ile His
        435                 440                 445
Asn Asn Gly Ser Thr Phe Asp Ser Val Met Thr Pro His Gly Glu Cys
450                 455                 460
Ile Leu Gly Ala Gly Gly Tyr Ile Phe Asn Thr Glu Ala His Pro Ile
465                 470                 475                 480
Asp Pro Ala Ala Leu His Cys Cys Arg Arg Leu Lys Glu Glu Gln Trp
                485                 490                 495
Glu Val Glu Asp Leu Met Arg Glu Leu His Ser Leu Lys Gln Ser Arg
            500                 505                 510
Ser Arg Ala Gln Arg Lys Thr Thr Ser Ser Gly Pro Trp Glu Pro Pro
        515                 520                 525
Ala Gly Pro Gly Ser Pro Ser Ala Pro Gly Lys Gln Asp Gln Pro Arg
    530                 535                 540
Glu Lys Gln Pro Ala Lys Gln Arg Thr Pro Leu Leu Ser Cys Pro Ser
545                 550                 555                 560
Gln Pro Phe Thr Ser Lys Leu Ala Leu Leu Gly Gln Val Phe Leu Asp
                565                 570                 575
Ser Ser

<210> SEQ ID NO 4
<211> LENGTH: 578
<212> TYPE: PRT
<213> ORGANISM: Homo sapiens

<400> SEQUENCE: 4

Met Pro Phe Arg Leu Leu Ile Pro Leu Gly Leu Leu Cys Ala Leu Leu
1               5                   10                  15
Pro Gln His His Gly Ala Pro Gly Pro Asp Gly Ser Ala Pro Asp Pro
                20                  25                  30
Ala His Tyr Arg Glu Arg Val Lys Ala Met Phe Tyr His Ala Tyr Asp
            35                  40                  45
Ser Tyr Leu Glu Asn Ala Phe Pro Phe Asp Glu Leu Arg Pro Leu Thr
        50                  55                  60
Cys Asp Gly His Asp Thr Trp Gly Ser Phe Ser Leu Thr Leu Ile Asp
65                  70                  75                  80
```

-continued

```
Ala Leu Asp Thr Leu Leu Ile Leu Gly Asn Val Ser Glu Phe Gln Arg
                 85                  90                  95

Val Val Glu Val Leu Gln Asp Ser Val Asp Phe Asp Ile Asp Val Asn
            100                 105                 110

Ala Ser Val Phe Glu Thr Asn Ile Arg Val Val Gly Gly Leu Leu Ser
            115                 120                 125

Ala His Leu Leu Ser Lys Lys Ala Gly Val Glu Val Glu Ala Gly Trp
        130                 135                 140

Pro Cys Ser Gly Pro Leu Leu Arg Met Ala Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
            195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
        275                 280                 285

Asn Tyr Thr Arg Phe Asp Asp Trp Tyr Leu Trp Val Gln Met Tyr Lys
    290                 295                 300

Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
        355                 360                 365

Leu Arg Pro Glu Leu Ile Glu Ser Ala Met Tyr Leu Tyr Arg Ala Thr
    370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
            420                 425                 430

Thr Val Lys Tyr Leu Tyr Leu Leu Phe Asp Pro Thr Asn Phe Ile His
        435                 440                 445

Asn Asn Gly Ser Thr Phe Asp Thr Val Ile Thr Pro Tyr Gly Glu Cys
    450                 455                 460

Ile Leu Gly Ala Gly Gly Tyr Ile Phe Asn Thr Glu Ala His Pro Ile
465                 470                 475                 480

Asp Pro Ala Ala Leu His Cys Cys Gln Arg Leu Lys Glu Glu Gln Trp
                485                 490                 495

Glu Val Glu Asp Leu Met Arg Glu Phe Tyr Ser Leu Lys Arg Ser Arg
```

```
                   500                 505                 510
Ser Lys Phe Gln Lys Asn Thr Val Ser Ser Gly Pro Trp Glu Pro Pro
            515                 520                 525

Ala Arg Pro Gly Thr Leu Phe Ser Pro Glu Asn His Asp Gln Ala Arg
    530                 535                 540

Glu Arg Lys Pro Ala Lys Gln Lys Val Pro Leu Leu Ser Cys Pro Ser
545                 550                 555                 560

Gln Pro Phe Thr Ser Lys Leu Ala Leu Leu Gly Gln Val Phe Leu Asp
                565                 570                 575

Ser Ser

<210> SEQ ID NO 5
<211> LENGTH: 578
<212> TYPE: PRT
<213> ORGANISM: Pan troglodytes

<400> SEQUENCE: 5

Met Pro Phe Arg Leu Leu Ile Pro Leu Gly Leu Leu Cys Ala Leu Leu
1               5                   10                  15

Pro Leu His His Gly Ala Pro Gly Pro Asp Gly Ser Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Phe Asp Glu Leu Arg Pro Leu Thr
    50                  55                  60

Cys Asp Gly His Asp Thr Trp Gly Ser Phe Ser Leu Thr Leu Ile Asp
65                  70                  75                  80

Ala Leu Asp Thr Leu Leu Ile Leu Gly Asn Val Ser Glu Phe Gln Arg
                85                  90                  95

Val Val Glu Val Leu Gln Asp Ser Val Asp Phe Asp Ile Asp Val Asn
            100                 105                 110

Ala Ser Val Phe Glu Thr Asn Ile Arg Val Val Gly Gly Leu Leu Ser
        115                 120                 125

Ala His Leu Leu Ser Lys Lys Ala Gly Val Glu Val Glu Ala Gly Trp
    130                 135                 140

Pro Cys Ser Gly Pro Leu Leu Arg Met Ala Glu Glu Ala Ala Arg Lys
145                 150                 155                 160

Leu Leu Pro Ala Phe Gln Thr Pro Thr Gly Met Pro Tyr Gly Thr Val
                165                 170                 175

Asn Leu Leu His Gly Val Asn Pro Gly Glu Thr Pro Val Thr Cys Thr
            180                 185                 190

Ala Gly Ile Gly Thr Phe Ile Val Glu Phe Ala Thr Leu Ser Ser Leu
        195                 200                 205

Thr Gly Asp Pro Val Phe Glu Asp Val Ala Arg Val Ala Leu Met Arg
    210                 215                 220

Leu Trp Glu Ser Arg Ser Asp Ile Gly Leu Val Gly Asn His Ile Asp
225                 230                 235                 240

Val Leu Thr Gly Lys Trp Val Ala Gln Asp Ala Gly Ile Gly Ala Gly
                245                 250                 255

Val Asp Ser Tyr Phe Glu Tyr Leu Val Lys Gly Ala Ile Leu Leu Gln
            260                 265                 270

Asp Lys Lys Leu Met Ala Met Phe Leu Glu Tyr Asn Lys Ala Ile Arg
        275                 280                 285

Asn Tyr Thr Arg Phe Asp Asp Trp Tyr Leu Trp Val Gln Met Tyr Lys
```

```
            290                 295                 300
Gly Thr Val Ser Met Pro Val Phe Gln Ser Leu Glu Ala Tyr Trp Pro
305                 310                 315                 320

Gly Leu Gln Ser Leu Ile Gly Asp Ile Asp Asn Ala Met Arg Thr Phe
                325                 330                 335

Leu Asn Tyr Tyr Thr Val Trp Lys Gln Phe Gly Gly Leu Pro Glu Phe
            340                 345                 350

Tyr Asn Ile Pro Gln Gly Tyr Thr Val Glu Lys Arg Glu Gly Tyr Pro
                355                 360                 365

Leu Arg Pro Glu Leu Ile Glu Ser Ala Met Tyr Leu Tyr Arg Ala Thr
370                 375                 380

Gly Asp Pro Thr Leu Leu Glu Leu Gly Arg Asp Ala Val Glu Ser Ile
385                 390                 395                 400

Glu Lys Ile Ser Lys Val Glu Cys Gly Phe Ala Thr Ile Lys Asp Leu
                405                 410                 415

Arg Asp His Lys Leu Asp Asn Arg Met Glu Ser Phe Phe Leu Ala Glu
                420                 425                 430

Thr Val Lys Tyr Leu Tyr Leu Leu Phe Asp Pro Thr Asn Phe Ile His
            435                 440                 445

Asn Asn Gly Ser Thr Phe Asp Ala Val Ile Thr Pro Tyr Gly Glu Cys
450                 455                 460

Ile Leu Gly Ala Gly Tyr Ile Phe Asn Thr Glu Ala His Pro Ile
465                 470                 475                 480

Asp Pro Ala Ala Leu His Cys Cys Gln Arg Leu Lys Glu Glu Gln Trp
                485                 490                 495

Glu Val Glu Asp Leu Met Arg Glu Phe Tyr Ser Leu Lys Arg Ser Arg
                500                 505                 510

Ser Lys Phe Gln Lys Lys Thr Val Ser Ser Gly Pro Trp Glu Pro Pro
            515                 520                 525

Ala Arg Pro Gly Thr Leu Phe Ser Pro Glu Asn His Asp Gln Ala Arg
            530                 535                 540

Glu Arg Lys Pro Ala Lys Gln Lys Val Pro Leu Leu Ser Cys Pro Ser
545                 550                 555                 560

Gln Pro Phe Thr Ser Lys Leu Ala Leu Leu Gly Gln Val Phe Leu Asp
                565                 570                 575

Ser Ser

<210> SEQ ID NO 6
<211> LENGTH: 513
<212> TYPE: PRT
<213> ORGANISM: Pongo pygmaeus

<400> SEQUENCE: 6

Met Asn Thr Leu Ser Cys Ser Leu Phe Ser Leu Thr Leu Ile Asp Ala
1               5                   10                  15

Leu Asp Thr Leu Leu Ile Leu Gly Asn Val Ser Glu Phe Gln Arg Val
                20                  25                  30

Val Glu Val Leu Gln Asp Asn Val Asp Phe Asp Ile Asp Val Asn Ala
            35                  40                  45

Ser Val Phe Glu Thr Asn Ile Arg Val Gly Gly Leu Leu Ser Ala
            50                  55                  60

His Leu Leu Ser Lys Lys Ala Gly Val Glu Val Glu Ala Gly Trp Pro
65                  70                  75                  80

Cys Ser Gly Pro Leu Leu Arg Met Ala Glu Glu Ala Ala Arg Lys Leu
```

```
                    85                  90                  95
Leu Pro Ala Phe Gln Thr Pro Thr Gly Met Pro Tyr Gly Thr Val Asn
                100                 105                 110
Leu Leu His Gly Val Asn Pro Gly Glu Thr Pro Val Thr Cys Thr Ala
                115                 120                 125
Gly Ile Gly Thr Phe Ile Val Glu Phe Ala Thr Leu Ser Ser Leu Thr
            130                 135                 140
Gly Asp Pro Val Phe Glu Asp Val Ala Arg Val Ala Leu Met Arg Leu
145                 150                 155                 160
Trp Glu Ser Arg Ser Asp Ile Gly Leu Val Gly Asn His Ile Asp Val
                165                 170                 175
Leu Thr Gly Lys Trp Val Ala Gln Asp Ala Gly Ile Gly Ala Gly Val
                180                 185                 190
Asp Ser Tyr Phe Glu Tyr Leu Val Lys Gly Ala Ile Leu Leu Gln Asp
                195                 200                 205
Lys Lys Leu Met Ala Met Phe Leu Glu Tyr Asn Lys Ala Ile Arg Asn
            210                 215                 220
Tyr Thr Arg Phe Asp Asp Trp Tyr Leu Trp Val Gln Met Tyr Lys Gly
225                 230                 235                 240
Thr Val Ser Met Pro Val Phe Gln Ser Leu Glu Ala Tyr Trp Pro Gly
                245                 250                 255
Leu Gln Ser Leu Ile Gly Asp Ile Asp Asn Ala Met Arg Thr Phe Leu
                260                 265                 270
Asn Tyr Tyr Thr Val Trp Lys Gln Phe Gly Gly Leu Pro Glu Phe Tyr
                275                 280                 285
Asn Ile Pro Gln Gly Tyr Thr Val Glu Lys Arg Glu Gly Tyr Pro Leu
            290                 295                 300
Arg Pro Glu Leu Ile Glu Ser Ala Met Tyr Leu Tyr Arg Ala Thr Gly
305                 310                 315                 320
Asp Pro Thr Leu Leu Glu Leu Gly Arg Asp Ala Val Glu Ser Ile Glu
                325                 330                 335
Lys Ile Ser Lys Val Glu Cys Gly Phe Ala Thr Ile Lys Asp Leu Arg
            340                 345                 350
Asp His Lys Leu Asp Asn Arg Met Glu Ser Phe Phe Leu Ala Glu Thr
            355                 360                 365
Val Lys Tyr Leu Tyr Leu Leu Phe Asp Pro Thr Asn Phe Ile His Asn
            370                 375                 380
Asn Gly Ser Thr Phe Asp Ala Val Ile Thr Pro Tyr Gly Glu Cys Ile
385                 390                 395                 400
Leu Gly Ala Gly Gly Tyr Ile Phe Asn Thr Glu Ala His Pro Ile Asp
                405                 410                 415
Pro Ala Ala Leu His Cys Cys Gln Arg Leu Lys Glu Glu Gln Trp Glu
                420                 425                 430
Val Glu Asp Leu Met Arg Glu Phe Tyr Ser Leu Lys Arg Asn Arg Ser
            435                 440                 445
Lys Phe Gln Lys Lys Thr Val Ser Ser Gly Pro Trp Glu Pro Pro Ala
        450                 455                 460
Arg Pro Gly Thr Leu Phe Ser Pro Glu Asn His Asp Gln Ala Arg Gly
465                 470                 475                 480
Arg Lys Pro Ala Lys Gln Lys Val Pro Leu Leu Ser Cys Pro Ser Gln
                485                 490                 495
Pro Phe Thr Ser Lys Leu Ala Leu Leu Gly Gln Val Phe Leu Asp Ser
                500                 505                 510
```

Ser

<210> SEQ ID NO 7
<211> LENGTH: 572
<212> TYPE: PRT
<213> ORGANISM: Danio rerio

<400> SEQUENCE: 7

```
Leu Tyr Tyr Leu Pro Leu Phe Thr Ser Arg Tyr Phe Met Leu Thr Phe
1               5                   10                  15

Leu Phe Ser Ala Ile Phe Cys Ala Ala Tyr Leu Ser Pro Ile Ile Ser
            20                  25                  30

His Val Lys Gly Arg Asp Phe Thr Glu Gln Glu Met Ser His Tyr Arg
        35                  40                  45

Asp Arg Val Lys Ser Met Phe Tyr His Ala Tyr Asn Ser Tyr Leu Asp
    50                  55                  60

Asn Ala Tyr Pro Tyr Asp Glu Leu Arg Pro Leu Thr Cys Asp Gly Gln
65                  70                  75                  80

Asp Thr Trp Gly Ser Phe Ser Leu Thr Leu Ile Asp Ala Leu Asp Thr
                85                  90                  95

Leu Leu Ile Leu Gly Asn His Thr Glu Phe Gln Arg Val Ala Thr Leu
            100                 105                 110

Leu Gln Asp Thr Val Asp Phe Asp Ile Asp Val Asn Ala Ser Val Phe
        115                 120                 125

Glu Thr Asn Ile Arg Val Val Gly Gly Leu Leu Ser Ala His Leu Leu
    130                 135                 140

Ser Lys Arg Ala Gly Met Lys Val Glu Glu Gly Trp Pro Cys Ser Gly
145                 150                 155                 160

Pro Leu Leu Arg Met Ala Glu Asp Ala Ala Arg Lys Leu Leu Pro Ala
                165                 170                 175

Phe Gln Thr Pro Thr Gly Met Pro Tyr Gly Thr Val Asn Leu Leu Arg
            180                 185                 190

Gly Val Asn Pro Gly Glu Thr Pro Val Thr Cys Thr Ala Gly Val Gly
        195                 200                 205

Thr Phe Ile Leu Glu Phe Ser Thr Leu Ser Arg Leu Thr Gly Asp Pro
    210                 215                 220

Val Phe Glu Asn Val Ala Arg Lys Ala Leu Arg Ala Leu Trp Arg Thr
225                 230                 235                 240

Arg Ser Asp Ile Gly Leu Val Gly Asn His Ile Asp Val Ile Thr Ser
                245                 250                 255

Lys Trp Val Ala Gln Asp Ala Gly Ile Gly Ala Gly Val Asp Ser Tyr
            260                 265                 270

Phe Glu Tyr Leu Val Arg Gly Ala Ile Met Leu Gln Asp Glu Glu Leu
        275                 280                 285

Leu Thr Met Phe Tyr Glu Phe Asp Lys Ser Ile Lys Asn Tyr Thr Lys
    290                 295                 300

Phe Asp Asp Trp Tyr Leu Trp Val Gln Met His Lys Gly Thr Val Ser
305                 310                 315                 320

Met Pro Val Phe Gln Ser Leu Glu Ala Phe Trp Pro Gly Met Gln Ser
                325                 330                 335

Leu Ile Gly Asp Ile Ser Ser Ala Thr Lys Ser Phe His Asn Tyr Tyr
            340                 345                 350

Ser Val Trp Arg Gln Phe Gly Gly Leu Pro Glu Phe Tyr Ser Ile Pro
        355                 360                 365
```

```
Gln Gly Tyr Thr Val Asp Lys Arg Glu Gly Tyr Pro Leu Arg Pro Glu
            370                 375                 380

Leu Ile Glu Ser Ala Met Tyr Leu Tyr Lys Ala Thr Gly Asp Pro Ser
385                 390                 395                 400

Phe Ile Gln Leu Gly Arg Asp Ala Val Glu Ser Ile Asp Arg Ile Ser
                405                 410                 415

Arg Val Asn Cys Gly Phe Ala Thr Val Lys Asp Val Arg Asp His Lys
            420                 425                 430

Leu Asp Asn Arg Met Glu Ser Phe Phe Leu Ala Glu Thr Ile Lys Tyr
            435                 440                 445

Leu Tyr Leu Leu Phe Asp Pro Asp Asn Phe Leu His Asn Thr Gly Thr
            450                 455                 460

Glu Phe Glu Leu Gly Gly Leu Arg Gly Asp Cys Ile Leu Ser Ala Gly
465                 470                 475                 480

Gly Tyr Val Phe Asn Thr Glu Ala His Pro Leu Asp Pro Ala Ala Leu
                485                 490                 495

His Cys Cys Ser Arg Glu Gln Gln Asp Arg Arg Glu Ile Gln Asp Ile
            500                 505                 510

Leu Leu Ser Phe Ser Gln Pro His Thr Glu Pro Ser Arg Asp Gln
            515                 520                 525

Ser Ala Gly Gly Ser Pro Glu Ser Ile Ala Leu Lys Pro Gly Glu Gln
530                 535                 540

Arg Lys Ala Pro Val Leu Ser Cys Pro Thr Gln Pro Phe Ser Ala Lys
545                 550                 555                 560

Leu Ala Val Met Gly Gln Val Phe Ser Asp Asn Ser
                565                 570

<210> SEQ ID NO 8
<211> LENGTH: 579
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (12)..(12)
<223> OTHER INFORMATION: V or L
<220> FEATURE:
<221> NAME/KEY: MISC_FEATURE
<222> LOCATION: (14)..(14)
<223> OTHER INFORMATION: V or A
<220> FEATURE:
<221> NAME/KEY: MISC_FEATURE
<222> LOCATION: (15)..(15)
<223> OTHER INFORMATION: L or F
<220> FEATURE:
<221> NAME/KEY: MISC_FEATURE
<222> LOCATION: (26)..(26)
<223> OTHER INFORMATION: D or E
<220> FEATURE:
<221> NAME/KEY: MISC_FEATURE
<222> LOCATION: (28)..(28)
<223> OTHER INFORMATION: T or S
<220> FEATURE:
<221> NAME/KEY: MISC_FEATURE
<222> LOCATION: (57)..(57)
<223> OTHER INFORMATION: Y or F
<220> FEATURE:
<221> NAME/KEY: MISC_FEATURE
<222> LOCATION: (91)..(91)
<223> OTHER INFORMATION: T or V
<220> FEATURE:
<221> NAME/KEY: MISC_FEATURE
<222> LOCATION: (104)..(104)
<223> OTHER INFORMATION: N or S
```

```
<220> FEATURE:
<221> NAME/KEY: MISC_FEATURE
<222> LOCATION: (220)..(220)
<223> OTHER INFORMATION: V or L
<220> FEATURE:
<221> NAME/KEY: MISC_FEATURE
<222> LOCATION: (285)..(285)
<223> OTHER INFORMATION: K or R
<220> FEATURE:
<221> NAME/KEY: MISC_FEATURE
<222> LOCATION: (292)..(292)
<223> OTHER INFORMATION: H or R
<220> FEATURE:
<221> NAME/KEY: MISC_FEATURE
<222> LOCATION: (356)..(356)
<223> OTHER INFORMATION: P or A
<220> FEATURE:
<221> NAME/KEY: MISC_FEATURE
<222> LOCATION: (442)..(442)
<223> OTHER INFORMATION: H or D
<220> FEATURE:
<221> NAME/KEY: MISC_FEATURE
<222> LOCATION: (444)..(444)
<223> OTHER INFORMATION: N or T
<220> FEATURE:
<221> NAME/KEY: MISC_FEATURE
<222> LOCATION: (456)..(456)
<223> OTHER INFORMATION: S, T, or A
<220> FEATURE:
<221> NAME/KEY: MISC_FEATURE
<222> LOCATION: (458)..(458)
<223> OTHER INFORMATION: M or I
<220> FEATURE:
<221> NAME/KEY: MISC_FEATURE
<222> LOCATION: (461)..(461)
<223> OTHER INFORMATION: H or Y
<220> FEATURE:
<221> NAME/KEY: MISC_FEATURE
<222> LOCATION: (489)..(489)
<223> OTHER INFORMATION: R or Q
<220> FEATURE:
<221> NAME/KEY: MISC_FEATURE
<222> LOCATION: (502)..(502)
<223> OTHER INFORMATION: I or M
<220> FEATURE:
<221> NAME/KEY: MISC_FEATURE
<222> LOCATION: (503)..(503)
<223> OTHER INFORMATION: K or R
<220> FEATURE:
<221> NAME/KEY: MISC_FEATURE
<222> LOCATION: (505)..(505)
<223> OTHER INFORMATION: F or L
<220> FEATURE:
<221> NAME/KEY: MISC_FEATURE
<222> LOCATION: (506)..(506)
<223> OTHER INFORMATION: Y or H
<220> FEATURE:
<221> NAME/KEY: MISC_FEATURE
<222> LOCATION: (509)..(509)
<223> OTHER INFORMATION: K or R
<220> FEATURE:
<221> NAME/KEY: MISC_FEATURE
<222> LOCATION: (510)..(510)
<223> OTHER INFORMATION: Q or R
<220> FEATURE:
<221> NAME/KEY: MISC_FEATURE
<222> LOCATION: (513)..(513)
<223> OTHER INFORMATION: P or S
<220> FEATURE:
<221> NAME/KEY: MISC_FEATURE
<222> LOCATION: (514)..(516)
<223> OTHER INFORMATION: KRA, RA, or KF (one amino acid may be missing)
<220> FEATURE:
<221> NAME/KEY: MISC_FEATURE
<222> LOCATION: (518)..(518)
<223> OTHER INFORMATION: R or K
<220> FEATURE:
<221> NAME/KEY: MISC_FEATURE
<222> LOCATION: (519)..(519)
```

```
<223> OTHER INFORMATION: K or N
<220> FEATURE:
<221> NAME/KEY: MISC_FEATURE
<222> LOCATION: (522)..(522)
<223> OTHER INFORMATION: R or S
<220> FEATURE:
<221> NAME/KEY: MISC_FEATURE
<222> LOCATION: (529)..(529)
<223> OTHER INFORMATION: Q or P
<220> FEATURE:
<221> NAME/KEY: MISC_FEATURE
<222> LOCATION: (530)..(530)
<223> OTHER INFORMATION: S or A
<220> FEATURE:
<221> NAME/KEY: MISC_FEATURE
<222> LOCATION: (531)..(531)
<223> OTHER INFORMATION: G or R
<220> FEATURE:
<221> NAME/KEY: MISC_FEATURE
<222> LOCATION: (533)..(533)
<223> OTHER INFORMATION: A or G
<220> FEATURE:
<221> NAME/KEY: MISC_FEATURE
<222> LOCATION: (534)..(534)
<223> OTHER INFORMATION: T or S
<220> FEATURE:
<221> NAME/KEY: MISC_FEATURE
<222> LOCATION: (535)..(535)
<223> OTHER INFORMATION: L or P
<220> FEATURE:
<221> NAME/KEY: MISC_FEATURE
<222> LOCATION: (536)..(536)
<223> OTHER INFORMATION: S or F
<220> FEATURE:
<221> NAME/KEY: MISC_FEATURE
<222> LOCATION: (537)..(537)
<223> OTHER INFORMATION: S or A
<220> FEATURE:
<221> NAME/KEY: MISC_FEATURE
<222> LOCATION: (539)..(542)
<223> OTHER INFORMATION: AN, EN, GKQD, or ENHD (two amino acids may be
      missing)
<220> FEATURE:
<221> NAME/KEY: MISC_FEATURE
<222> LOCATION: (544)..(544)
<223> OTHER INFORMATION: P or A
<220> FEATURE:
<221> NAME/KEY: MISC_FEATURE
<222> LOCATION: (547)..(547)
<223> OTHER INFORMATION: K or R
<220> FEATURE:
<221> NAME/KEY: MISC_FEATURE
<222> LOCATION: (548)..(548)
<223> OTHER INFORMATION: Q or K
<220> FEATURE:
<221> NAME/KEY: MISC_FEATURE
<222> LOCATION: (551)..(551)
<223> OTHER INFORMATION: Q, R, or K
<220> FEATURE:
<221> NAME/KEY: MISC_FEATURE
<222> LOCATION: (553)..(553)
<223> OTHER INFORMATION: R or K
<220> FEATURE:
<221> NAME/KEY: MISC_FEATURE
<222> LOCATION: (554)..(554)
<223> OTHER INFORMATION: T, A, or V

<400> SEQUENCE: 8

Met Pro Phe Arg Leu Leu Ile Pro Leu Gly Leu Xaa Cys Xaa Xaa Leu
1               5                   10                  15

Pro Leu His His Gly Ala Pro Gly Pro Xaa Gly Xaa Ala Pro Asp Pro
            20                  25                  30

Ala His Tyr Arg Glu Arg Val Lys Ala Met Phe Tyr His Ala Tyr Asp
        35                  40                  45

Ser Tyr Leu Glu Asn Ala Phe Pro Xaa Asp Glu Leu Arg Pro Leu Thr
```

```
                50                  55                  60
        Cys Asp Gly His Asp Thr Trp Gly Ser Phe Ser Leu Thr Leu Ile Asp
        65                  70                  75                  80

Ala Leu Asp Thr Leu Leu Ile Leu Gly Asn Xaa Ser Glu Phe Gln Arg
                            85                  90                  95

Val Val Glu Val Leu Gln Asp Xaa Val Asp Phe Asp Ile Asp Val Asn
                        100                 105                 110

Ala Ser Val Phe Glu Thr Asn Ile Arg Val Val Gly Leu Leu Ser
                    115                 120                 125

Ala His Leu Leu Ser Lys Lys Ala Gly Val Glu Val Glu Ala Gly Trp
                130                 135                 140

Pro Cys Ser Gly Pro Leu Leu Arg Met Ala Glu Glu Ala Ala Arg Lys
        145                 150                 155                 160

Leu Leu Pro Ala Phe Gln Thr Pro Thr Gly Met Pro Tyr Gly Thr Val
                        165                 170                 175

Asn Leu Leu His Gly Val Asn Pro Gly Glu Thr Pro Val Thr Cys Thr
                    180                 185                 190

Ala Gly Ile Gly Thr Phe Ile Val Glu Phe Ala Thr Leu Ser Ser Leu
                195                 200                 205

Thr Gly Asp Pro Val Phe Glu Asp Val Ala Arg Xaa Ala Leu Met Arg
            210                 215                 220

Leu Trp Glu Ser Arg Ser Asp Ile Gly Leu Val Gly Asn His Ile Asp
        225                 230                 235                 240

Val Leu Thr Gly Lys Trp Val Ala Gln Asp Ala Gly Ile Gly Ala Gly
                        245                 250                 255

Val Asp Ser Tyr Phe Glu Tyr Leu Val Lys Gly Ala Ile Leu Leu Gln
                    260                 265                 270

Asp Lys Lys Leu Met Ala Met Phe Leu Glu Tyr Asn Xaa Ala Ile Arg
                275                 280                 285

Asn Tyr Thr Xaa Phe Asp Asp Trp Tyr Leu Trp Val Gln Met Tyr Lys
            290                 295                 300

Gly Thr Val Ser Met Pro Val Phe Gln Ser Leu Glu Ala Tyr Trp Pro
        305                 310                 315                 320

Gly Leu Gln Ser Leu Ile Gly Asp Ile Asp Asn Ala Met Arg Thr Phe
                        325                 330                 335

Leu Asn Tyr Tyr Thr Val Trp Lys Gln Phe Gly Gly Leu Pro Glu Phe
                    340                 345                 350

Tyr Asn Ile Xaa Gln Gly Tyr Thr Val Glu Lys Arg Glu Gly Tyr Pro
                355                 360                 365

Leu Arg Pro Glu Leu Ile Glu Ser Ala Met Tyr Leu Tyr Arg Ala Thr
            370                 375                 380

Gly Asp Pro Thr Leu Leu Glu Leu Gly Arg Asp Ala Val Glu Ser Ile
        385                 390                 395                 400

Glu Lys Ile Ser Lys Val Glu Cys Gly Phe Ala Thr Ile Lys Asp Leu
                        405                 410                 415

Arg Asp His Lys Leu Asp Asn Arg Met Glu Ser Phe Phe Leu Ala Glu
                    420                 425                 430

Thr Val Lys Tyr Leu Tyr Leu Leu Phe Xaa Pro Xaa Asn Phe Ile His
                435                 440                 445

Asn Asn Gly Ser Thr Phe Asp Xaa Val Xaa Thr Pro Xaa Gly Glu Cys
            450                 455                 460

Ile Leu Gly Ala Gly Gly Tyr Ile Phe Asn Thr Glu Ala His Pro Ile
        465                 470                 475                 480
```

```
Asp Pro Ala Ala Leu His Cys Cys Xaa Arg Leu Lys Glu Glu Gln Trp
                485                 490                 495

Glu Val Glu Asp Leu Xaa Xaa Glu Xaa Xaa Ser Leu Xaa Xaa Ser Arg
            500                 505                 510

Xaa Xaa Xaa Xaa Gln Xaa Xaa Thr Val Xaa Ser Gly Pro Trp Glu Pro
        515                 520                 525

Xaa Xaa Xaa Pro Xaa Xaa Xaa Xaa Pro Xaa Xaa Xaa Xaa Gln Xaa
    530                 535                 540

Arg Glu Xaa Xaa Pro Ala Xaa Gln Xaa Xaa Pro Leu Leu Ser Cys Pro
545                 550                 555                 560

Ser Gln Pro Phe Thr Ser Lys Leu Ala Leu Leu Gly Gln Val Phe Leu
                565                 570                 575

Asp Ser Ser

<210> SEQ ID NO 9
<211> LENGTH: 371
<212> TYPE: PRT
<213> ORGANISM: Mus musculus

<400> SEQUENCE: 9

Met Val Val Val Ala Ala Ala Pro Ser Ala Ala Thr Ala Ala Pro Lys
1               5                   10                  15

Val Leu Leu Leu Ser Gly Gln Pro Ala Ser Gly Gly Arg Ala Leu Pro
            20                  25                  30

Leu Met Val Pro Gly Pro Arg Ala Ala Gly Ser Glu Ala Ser Gly Thr
        35                  40                  45

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn His Lys Leu Gln Leu Glu Asn Gln Leu Leu
            100                 105                 110

Arg Glu Lys Thr His Gly Leu Val Val Glu Asn Gln Glu Leu Arg Thr
        115                 120                 125

Arg Leu Gly Met Asp Thr Leu Asp Pro Asp Glu Val Pro Glu Val Glu
    130                 135                 140

Ala Lys Gly Ser Gly Val Arg Leu Val Ala Gly Ser Ala Glu Ser Ala
145                 150                 155                 160

Ala Gly Ala Gly Pro Val Val Thr Ser Pro Glu His Leu Pro Met Asp
                165                 170                 175

Ser Asp Thr Val Ala Ser Ser Asp Ser Glu Ser Asp Ile Leu Leu Gly
            180                 185                 190

Ile Leu Asp Lys Leu Asp Pro Val Met Phe Phe Lys Cys Pro Ser Pro
        195                 200                 205

Glu Ser Ala Ser Leu Glu Glu Leu Pro Glu Val Tyr Pro Glu Gly Pro
    210                 215                 220

Ser Ser Leu Pro Ala Ser Leu Ser Leu Ser Val Gly Thr Ser Ser Ala
225                 230                 235                 240

Lys Leu Glu Ala Ile Asn Glu Leu Ile Arg Phe Asp His Val Tyr Thr
                245                 250                 255

Lys Pro Leu Val Leu Glu Ile Pro Ser Glu Thr Glu Ser Gln Thr Asn
            260                 265                 270
```

```
Val Val Val Lys Ile Glu Glu Ala Pro Leu Ser Ser Glu Glu Asp
        275                 280                 285

His Pro Glu Phe Ile Val Ser Val Lys Lys Glu Pro Leu Glu Asp Asp
    290                 295                 300

Phe Ile Pro Glu Leu Gly Ile Ser Asn Leu Leu Ser Ser Ser His Cys
305                 310                 315                 320

Leu Arg Pro Pro Ser Cys Leu Leu Asp Ala His Ser Asp Cys Gly Tyr
                325                 330                 335

Glu Gly Ser Pro Ser Pro Phe Ser Asp Met Ser Ser Pro Leu Gly Thr
                340                 345                 350

Asp His Ser Trp Glu Asp Thr Phe Ala Asn Glu Leu Phe Pro Gln Leu
                355                 360                 365

Ile Ser Val
    370

<210> SEQ ID NO 10
<211> LENGTH: 369
<212> TYPE: PRT
<213> ORGANISM: Cricetulus griseus

<400> SEQUENCE: 10

Met Val Val Val Ala Ala Ser Pro Ser Ala Ala Thr Ala Ala Pro Lys
1               5                   10                  15

Val Leu Leu Leu Ser Gly Gln Pro Ala Ala Asp Gly Arg Ala Leu Pro
                20                  25                  30

Leu Met Val Pro Gly Ser Arg Ala Ala Gly Ser Glu Ala Asn Gly Ala
            35                  40                  45

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn Gln Lys Leu Leu Leu Glu Asn Gln Leu Leu
            100                 105                 110

Arg Glu Lys Thr His Gly Leu Val Ile Glu Asn Gln Glu Leu Arg Thr
        115                 120                 125

Arg Leu Gly Met Asp Val Leu Thr Thr Glu Glu Ala Pro Glu Thr Glu
    130                 135                 140

Ser Lys Gly Asn Gly Val Arg Pro Val Ala Gly Ser Ala Glu Ser Ala
145                 150                 155                 160

Ala Gly Ala Gly Pro Val Val Thr Ser Pro Glu His Leu Pro Met Asp
                165                 170                 175

Ser Asp Thr Val Asp Ser Ser Asp Ser Glu Ser Asp Ile Leu Leu Gly
            180                 185                 190

Ile Leu Asp Lys Leu Asp Pro Val Met Phe Phe Lys Cys Pro Ser Pro
        195                 200                 205

Glu Ser Ala Asn Leu Glu Glu Leu Pro Glu Val Tyr Pro Gly Pro Ser
    210                 215                 220

Ser Leu Pro Ala Ser Leu Ser Leu Ser Val Gly Thr Ser Ser Ala Lys
225                 230                 235                 240

Leu Glu Ala Ile Asn Glu Leu Ile Arg Phe Asp His Val Tyr Thr Lys
                245                 250                 255

Pro Leu Val Leu Glu Ile Pro Ser Glu Thr Glu Ser Gln Thr Asn Val
```

```
                260                 265                 270
Val Val Lys Ile Glu Glu Ala Pro Leu Ser Ser Glu Glu Asp His
            275                 280                 285

Pro Glu Phe Ile Val Ser Val Lys Lys Glu Pro Glu Glu Asp Phe Ile
            290                 295                 300

Pro Glu Pro Gly Ile Ser Asn Leu Leu Ser Ser Ser His Cys Leu Lys
305                 310                 315                 320

Pro Ser Ser Cys Leu Leu Asp Ala Tyr Ser Asp Cys Gly Tyr Glu Gly
                325                 330                 335

Ser Pro Ser Pro Phe Ser Asp Met Ser Ser Pro Leu Gly Ile Asp His
            340                 345                 350

Ser Trp Glu Asp Thr Phe Ala Asn Glu Leu Phe Pro Gln Leu Ile Ser
            355                 360                 365

Val

<210> SEQ ID NO 11
<211> LENGTH: 376
<212> TYPE: PRT
<213> ORGANISM: Homo sapiens

<400> SEQUENCE: 11

Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
                20                  25                  30

Gly Gln Ala Leu Pro Leu Met Val Pro Ala Gln Arg Gly Ala Ser Pro
            35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Asp Ser Glu Ser
            180                 185                 190

Asp Ile Leu Leu Gly Ile Leu Asp Asn Leu Asp Pro Val Met Phe Phe
        195                 200                 205

Lys Cys Pro Ser Pro Glu Pro Ala Ser Leu Glu Glu Leu Pro Glu Val
    210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
```

```
            260                 265                 270
Glu Ser Gln Ala Asn Val Val Lys Ile Glu Glu Ala Pro Leu Ser
        275                 280                 285

Pro Ser Glu Asn Asp His Pro Glu Phe Ile Val Ser Val Lys Glu Glu
        290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
                340                 345                 350

Ser Leu Leu Gly Val Asn His Ser Trp Glu Asp Thr Phe Ala Asn Glu
        355                 360                 365

Leu Phe Pro Gln Leu Ile Ser Val
        370                 375

<210> SEQ ID NO 12
<211> LENGTH: 383
<212> TYPE: PRT
<213> ORGANISM: Danio rerio

<400> SEQUENCE: 12

Met Val Val Val Thr Ala Gly Thr Gly Gly Ala His Lys Val Leu Leu
1               5                   10                  15

Ile Ser Gly Lys Gln Ser Ala Ser Thr Gly Ala Thr Gln Gly Gly Tyr
            20                  25                  30

Ser Arg Ser Ile Ser Val Met Ile Pro Asn Gln Ala Ser Ser Asp Ser
        35                  40                  45

Asp Ser Thr Thr Ser Gly Pro Pro Leu Arg Lys Arg Gln Arg Leu Thr
    50                  55                  60

His Leu Ser Pro Glu Glu Lys Ala Leu Arg Arg Lys Leu Lys Asn Arg
65                  70                  75                  80

Val Ala Ala Gln Thr Ala Arg Asp Arg Lys Lys Ala Lys Met Gly Glu
                85                  90                  95

Leu Glu Gln Gln Val Leu Glu Leu Glu Leu Glu Asn Gln Lys Leu His
            100                 105                 110

Val Glu Asn Arg Leu Leu Arg Asp Lys Thr Ser Asp Leu Leu Ser Glu
        115                 120                 125

Asn Glu Glu Leu Arg Gln Arg Leu Gly Leu Asp Thr Leu Glu Thr Lys
    130                 135                 140

Glu Gln Val Gln Val Leu Glu Ser Ala Val Ser Asp Leu Gly Leu Val
145                 150                 155                 160

Thr Gly Ser Ser Glu Ser Ala Ala Gly Ala Gly Pro Ala Val Pro Lys
                165                 170                 175

Ser Glu Asp Phe Thr Met Asp Thr His Ser Pro Gly Pro Ala Asp Ser
            180                 185                 190

Glu Ser Asp Leu Leu Leu Gly Ile Leu Asp Ile Leu Asp Pro Glu Leu
        195                 200                 205

Phe Leu Lys Thr Asp Leu Pro Glu Ala Gln Glu Pro Gln Gln Glu Leu
    210                 215                 220

Val Leu Val Gly Gly Ala Gly Glu Gln Val Pro Ser Ser Ala Pro Ala
225                 230                 235                 240

Ala Leu Gly Pro Ala Pro Val Lys Leu Glu Ala Leu Asn Glu Leu Ile
                245                 250                 255
```

```
His Phe Asp His Ile Tyr Thr Lys Pro Ala Glu Val Leu Val Ser Glu
            260                 265                 270

Glu Ser Ile Cys Glu Val Lys Ala Glu Asp Ser Val Ala Phe Ser Glu
        275                 280                 285

Thr Glu Glu Glu Ile Gln Val Glu Asp Gln Thr Val Ser Val Lys Asp
    290                 295                 300

Glu Pro Glu Glu Val Val Ile Pro Ala Glu Asn Gln Asn Pro Asp Ala
305                 310                 315                 320

Ala Asp Asp Phe Leu Ser Asp Thr Ser Phe Gly Gly Tyr Glu Lys Ala
                325                 330                 335

Ser Tyr Leu Thr Asp Ala Tyr Ser Asp Ser Gly Tyr Glu Arg Ser Pro
            340                 345                 350

Ser Pro Phe Ser Asn Ile Ser Ser Pro Leu Cys Ser Glu Gly Ser Trp
        355                 360                 365

Asp Asp Met Phe Ala Ser Glu Leu Phe Pro Gln Leu Ile Ser Val
    370                 375                 380

<210> SEQ ID NO 13
<211> LENGTH: 373
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (7)..(7)
<223> OTHER INFORMATION: A or S
<220> FEATURE:
<221> NAME/KEY: MISC_FEATURE
<222> LOCATION: (9)..(9)
<223> OTHER INFORMATION: S or N
<220> FEATURE:
<221> NAME/KEY: MISC_FEATURE
<222> LOCATION: (10)..(10)
<223> OTHER INFORMATION: A or P
<220> FEATURE:
<221> NAME/KEY: MISC_FEATURE
<222> LOCATION: (12)..(12)
<223> OTHER INFORMATION: T or D
<220> FEATURE:
<221> NAME/KEY: MISC_FEATURE
<222> LOCATION: (13)..(13)
<223> OTHER INFORMATION: A or G
<220> FEATURE:
<221> NAME/KEY: MISC_FEATURE
<222> LOCATION: (14)..(14)
<223> OTHER INFORMATION: A or T
<220> FEATURE:
<221> NAME/KEY: MISC_FEATURE
<222> LOCATION: (26)..(26)
<223> OTHER INFORMATION: S or A
<220> FEATURE:
<221> NAME/KEY: MISC_FEATURE
<222> LOCATION: (27)..(27)
<223> OTHER INFORMATION: G, D, or A
<220> FEATURE:
<221> NAME/KEY: MISC_FEATURE
<222> LOCATION: (29)..(29)
<223> OTHER INFORMATION: R or Q
<220> FEATURE:
<221> NAME/KEY: MISC_FEATURE
<222> LOCATION: (37)..(37)
<223> OTHER INFORMATION: G or A
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: MISC_FEATURE
<222> LOCATION: (40)..(40)
<223> OTHER INFORMATION: A or G
```

```
<220> FEATURE:
<221> NAME/KEY: MISC_FEATURE
<222> LOCATION: (46)..(48)
<223> OTHER INFORMATION: S, N, or ASG (two amino acids may be missing)
<220> FEATURE:
<221> NAME/KEY: MISC_FEATURE
<222> LOCATION: (50)..(50)
<223> OTHER INFORMATION: T, A, or L
<220> FEATURE:
<221> NAME/KEY: MISC_FEATURE
<222> LOCATION: (105)..(105)
<223> OTHER INFORMATION: H or Q
<220> FEATURE:
<221> NAME/KEY: MISC_FEATURE
<222> LOCATION: (108)..(108)
<223> OTHER INFORMATION: Q or L
<220> FEATURE:
<221> NAME/KEY: MISC_FEATURE
<222> LOCATION: (123)..(123)
<223> OTHER INFORMATION: V or I
<220> FEATURE:
<221> NAME/KEY: MISC_FEATURE
<222> LOCATION: (130)..(130)
<223> OTHER INFORMATION: T or Q
<220> FEATURE:
<221> NAME/KEY: MISC_FEATURE
<222> LOCATION: (136)..(136)
<223> OTHER INFORMATION: T, V, or A
<220> FEATURE:
<221> NAME/KEY: MISC_FEATURE
<222> LOCATION: (138)..(138)
<223> OTHER INFORMATION: D, T, or V
<220> FEATURE:
<221> NAME/KEY: MISC_FEATURE
<222> LOCATION: (139)..(139)
<223> OTHER INFORMATION: P, T, or A
<220> FEATURE:
<221> NAME/KEY: MISC_FEATURE
<222> LOCATION: (140)..(140)
<223> OTHER INFORMATION: D or E
<220> FEATURE:
<221> NAME/KEY: MISC_FEATURE
<222> LOCATION: (142)..(142)
<223> OTHER INFORMATION: V, A, or none
<220> FEATURE:
<221> NAME/KEY: MISC_FEATURE
<222> LOCATION: (143)..(143)
<223> OTHER INFORMATION: P or none
<220> FEATURE:
<221> NAME/KEY: MISC_FEATURE
<222> LOCATION: (145)..(145)
<223> OTHER INFORMATION: V, T, or A
<220> FEATURE:
<221> NAME/KEY: MISC_FEATURE
<222> LOCATION: (147)..(147)
<223> OTHER INFORMATION: A or S
<220> FEATURE:
<221> NAME/KEY: MISC_FEATURE
<222> LOCATION: (150)..(150)
<223> OTHER INFORMATION: S or N
<220> FEATURE:
<221> NAME/KEY: MISC_FEATURE
<222> LOCATION: (151)..(151)
<223> OTHER INFORMATION: G or E
<220> FEATURE:
<221> NAME/KEY: MISC_FEATURE
<222> LOCATION: (154)..(154)
<223> OTHER INFORMATION: L or P
<220> FEATURE:
<221> NAME/KEY: MISC_FEATURE
<222> LOCATION: (171)..(171)
<223> OTHER INFORMATION: S or P
<220> FEATURE:
<221> NAME/KEY: MISC_FEATURE
<222> LOCATION: (180)..(180)
<223> OTHER INFORMATION: D or G
<220> FEATURE:
<221> NAME/KEY: MISC_FEATURE
<222> LOCATION: (181)..(181)
```

```
<223> OTHER INFORMATION: T or G
<220> FEATURE:
<221> NAME/KEY: MISC_FEATURE
<222> LOCATION: (182)..(182)
<223> OTHER INFORMATION: V or I
<220> FEATURE:
<221> NAME/KEY: MISC_FEATURE
<222> LOCATION: (183)..(183)
<223> OTHER INFORMATION: A or D
<220> FEATURE:
<221> NAME/KEY: MISC_FEATURE
<222> LOCATION: (198)..(198)
<223> OTHER INFORMATION: K or N
<220> FEATURE:
<221> NAME/KEY: MISC_FEATURE
<222> LOCATION: (212)..(212)
<223> OTHER INFORMATION: S or P
<220> FEATURE:
<221> NAME/KEY: MISC_FEATURE
<222> LOCATION: (214)..(214)
<223> OTHER INFORMATION: S or N
<220> FEATURE:
<221> NAME/KEY: MISC_FEATURE
<222> LOCATION: (224)..(224)
<223> OTHER INFORMATION: E or none
<220> FEATURE:
<221> NAME/KEY: MISC_FEATURE
<222> LOCATION: (256)..(256)
<223> OTHER INFORMATION: V or I
<220> FEATURE:
<221> NAME/KEY: MISC_FEATURE
<222> LOCATION: (273)..(273)
<223> OTHER INFORMATION: T or A
<220> FEATURE:
<221> NAME/KEY: MISC_FEATURE
<222> LOCATION: (286)..(286)
<223> OTHER INFORMATION: S or P
<220> FEATURE:
<221> NAME/KEY: MISC_FEATURE
<222> LOCATION: (289)..(289)
<223> OTHER INFORMATION: E or N
<220> FEATURE:
<221> NAME/KEY: MISC_FEATURE
<222> LOCATION: (300)..(300)
<223> OTHER INFORMATION: K or E
<220> FEATURE:
<221> NAME/KEY: MISC_FEATURE
<222> LOCATION: (303)..(303)
<223> OTHER INFORMATION: L, V, or none
<220> FEATURE:
<221> NAME/KEY: MISC_FEATURE
<222> LOCATION: (305)..(305)
<223> OTHER INFORMATION: D or E
<220> FEATURE:
<221> NAME/KEY: MISC_FEATURE
<222> LOCATION: (307)..(307)
<223> OTHER INFORMATION: F or L
<220> FEATURE:
<221> NAME/KEY: MISC_FEATURE
<222> LOCATION: (308)..(308)
<223> OTHER INFORMATION: I or V
<220> FEATURE:
<221> NAME/KEY: MISC_FEATURE
<222> LOCATION: (311)..(311)
<223> OTHER INFORMATION: L or P
<220> FEATURE:
<221> NAME/KEY: MISC_FEATURE
<222> LOCATION: (323)..(323)
<223> OTHER INFORMATION: L or P
<220> FEATURE:
<221> NAME/KEY: MISC_FEATURE
<222> LOCATION: (324)..(324)
<223> OTHER INFORMATION: R or K
<220> FEATURE:
<221> NAME/KEY: MISC_FEATURE
<222> LOCATION: (326)..(326)
<223> OTHER INFORMATION: P or S
<220> FEATURE:
<221> NAME/KEY: MISC_FEATURE
```

```
<222> LOCATION: (333)..(333)
<223> OTHER INFORMATION: H or Y
<220> FEATURE:
<221> NAME/KEY: MISC_FEATURE
<222> LOCATION: (339)..(339)
<223> OTHER INFORMATION: E or G
<220> FEATURE:
<221> NAME/KEY: MISC_FEATURE
<222> LOCATION: (342)..(342)
<223> OTHER INFORMATION: P or L
<220> FEATURE:
<221> NAME/KEY: MISC_FEATURE
<222> LOCATION: (351)..(351)
<223> OTHER INFORMATION: P or L
<220> FEATURE:
<221> NAME/KEY: MISC_FEATURE
<222> LOCATION: (354)..(354)
<223> OTHER INFORMATION: T, I, or V
<220> FEATURE:
<221> NAME/KEY: MISC_FEATURE
<222> LOCATION: (355)..(355)
<223> OTHER INFORMATION: D or N

<400> SEQUENCE: 13

Met Val Val Val Ala Ala Pro Xaa Xaa Ala Xaa Xaa Xaa Pro Lys
1               5                   10                  15

Val Leu Leu Leu Ser Gly Gln Pro Ala Xaa Xaa Gly Xaa Ala Leu Pro
            20                  25                  30

Leu Met Val Pro Xaa Xaa Arg Xaa Ala Gly Ser Glu Ala Xaa Xaa Xaa
        35                  40                  45

Gly Xaa Pro Gln Ala Arg Lys Arg Gln Arg Leu Thr His Leu Ser Pro
    50                  55                  60

Glu Glu Lys Ala Leu Arg Arg Lys Leu Lys Asn Arg Val Ala Ala Gln
65                  70                  75                  80

Thr Ala Arg Asp Arg Lys Lys Ala Arg Met Ser Glu Leu Glu Gln Gln
                85                  90                  95

Val Val Asp Leu Glu Glu Glu Asn Xaa Lys Leu Xaa Leu Glu Asn Gln
            100                 105                 110

Leu Leu Arg Glu Lys Thr His Gly Leu Val Xaa Glu Asn Gln Glu Leu
        115                 120                 125

Arg Xaa Arg Leu Gly Met Asp Xaa Leu Xaa Xaa Xaa Glu Xaa Xaa Glu
    130                 135                 140

Xaa Glu Xaa Lys Gly Xaa Xaa Val Arg Xaa Val Ala Gly Ser Ala Glu
145                 150                 155                 160

Ser Ala Ala Gly Ala Gly Pro Val Val Thr Xaa Pro Glu His Leu Pro
                165                 170                 175

Met Asp Ser Xaa Xaa Xaa Ser Ser Asp Ser Glu Ser Asp Ile Leu
        180                 185                 190

Leu Gly Ile Leu Asp Xaa Leu Asp Pro Val Met Phe Phe Lys Cys Pro
        195                 200                 205

Ser Pro Glu Xaa Ala Xaa Leu Glu Glu Leu Pro Glu Val Tyr Pro Xaa
    210                 215                 220

Gly Pro Ser Ser Leu Pro Ala Ser Leu Ser Leu Ser Val Gly Thr Ser
225                 230                 235                 240

Ser Ala Lys Leu Glu Ala Ile Asn Glu Leu Ile Arg Phe Asp His Xaa
                245                 250                 255

Tyr Thr Lys Pro Leu Val Leu Glu Ile Pro Ser Glu Thr Glu Ser Gln
                260                 265                 270

Xaa Asn Val Val Val Lys Ile Glu Glu Ala Pro Leu Ser Xaa Ser Glu
    275                 280                 285
```

```
Xaa Asp His Pro Glu Phe Ile Val Ser Val Lys Xaa Glu Pro Xaa Glu
    290                 295                 300

Xaa Asp Xaa Xaa Pro Glu Xaa Gly Ile Ser Asn Leu Leu Ser Ser Ser
305             310                 315                 320

His Cys Xaa Xaa Pro Xaa Ser Cys Leu Leu Asp Ala Xaa Ser Asp Cys
            325                 330                 335

Gly Tyr Xaa Gly Ser Xaa Ser Pro Phe Ser Asp Met Ser Ser Xaa Leu
            340                 345                 350

Gly Xaa Xaa His Ser Trp Glu Asp Thr Phe Ala Asn Glu Leu Phe Pro
        355                 360                 365

Gln Leu Ile Ser Val
    370

<210> SEQ ID NO 14
<211> LENGTH: 7686
<212> TYPE: DNA
<213> ORGANISM: Artificial
<220> FEATURE:
<223> OTHER INFORMATION: Synthetic plasmid

<400> SEQUENCE: 14
```

| | | | | | |
|---|---|---|---|---|---|
| aagcttatac | tcgagctcta | gattgggaac | ccgggtctct | cgaattcgat | gcctttttaga | 60 |
| ctcctgatac | cattgggtct | tgtttgcgtt | ctcctccctc | tccatcacgg | cgccccaggt | 120 |
| ccagacggta | ccgcacctga | tcctgcccat | taccgcgaac | gcgttaaagc | catgttctac | 180 |
| cacgcctatg | actcctatct | ggaaaatgca | ttcccctatg | atgagctccg | accccttacc | 240 |
| tgcgatggtc | atgatacttg | gggctctttt | tcccttaccc | ttattgacgc | tctggacaca | 300 |
| ctccttatcc | tcggaaacac | cagcgaattt | caaagagtag | ttgaagtact | tcaggacaat | 360 |
| gtcgactttg | acatcgatgt | gaacgcatca | gttttcgaaa | caaatataag | agtcgttgga | 420 |
| ggtctgctct | ccgcccacct | tctctctaaa | aaagccggag | tagaagttga | agctggctgg | 480 |
| ccctgctccg | accccctcct | tcgtatggct | gaagaagctg | cccgcaaact | ccttcccgct | 540 |
| tttcagaccc | caaccggtat | gccctatggt | actgttaacc | tcctgcacgg | agtaaatccc | 600 |
| ggcgaaaccc | ccgtcacatg | tacagccgga | attggaacct | ttattgtgga | atttgcaacc | 660 |
| cttagcagcc | tgaccggaga | tcctgtattc | gaagacgtgg | ctcgggttgc | cctgatgcga | 720 |
| ctgtgggaat | ccaggtctga | tatcggtctg | gtcggtaacc | atatagacgt | actcactggt | 780 |
| aaatgggttg | cacaagacgc | tggaattggg | gcaggcgtgg | attcttattt | tgaatatctc | 840 |
| gtaaaagggg | ccatactctt | gcaggacaaa | aaacttatgg | ctatgttcct | ggaatataac | 900 |
| aaagctatta | ggaactacac | acacttcgat | gattggtatt | tgtgggtcca | aatgtataaa | 960 |
| ggaaccgttt | ctatgcctgt | ctttcagtca | ctggaggctt | attggcctgg | tctgcaatcc | 1020 |
| ctgatcggag | acattgacaa | tgcaatgagg | acattcctta | attattacac | tgtttggaag | 1080 |
| cagttcggcg | gattgcccga | attttacaac | attcctcaag | gctatacagt | tgaaaaagaa | 1140 |
| gaaggatatc | ccctgcgccc | cgagcttatt | gaaagcgcta | tgtatctgta | tcgtgcaaca | 1200 |
| ggtgatccaa | ccctgcttga | actgggacga | gacgccgtcg | aatcaatcga | gaaaatttca | 1260 |
| aaagtggaat | gcggctttgc | aacaattaaa | gatcttagag | accacaaaac | tggataatcgc | 1320 |
| atggagtcat | tctttttggc | tgagaccgtc | aagtatctgt | atctgctttt | tcatcccaac | 1380 |
| aacttcatcc | ataataacgg | tccaccttg | gattcagtca | tgaccccctca | cggtgaatgc | 1440 |
| atactcggag | ctgaggcta | tatttttaac | actgaagctc | acccaattga | cccagctgcc | 1500 |
| cttcattgtt | gtcgacgtct | gaaagaagaa | caatgggagg | ttgaagattt | gatcaaagaa | 1560 |

```
ttttactcac ttaaacaaag tcgacctaaa cgcgcacaga gaaaaactgt aagatctggt   1620
ccttgggaac ctcagtccgg cccagcaact ctttcatccc ccgccaacca accacgagaa   1680
aaacaaccag cccaacagag aaccccccctg ctcagctgcc cctctcagcc cttcacttca   1740
aaactcgccc tgcttggaca ggtgtttctg gactcctctt gatttaaaca cgcggccgct   1800
aatcagccat accacatttg tagaggtttt acttgcttta aaaaacctcc cacacctccc   1860
cctgaacctg aaacataaaa tgaatgcaat tgttgttgtt aacttgttta ttgcagctta   1920
taatggttac aaataaagca atagcatcac aaatttcaca ataaagcat tttttttcact   1980 gcattctagt tgtggtttgt ccaaactcat caatgtatct tatcatgtct accggtaggg   2040
cccctctctt catgtgagca aaaggccagc aaaaggccag gaaccgtaaa aaggccgcgt   2100
tgctggcgtt tttccatagg ctccgccccc ctgacgagca tcacaaaaat cgacgctcaa   2160
gtcagaggtg gcgaaacccg acaggactat aaagatacca ggcgtttccc cctggaagct   2220
ccctcgtgcg ctctcctgtt ccgacccctgc cgcttaccgg atacctgtcc gcctttctcc   2280
cttcgggaag cgtggcgctt tctcaatgct cacgctgtag gtatctcagt tcggtgtagg   2340
tcgttcgctc caagctgggc tgtgtgcacg aaccccccgt tcagcccgac cgctgcgcct   2400
tatccggtaa ctatcgtctt gagtccaacc cggtaagaca cgacttatcg ccactggcag   2460
cagccactgg taacaggatt agcagagcga ggtatgtagg cggtgctaca gagttcttga   2520
agtggtggcc taactacggc tacactagaa ggacagtatt tggtatctgc gctctgctga   2580
agccagttac cttcggaaaa agagttggta gctcttgatc cggcaaacaa accaccgctg   2640
gtagcggtgg ttttttttgtt tgcaagcagc agattacgcg cagaaaaaaa ggatctcaag   2700
aagatccttt gatcttttct acggggtctg acgctcagtg gaacgaaaac tcacgttaag   2760
ggattttggt catgggcgcg cctcatactc ctgcaggcat gagattatca aaaaggatct   2820
tcacctagat ccttttaaat taaaaatgaa gttttaaatc aatctaaagt atatatgagt   2880
aaacttggtc tgacagttac caatgcttaa tcagtgaggc acctatctca gcgatctgtc   2940
tatttcgttc atccatagtt gcctgactcc ccgtcgtgta gataactacg atacgggagg   3000
gcttaccatc tggccccagt gctgcaatga taccgcgaga cccacgctca ccggctccag   3060
atttatcagc aataaaccag ccagccggaa gggccgagcg cagaagtggt cctgcaactt   3120
tatccgcctc catccagtct attaattgtt gccgggaagc tagagtaagt agttcgccag   3180
ttaatagttt gcgcaacgtt gttgccattg ctacaggcat cgtggtgtca cgctcgtcgt   3240
ttggtatggc ttcattcagc tccggttccc aacgatcaag gcgagttaca tgatccccca   3300
tgttgtgcaa aaaagcggtt agctccttcg gtcctccgat cgttgtcaga agtaagttgg   3360
ccgcagtgtt atcactcatg gttatggcag cactgcataa ttctcttact gtcatgccat   3420
ccgtaagatg cttttctgtg actggtgagt actcaaccaa gtcattctga gaatagtgta   3480
tgcggcgacc gagttgctct tgcccggcgt caatacggga taataccgcg ccacatagca   3540
gaactttaaa agtgctcatc attggaaaac gttcttcggg gcgaaaactc tcaaggatct   3600
taccgctgtt gagatccagt tcgatgtaac ccactcgtgc acccaactga tcttcagcat   3660
cttttacttt caccagcgtt tctgggtgag caaaaacagg aaggcaaaat gccgcaaaaa   3720
agggaataag ggcgacacgg aaatgttgaa tactcatact cttcctttt caatattatt   3780 gaagcattta tcagggttat tgtctcatga gcggatacat atttgaatgt atttagaaaa   3840
ataaacaaat aggggttccg cgcacatttc cccgaaaagt gccacctgac gtcaggtacc   3900
```

```
aagcctaggc ctccaaaaaa gcctcctcac tacttctgga atagctcaga ggcagaggcg    3960
gcctcggcct ctgcataaat aaaaaaaatt agtcagccat ggggcggaga atgggcggaa    4020
ctgggcggag ttaggggcgg gatgggcgga gttaggggcg ggactatggt tgctgactaa    4080
ttgagatgca tgcttttgcat acttctgcct gctggggagc ctgggacttt tccacacctg    4140
gttgctgact aattgagatg catgctttgc atacttctgc ctgctgggga gcctggggac    4200
tttccacacc ggatccacca tgggatcggc cattgaacaa gatggattgc acgcaggttc    4260
tccggccgct tgggtggaga ggctattcgg ctatgactgg gcacaacaga caatcggctg    4320
ctctgatgcc gccgtgttcc ggctgtcagc gcagggcgc ccggttcttt ttgtcaagac    4380
cgacctgtcc ggtgccctga atgaactgca ggacgaggca gcgcggctat cgtggctggc    4440
cacgacgggc gttccttgcg cagctgtgct cgacgttgtc actgaagcgg aagggactg    4500 gctgctattg ggcgaagtgc cggggcagga tctcctgtca tctcaccttg ctcctgccga    4560
gaaagtatcc atcatggctg atgcaatgcg gcggctgcat acgcttgatc cggctacctg    4620
cccattcgac caccaagcga aacatcgcat cgagcgagca cgtactcgga tggaagccgg    4680
tcttgtcgat caggatgatc tggacgaaga gcatcagggg ctcgcgccag ccgaactgtt    4740
cgccaggctc aaggcgcgca tgcccgacgg cgatgatctc gtcgtgaccc atggcgatgc    4800
ctgcttgccg aatatcatgg tggaaaatgg ccgcttttct ggattcatcg actgtggccg    4860
gctgggtgtg gcggaccgct atcaggacat agcgttggct acccgtgata ttgctgaaga    4920
gcttggcggc gaatgggctg accgcttcct cgtgctttac ggtatcgccg ctcccgattc    4980
gcagcgcatc gccttctatc gccttcttga cgagttcttc tgaacgcgtg ctgtaagtct    5040
gcagaaattg atgatctatt aaacaataaa gatgtccact aaaatggaag ttttcctgt    5100 catactttgt taagaagggt gagaacagag tacctacatt ttgaatggaa ggattggagc    5160 tacggggtg ggggtggggt gggattagat aaatgcctgc tctttactga aggctcttta    5220
ctattgcttt atgataatgt ttcatagttg gatatcataa tttaaacaag caaaaccaaa    5280
ttaagggcca gctcattcct cccactcatg atctatggat ctatagatct ctcgtgcagc    5340
tggggctcta gggggtatcc ccacgcgccc tgtagcggcg cattaagcgc ggcgggtgtg    5400
gtggttacgc gcagcgtgac cgctacactt gccagcgccc tagcgcccgc tcctttcgct    5460
ttcttccctt cctttctcgc cacgttcgcc ggctttcccc gtcaagctct aaatcggggg    5520
ctccctttag ggttccgatt tagtgcttta cggcacctcg accccaaaaa acttgattag    5580
ggtgatggtt cacgtagtgg gccatcgccc tgatagacgg ttttcgccc tttgacgttg    5640 gagtccacgt tctttaatag tggactcttg ttccaaactg gaacaacact caaccctatc    5700
tcggtctatt cttttgattt ataagggatt ttgccgattt cggcctattg gttaaaaaat    5760
gagctgattt aacaaaaatt taacgcgaat taattctgtg aatgtgtgt cagttagtcg    5820 cgaggcctcc gcgccgggtt ttggcgcctc ccgcgggcgc ccccctcctc acggcgagcg    5880
ctgccacgtc agacgaaggg cgcagcgagc gtcctgatcc ttccgcccgg acgctcagga    5940
cagcggcccg ctgctcataa gactcggcct tagaacccca gtatcagcag aaggacattt    6000
taggacggga cttgggtgac tctagggcac tggttttctt tccagagagc ggaacaggcg    6060
aggaaaagta gtcccttctc ggcgattctg cggagggatc tccgtggggc ggtgaacgcc    6120
gatgattata taaggacgcg ccgggtgtgg cacagctagt tccgtcgcag ccgggatttg    6180
ggtcgcggtt cttgtttgtg gatcgctgtg atcgtcactt ggtgagtagc gggctgctgg    6240
gctggccggg gctttcgtgg ccgccgggcc gctcggtggg acggaagcgt gtggagagac    6300
```

```
cgccaagggc tgtagtctgg gtccgcgagc aaggttgccc tgaactgggg gttgggggga    6360
gcgcagcaaa atggcggctg ttcccgagtc ttgaatggaa gacgcttgtg aggcgggctg    6420
tgaggtcgtt gaaacaaggt gggggcatg gtgggcggca agaacccaag gtcttgaggc     6480
cttcgctaat gcgggaaagc tcttattcgg gtgagatggg ctggggcacc atctggggac    6540
cctgacgtga agtttgtcac tgactggaga actcggtttg tcgtctgttg cggggcggc     6600
agttatggcg gtgccgttgg gcagtgcacc cgtaccttg ggagcgcgcg ccctcgtcgt     6660
gtcgtgacgt cacccgttct gttggcttat aatgcagggt ggggccacct gccggtaggt    6720
gtgcggtagg cttttctccg tcgcaggacg cagggttcgg gcctagggta ggctctcctg    6780
aatcgacagg cgccggacct ctggtgaggg gagggataag tgaggcgtca gtttctttgg    6840
tcggttttat gtacctatct tcttaagtag ctgaagctcc ggttttgaac tatgcgctcg    6900
gggttggcga gtgtgttttg tgaagttttt taggcacctt ttgaaatgta atcatttggg   6960
tcaatatgta attttcagtg ttagactagt aaattgtccg ctaaattctg gccgttttg    7020
gcttttttgt tagacgtcga ccgatcctga gaacttcagg gtgagtttgg ggacccttga    7080
ttgttctttc ttttcgcta ttgtaaaatt catgttatat ggaggggca aagttttcag     7140
ggtgttgttt agaatgggaa gatgtccctt gtatcaccat ggaccctcat gataattttg    7200
tttctttcac tttctactct gttgacaacc attgtctcct cttattttct tttcattttc    7260
tgtaacttt tcgttaaact ttagcttgca tttgtaacga attttaaat tcactttgt      7320
ttatttgtca gattgtaagt actttctcta atcactttt tttcaaggca atcagggtat    7380
attatattgt acttcagcac agttttagag aacaattgtt ataattaaat gataaggtag   7440
aatatttctg catataaatt ctggctggcg tggaaatatt cttattggta gaaacaacta   7500
caccctggtc atcatcctgc ctttctcttt atggttacaa tgatatacac tgtttgagat   7560
gaggataaaa tactctgagt ccaaaccggg cccctctgct aaccatgttc atgccttctt   7620
ctctttccta cagctcctgg gcaacgtgct ggttgttgtg ctgtctcatc attttggcaa   7680
agaatt                                                              7686
```

<210> SEQ ID NO 15
<211> LENGTH: 7257
<212> TYPE: DNA
<213> ORGANISM: Artificial
<220> FEATURE:
<223> OTHER INFORMATION: Synthetic plasmid

<400> SEQUENCE: 15

```
aagcttatac tcgagctcta gattgggaac ccgggtctct cgaattcgat gccttttaga     60
ctcctgatac cattgggtct tgtttgcgtt ctcctccctc tccatcacgg cgccccaggt    120
ccagacggta ccgcacctga tcctgcccat taccgcgaac gcgttaaagc catgttctac    180
cacgcctatg actcctatct ggaaaatgca ttccccctatg atgagctccg accccttacc   240
tgcgatggtc atgatacttg gggctctttt tcccttaccc ttattgacgc tctggacaca   300
ctccttatcc tcggaaacac cagcgaattt caaagagtag ttgaagtact tcaggacaat   360
gtcgactttg acatcgatgt gaacgcatca gtttttcgaaa caaatataag agtcgttgga   420
ggtctgctct ccgcccacct tctctctaaa aaagccggag tagaagttga agctggctgg   480
ccctgctccg gaccctcct tcgtatggct gaagaagctg cccgcaaact ccttcccgct   540
tttcagaccc caaccggtat gccctatggt actgttaacc tcctgcacgg agtaaatccc   600
```

```
ggcgaaaccc ccgtcacatg tacagccgga attggaacct ttattgtgga atttgcaacc    660
cttagcagcc tgaccggaga tcctgtattc gaagacgtgg ctcgggttgc cctgatgcga    720
ctgtgggaat ccaggtctga tatcggtctg gtcggtaacc atatagacgt actcactggt    780
aaatggggttg cacaagacgc tggaattggg gcaggcgtgg attcttattt tgaatatctc   840
gtaaaagggg ccatactctt gcaggacaaa aaacttatgg ctatgttcct ggaatataac    900
aaagctatta ggaactacac acacttcgat gattggtatt tgtgggtcca aatgtataaa    960
ggaaccgttt ctatgcctgt ctttcagtca ctggaggctt attggcctgg tctgcaatcc   1020
ctgatcggag acattgacaa tgcaatgagg acattcctta attattacac tgtttggaag   1080
cagttcggcg gattgcccga atttacaac attcctcaag gctatacagt tgaaaaaaga    1140
gaaggatatc ccctgcgccc cgagcttatt gaaagcgcta tgtatctgta tcgtgcaaca   1200
ggtgatccaa ccctgcttga actgggacga gacgccgtcg aatcaatcga gaaaatttca   1260
aaagtggaat gcggctttgc aacaattaaa gatcttagag accacaaact ggataatcgc   1320
atggagtcat tcttttttggc tgagaccgtc aagtatctgt atctgctttt tcatcccaac   1380
aacttcatcc ataataacgg gtccaccttc gattcagtca tgacccctca cggtgaatgc   1440
atactcggag ctggaggcta tattttaac actgaagctc acccaattga cccagctgcc   1500
cttcattgtt gtcgacgtct gaaagaagaa caatgggagg ttgaagattt gatcaaagaa   1560
ttttactcac ttaaacaaag tcgacctaaa cgcgcacaga aaaaactgt aagatctggt    1620
ccttgggaac ctcagtccgg cccagcaact ctttcatccc ccgccaacca accacgagaa   1680
aaacaaccag cccaacagag aaccccctg ctcagctgcc cctctcagcc cttcacttca    1740
aaactcgccc tgcttggaca ggtgtttctg gactcctctt gatttaaaca cgcggccgct   1800
aatcagccat accacatttg tagaggtttt acttgcttta aaaaacctcc cacacctccc   1860
cctgaacctg aaacataaaa tgaatgcaat tgttgttgtt aacttgttta ttgcagctta   1920
taatggttac aaataaagca atagcatcac aaatttcaca aataaagcat ttttttcact   1980
gcattctagt tgtggtttgt ccaaactcat caatgtatct tatcatgtct accggtaggg   2040
cccctctctt catgtgagca aaaggccagc aaaaggccag gaaccgtaaa aaggccgcgt   2100
tgctggcgtt tttccatagg ctccgccccc ctgacgagca tcacaaaaat cgacgctcaa   2160
gtcagaggtg gcgaaacccg acaggactat aaagatacca ggcgtttccc cctggaagct   2220
ccctcgtgcg ctctcctgtt ccgaccctgc cgcttaccgg atacctgtcc gcctttctcc   2280
cttcgggaag cgtggcgctt tctcatagct cacgctgtag gtatctcagt tcggtgtagg   2340
tcgttcgctc caagctgggc tgtgtgcacg aaccccccgt tcagcccgac cgctgcgcct   2400
tatccggtaa ctatcgtctt gagtccaacc cggtaagaca cgacttatcg ccactggcag   2460
cagccactgg taacaggatt agcagagcga ggtatgtagg cggtgctaca gagttcttga   2520
agtggtggcc taactacggc tacactagaa ggacagtatt tggtatctgc gctctgctga   2580
agccagttac cttcggaaaa agagttggta gctcttgatc cggcaaacaa accaccgctg   2640
gtagcggtgg tttttttgtt tgcaagcagc agattacgcg cagaaaaaaa ggatctcaag   2700
aagatccttt gatcttttct acggggtctg acgctcagtg gaacgaaaac tcacgttaag   2760
ggattttggt catgggcgcg cctcatactc ctgcaggcat gagattatca aaaaggatct   2820
tcacctagat ccttttaaat taaaaatgaa gttttaaatc aatctaaagt atatatgagt   2880
aaacttggtc tgacagttac caatgcttaa tcagtgaggc acctatctca gcgatctgtc   2940
tatttcgttc atccatagtt gcctgactcc ccgtcgtgta gataactacg atacgggagg   3000
```

```
gcttaccatc tggccccagt gctgcaatga taccgcgaga cccacgctca ccggctccag    3060
atttatcagc aataaaccag ccagccggaa gggccgagcg cagaagtggt cctgcaactt    3120
tatccgcctc catccagtct attaattgtt gccgggaagc tagagtaagt agttcgccag    3180
ttaatagttt gcgcaacgtt gttgccattg ctacaggcat cgtggtgtca cgctcgtcgt    3240
ttggtatggc ttcattcagc tccggttccc aacgatcaag gcgagttaca tgatccccca    3300
tgttgtgcaa aaaagcggtt agctccttcg gtcctccgat cgttgtcaga gtaagttgg     3360 ccgcagtgtt atcactcatg gttatggcag cactgcataa ttctcttact gtcatgccat    3420
ccgtaagatg cttttctgtg actggtgagt actcaaccaa gtcattctga aatagtgta     3480 tgcggcgacc gagttgctct tgcccggcgt caatacggga taataccgcg ccacatagca    3540
gaactttaaa agtgctcatc attggaaaac gttcttcggg gcgaaaactc tcaaggatct    3600
taccgctgtt gagatccagt tcgatgtaac ccactcgtgc acccaactga tcttcagcat    3660
cttttacttt caccagcgtt tctgggtgag caaaaacagg aaggcaaaat gccgcaaaaa    3720
agggaataag ggcgacacgg aaatgttgaa tactcatact cttccttttt caatattatt    3780
gaagcattta tcagggttat tgtctcatga gcggatacat atttgaatgt atttagaaaa    3840
ataaacaaat aggggttccg cgcacatttc cccgaaaagt gccacctgac gtcaggtacc    3900
aagcctaggc ctccaaaaaa gcctcctcac tacttctgga atagctcaga ggcagaggcg    3960
gcctcggcct ctgcataaat aaaaaaaatt agtcagccat ggggcggaga atgggcggaa    4020
ctgggcggag ttaggggcgg gatgggcgga gttaggggcg ggactatggt tgctgactaa    4080
ttgagatgca tgctttgcat acttctgcct gctggggagc ctggggactt ccacacctg     4140 gttgctgact aattgagatg catgctttgc atacttctgc ctgctgggga gcctggggac    4200
tttccacacc ggatccacca tggccaagtt gaccagtgcc gttccggtgc tcaccgcgcg    4260
cgacgtcgcc ggagcggtcg agttctggac cgaccggctc gggttctccc gggacttcgt    4320
ggaggacgac ttcgccggtg tggtccggga cgacgtgacc ctgttcatca gcgcggtcca    4380
ggaccaggtg gtgccggaca cacccctggc ctgggtgtgg gtgcgcggcc tggacgagct    4440
gtacgccgag tggtcggagg tcgtgtccac gaacttccgg gacgcctccg ggccggccat    4500
gaccgagatc ggcgagcagc cgtggggggcg ggagttcgcc ctgcgcgacc cggccggcaa    4560
ctgcgtgcac ttcgtggccg aggagcagga ctgaacgcgt gctgtaagtc tgcagaaatt    4620
gatgatctat taaacaataa agatgtccac taaaatggaa gtttttcctg tcatactttg    4680
ttaagaaggg tgagaacaga gtacctacat tttgaatgga aggattggag ctacgggggt    4740
gggggtgggg tgggattaga taaatgcctg ctctttactg aaggctcttt actattgctt    4800
tatgataatg tttcatagtt ggatatcata atttaaacaa gcaaaccaa attaagggcc     4860 agctcattcc tcccactcat gatctatgga tctatagatc tctcgtgcag ctggggctct    4920 aggggggtatc cccacgcgcc ctgtagcggc gcattaagcg cggcgggtgt ggtggttacg    4980
cgcagcgtga ccgctacact tgccagcgcc ctagcgcccg ctcctttcgc tttcttccct    5040
tcctttctcg ccacgttcgc cggctttccc cgtcaagctc taaatcgggg gctcccttta    5100
gggttccgat ttagtgcttt acggcacctc gaccccaaaa aacttgatta gggtgatggt    5160
tcacgtagtg ggccatcgcc ctgatagacg gttttcgcc ctttgacgtt ggagtccacg     5220
ttctttaata gtggactctt gttccaaact ggaacaacac tcaacccta tctcggtctat    5280 tcttttgatt tataagggat tttgccgatt tcggcctatt ggttaaaaaa tgagctgatt    5340
```

```
taacaaaaat ttaacgcgaa ttaattctgt ggaatgtgtg tcagttagtc gcgaggcctc   5400
cgcgccgggt tttggcgcct cccgcgggcg cccccctcct cacggcgagc gctgccacgt   5460
cagacgaagg gcgcagcgag cgtcctgatc cttccgcccg gacgctcagg acagcggccc   5520
gctgctcata agactcggcc ttagaacccc agtatcagca aaggacattt ttaggacggg   5580
acttgggtga ctctagggca ctggttttct ttccagagag cggaacaggc gaggaaaagt   5640
agtcccttct cggcgattct gcggagggat ctccgtgggg cggtgaacgc cgatgattat   5700
ataaggacgc gccgggtgtg gcacagctag ttccgtcgca gccgggattt gggtcgcggt   5760
tcttgtttgt ggatcgctgt gatcgtcact tggtgagtag cgggctgctg ggctggccgg   5820
ggctttcgtg gccgccgggc cgctcggtgg gacggaagcg tgtggagaga ccgccaaggg   5880
ctgtagtctg ggtccgcgag caaggttgcc ctgaactggg ggttgggggg agcgcagcaa   5940
aatggcggct gttcccgagt cttgaatgga agacgcttgt gaggcgggct gtgaggtcgt   6000
tgaaacaagg tgggggcat ggtgggcggc aagaacccaa ggtcttgagg ccttcgctaa    6060
tgcgggaaag ctcttattcg ggtgagatgg gctggggcac catctgggga ccctgacgtg   6120
aagtttgtca ctgactggag aactcggttt gtcgtctgtt gcggggcgg cagttatggc     6180
ggtgccgttg ggcagtgcac ccgtaccttt gggagcgcgc gccctcgtcg tgtcgtgacg   6240
tcacccgttc tgttggctta taatgcaggg tggggccacc tgccggtagg tgtgcggtag   6300
gcttttctcc gtcgcaggac gcagggttcg ggcctagggt aggctctcct gaatcgacag   6360
gcgccggacc tctggtgagg ggagggataa gtgaggcgtc agtttctttg gtcggtttta   6420
tgtacctatc ttcttaagta gctgaagctc cggttttgaa ctatgcgctc ggggttggcg   6480
agtgtgtttt gtgaagtttt ttaggcacct tttgaaatgt aatcatttgg gtcaatatgt   6540
aattttcagt gttagactag taaattgtcc gctaaattct ggccgttttt ggctttttg    6600
ttagacgtcg accgatcctg agaacttcag ggtgagtttg ggacccttg attgttcttt    6660
cttttcgct attgtaaaat tcatgttata tggaggggc aaagttttca gggtgttgtt     6720
tagaatggga agatgtccct tgtatcacca tggaccctca tgataatttt gtttctttca   6780
cttctactc tgttgacaac cattgtctcc tcttattttc ttttcatttt ctgtaacttt    6840
ttcgttaaac tttagcttgc atttgtaacg aattttaaa ttcacttttg tttatttgtc    6900
agattgtaag tactttctct aatcacttt ttttcaaggc aatcagggta tattatattg    6960
tacttcagca cagttttaga gaacaattgt tataattaaa tgataaggta gaatatttct   7020
gcatataaat tctggctggc gtggaaatat tcttattggt agaaacaact acaccctggt   7080
catcatcctg cctttctctt tatggttaca atgatataca ctgtttgaga tgaggataaa   7140
atactctgag tccaaaccgg gccctctgc taaccatgtt catgccttct tctcttttcct   7200
acagctcctg ggcaacgtgc tggttgttgt gctgtctcat cattttggca aagaatt      7257
```

<210> SEQ ID NO 16
<211> LENGTH: 3892
<212> TYPE: DNA
<213> ORGANISM: Artificial
<220> FEATURE:
<223> OTHER INFORMATION: Synthetic construct

<400> SEQUENCE: 16

```
aggcctccgc gccgggtttt ggcgcctccc gcgggcgccc ccctcctcac ggcgagcgct     60
gccacgtcag acgaagggcg cagcgagcgt cctgatcctt ccgcccggac gctcaggaca    120
gcggcccgct gctcataaga ctcggcctta gaaccccagt atcagcagaa ggacatttta   180
```

```
ggacgggact tgggtgactc tagggcactg gttttctttc cagagagcgg aacaggcgag      240
gaaaagtagt cccttctcgg cgattctgcg gagggatctc cgtggggcgg tgaacgccga      300
tgattatata aggacgcgcc gggtgtggca cagctagttc cgtcgcagcc gggatttggg      360
tcgcggttct tgtttgtgga tcgctgtgat cgtcacttgg tgagtagcgg gctgctgggc      420
tggccggggc tttcgtggcc gccgggccgc tcggtgggac ggaagcgtgt ggagagaccg      480
ccaagggctg tagtctgggt ccgcgagcaa ggttgccctg aactgggggt tgggggagc       540 gcagcaaaat ggcggctgtt cccgagtctt gaatggaaga cgcttgtgag gcgggctgtg      600
aggtcgttga acaaggtgg ggggcatggt gggcggcaag aacccaaggt cttgaggcct       660
tcgctaatgc gggaaagctc ttattcgggt gagatgggct ggggcaccat ctggggaccc      720
tgacgtgaag tttgtcactg actgagaac tcggtttgtc gtctgttgcg ggggcggcag       780
ttatggcggt gccgttgggc agtgcacccg tacctttggg agcgcgcgcc ctcgtcgtgt      840
cgtgacgtca cccgttctgt tggcttataa tgcagggtgg ggccacctgc cggtaggtgt      900
gcggtaggct tttctccgtc gcaggacgca gggttcgggc ctagggtagg ctctcctgaa      960
tcgacaggcg ccggacctct ggtgagggga gggataagtg aggcgtcagt ttctttggtc     1020
ggttttatgt acctatcttc ttaagtagct gaagctccgg ttttgaacta tgcgctcggg     1080
gttggcgagt gtgttttgtg aagttttta ggcacctttt gaaatgtaat catttgggtc      1140
aatatgtaat tttcagtgtt agactagtaa attgtccgct aaattctggc cgttttggc      1200 ttttttgtta gacgtcgacc gatcctgaga acttcagggt gagtttgggg acccttgatt     1260
gttctttctt tttcgctatt gtaaaattca tgttatatgg aggggcaaa gttttcaggg      1320 tgttgtttag aatgggaaga tgtcccttgt atcaccatgg accctcatga aattttgtt      1380 tctttcactt tctactctgt tgacaaccat tgtctcctct tattttcttt tcattttctg     1440
taactttttc gttaaacttt agcttgcatt tgtaacgaat ttttaaattc acttttgttt     1500
atttgtcaga ttgtaagtac tttctctaat cacttttttt tcaaggcaat cagggtatat     1560
tatattgtac ttcagcacag ttttagagaa caattgttat aattaaatga taggtagaa      1620 tatttctgca tataaattct ggctggcgtg gaaatattct tattggtaga aacaactaca     1680
ccctggtcat catcctgcct ttctctttat ggttacaatg atatacactg tttgagatga     1740
ggataaaata ctctgagtcc aaaccgggcc cctctgctaa ccatgttcat gccttcttct     1800
ctttcctaca gctcctgggc aacgtgctgg ttgttgtgct gtctcatcat tttggcaaag     1860
aattaagctt atactcgagc tctagattgg gaacccgggt ctctcgaatt cgatgccttt     1920
tagactcctg ataccattgg gtcttgtttg cgttctcctc cctctccatc acggcgcccc     1980
aggtccagac ggtaccgcac ctgatcctgc ccattaccgc gaacgcgtta aagccatgtt     2040
ctaccacgcc tatgactcct atctggaaaa tgcattcccc tatgatgagc tccgaccct      2100 tacctgcgat ggtcatgata cttgggctc ttttcccctt acccttattg acgctctgga      2160
cacactcctt atcctcggaa acaccagcga atttcaaaga gtagttgaag tacttcagga     2220
caatgtcgac tttgacatcg atgtgaacgc atcagttttc gaaacaaata taagagtcgt     2280
tggaggtctg ctctccgccc accttctctc taaaaaagcc ggagtagaag ttgaagctgg     2340
ctggccctgc tccggacccc tccttcgtat ggctgaagaa gctgcccgca aactccttcc     2400
cgcttttcag accccaaccg gtatgcccta tggtactgtt aacctcctgc acggagtaaa     2460
tcccggcgaa acccccgtca catgtacagc cggaattgga acctttattg tggaatttgc     2520
```

| | |
|---|---|
| aacccttagc agcctgaccg agatcctgt attcgaagac gtggctcggg ttgccctgat | 2580 |
| gcgactgtgg gaatccaggt ctgatatcgg tctggtcggt aaccatatag acgtactcac | 2640 |
| tggtaaatgg gttgcacaag acgctggaat tggggcaggc gtggattctt attttgaata | 2700 |
| tctcgtaaaa ggggccatac tcttgcagga caaaaaactt atggctatgt tcctggaata | 2760 |
| taacaaagct attaggaact acacacactt cgatgattgg tatttgtggg tccaaatgta | 2820 |
| taaaggaacc gtttctatgc ctgtctttca gtcactggag gcttattggc ctggtctgca | 2880 |
| atccctgatc ggagacattg acaatgcaat gaggacattc cttaattatt acactgtttg | 2940 |
| gaagcagttc ggcggattgc ccgaatttta caacattcct caaggctata cagttgaaaa | 3000 |
| aagagaagga tatcccctgc gccccgagct tattgaaagc gctatgtatc tgtatcgtgc | 3060 |
| aacaggtgat ccaaccctgc ttgaactggg acgagacgcc gtcgaatcaa tcgagaaaat | 3120 |
| ttcaaaagtg gaatgcggct ttgcaacaat taaagatctt agagaccaca aactgggataa | 3180 |
| tcgcatggag tcattctttt tggctgagac cgtcaagtat ctgtatctgc ttttcatcc | 3240 |
| caacaacttc atccataata acgggtccac cttcgattca gtcatgaccc ctcacggtga | 3300 |
| atgcatactc ggagctggag gctatatttt taacactgaa gctcacccaa ttgacccagc | 3360 |
| tgcccttcat tgttgtcgac gtctgaaaga agaacaatgg gaggttgaag atttgatcaa | 3420 |
| agaatttac tcacttaaac aaagtcgacc taaacgcgca cagagaaaaa ctgtaagatc | 3480 |
| tggtccttgg gaacctcagt ccggcccagc aactctttca tcccccgcca accaaccacg | 3540 |
| agaaaaacaa ccagcccaac agagaaccccc ctgctcagc tgcccctctc agcccttcac | 3600 |
| ttcaaaactc gccctgcttg acaggtgtt tctggactcc tcttgattta aacacgcggc | 3660 |
| cgctaatcag ccataccaca tttgtagagg ttttacttgc tttaaaaaac ctcccacacc | 3720 |
| tcccctgaa cctgaaacat aaaatgaatg caattgttgt tgttaacttg tttattgcag | 3780 |
| cttataatgg ttacaaataa agcaatagca tcacaaattt cacaaataaa gcatttttt | 3840 |
| cactgcattc tagttgtggt ttgtccaaac tcatcaatgt atcttatcat gt | 3892 |

<210> SEQ ID NO 17
<211> LENGTH: 6629
<212> TYPE: DNA
<213> ORGANISM: Artificial
<220> FEATURE:
<223> OTHER INFORMATION: Synthetic plasmid

<400> SEQUENCE: 17

| | |
|---|---|
| aagcttatac tcgagctcta gattgggaac ccgggtctct cgaattcatg gtggtggtgg | 60 |
| ctgctgctcc ttctgctgct acagctgctc ctaaggtgct gctgctgtct ggacagcctg | 120 |
| cttctggagg aagagctctg cctctgatgg tgcctggacc tagagctgct ggatctgagg | 180 |
| cttctggaac acctcaggct agaaagagac agagactgac acatctgtct cctgaagaaa | 240 |
| aggctctgag aagaaagctg aagaatagag tggctgctca gacagctaga gatgaaagaa | 300 |
| aggctagaat gtctgaactg gaacagcagg tggtggatct ggaagaagaa aatcataagc | 360 |
| tgcagctgga aaatcagctg ctgagagaaa agacacatgg actggtggtg aaaatcagg | 420 |
| aactgagaac aagactggga atggatacac tggatcctga tgaagtgcct gaagtggaag | 480 |
| ctaagggatc tggagtgaga ctggtggctg atctgctga atctgctgct ggagctggac | 540 |
| ctgtggtgac atccctgaa catctgccta tggattctga tacagtggct tcttctgatt | 600 |
| ctgaatctga tatcctgctg ggaatcctgg ataagctgga tcctgatgtg tttttttaagt | 660 |
| gtccttctcc tgaatctgct tctctggaag aactgcctga agtgtatcct gaaggaccctt | 720 |

```
cttctctgcc tgcttctctg tctctgtctg tgggaacatc ttctgctaag ctggaagcta      780
tcaatgaact gatcagattt gatcatgtgt atacaaagcc tctggtgctg gaaatccctt      840
ctgaaacaga atctcagaca aatgtggtgg tgaagatcga agaagctcct ctgtcttctt      900
ctgaagaaga tcatcctgaa tttatcgtgt ctgtgaagaa ggaacctctg gaagatgatt      960
ttatccctga actgggaatc tctaatctgc tgtcttcttc tcattgtctg agacctcctt     1020
cttgtctgct ggatgctcat tctgattgtg gatatgaagg atctccttct ccttttctg      1080 atatgtcttc tcctctggga acagatcatt cttgggaaga tacatttgct aatgaactgt     1140
ttcctcagct gatctctgtg tgagcggccg ctaatcagcc ataccacatt tgtagaggtt     1200
ttacttgctt taaaaaacct cccacacctc cccctgaacc tgaaacataa aatgaatgca     1260
attgttgttg ttaacttgtt tattgcagct tataatggtt acaaataaag caatagcatc     1320
acaaatttca caaataaagc attttttca ctgcattcta gttgtggttt gtccaaactc      1380
atcaatgtat cttatcatgt ctaccggtag ggcccctctc ttcatgtgag caaaaggcca     1440
gcaaaaggcc aggaaccgta aaaaggccgc gttgctggcg ttttccata ggctccgccc      1500 ccctgacgag catcacaaaa atcgacgctc aagtcagagg tggcgaaacc cgacaggact     1560
ataaagatac caggcgtttc ccctggaag ctccctcgtg cgctctcctg ttccgaccct      1620
gccgcttacc ggatacctgt ccgcctttct cccttcggga agcgtggcgc tttctcatag     1680
ctcacgctgt aggtatctca gttcggtgta ggtcgttcgc tccaagctgg gctgtgtgca     1740
cgaacccccc gttcagcccg accgctgcgc cttatccggt aactatcgtc ttgagtccaa     1800
cccggtaaga cacgacttat cgccactggc agcagccact ggtaacagga ttagcagagc     1860
gaggtatgta ggcggtgcta cagagttctt gaagtggtgg cctaactacg gctacactag     1920
aaggacagta tttggtatct gcgctctgct gaagccagtt accttcggaa aaagagttgg     1980
tagctcttga tccggcaaac aaaccaccgc tggtagcggt ggtttttttg tttgcaagca     2040
gcagattacg cgcagaaaaa aaggatctca agaagatcct ttgatctttt ctacggggtc     2100
tgacgctcag tggaacgaaa actcacgtta agggattttg gtcatgggcg cgcctcatac     2160
tcctgcaggc atgagattat caaaaaggat cttcacctag atcctttaa attaaaaatg     2220 aagttttaaa tcaatctaaa gtatatatga gtaaacttgg tctgacagtt accaatgctt     2280
aatcagtgag gcacctatct cagcgatctg tctatttcgt tcatccatag ttgcctgact     2340
ccccgtcgtg tagataacta cgatacggga gggcttacca tctggcccca gtgctgcaat     2400
gataccgcga gacccacgct caccggctcc agatttatca gcaataaacc agccagccgg     2460
aagggccgag cgcagaagtg gtcctgcaac tttatccgcc tccatccagt ctattaattg     2520
ttgccgggaa gctagagtaa gtagttcgcc agttaatagt ttgcgcaacg ttgttgccat     2580
tgctacaggc atcgtggtgt cacgctcgtc gtttggtatg gcttcattca gctccggttc     2640
ccaacgatca aggcgagtta catgatcccc catgttgtgc aaaaaagcgg ttagctcctt     2700
cggtcctccg atcgttgtca gaagtaagtt ggccgcagtg ttatcactca tggttatggc     2760
agcactgcat aattctctta ctgtcatgcc atccgtaaga tgcttttctg tgactggtga     2820
gtactcaacc aagtcattct gagaatagtg tatgcggcga ccgagttgct cttgcccggc     2880
gtcaatacgg gataataccg cgccacatag cagaacttta aaagtgctca tcattggaaa     2940
acgttcttcg gggcgaaaac tctcaaggat cttaccgctg ttgagatcca gttcgatgta     3000
acccactcgt gcacccaact gatcttcagc atcttttact ttcaccagcg tttctgggtg     3060
```

```
agcaaaaaca ggaaggcaaa atgccgcaaa aaagggaata agggcgacac ggaaatgttg    3120
aatactcata ctcttccttt ttcaatatta ttgaagcatt tatcagggtt attgtctcat    3180
gagcggatac atatttgaat gtatttagaa aaataaacaa atagggggttc cgcgcacatt   3240 tccccgaaaa gtgccacctg acgtcaggta ccaagcctag gcctccaaaa aagcctcctc    3300
actacttctg gaatagctca gaggcagagg cggcctcggc ctctgcataa ataaaaaaaa    3360
ttagtcagcc atggggcgga gaatgggcgg aactgggcgg agttaggggc gggatgggcg    3420
gagttagggg cgggactatg gttgctgact aattgagatg catgctttgc atacttctgc    3480
ctgctgggga gcctggggac tttccacacc tggttgctga ctaattgaga tgcatgcttt    3540
gcatacttct gcctgctggg gagcctgggg actttccaca ccggatccac catggccaag    3600
ttgaccagtg ccgttccggt gctcaccgcg cgcgacgtcg ccggagcggt cgagttctgg    3660
accgaccggc tcgggttctc ccgggacttc gtggaggacg acttcgccgg tgtggtccgg    3720
gacgacgtga ccctgttcat cagcgcggtc caggaccagg tggtgccgga caacaccctg    3780
gcctgggtgt gggtgcgcgg cctggacgag ctgtacgccg agtggtcgga ggtcgtgtcc    3840
acgaacttcc gggacgcctc cgggccggcc atgaccgaga tcggcgagca gccgtggggg    3900
cgggagttcg ccctgcgcga cccggccggc aactgcgtgc acttcgtggc cgaggagcag    3960
gactgaacgc gtgctgtaag tctgcagaaa ttgatgatct attaaacaat aaagatgtcc    4020
actaaaatgg aagttttttcc tgtcatactt tgttaagaag ggtgagaaca gagtacctac    4080
attttgaatg gaaggattgg agctacgggg gtgggggtgg ggtgggatta gataaatgcc    4140
tgctctttac tgaaggctct ttactattgc tttatgataa tgtttcatag ttggatatca    4200
taatttaaac aagcaaaacc aaattaaggg ccagctcatt cctcccactc atgatctatg    4260
gatctataga tctctcgtgc agctgggggct ctagggggta tccccacgcg ccctgtagcg    4320
gcgcattaag cgcggcgggt gtggtggtta cgcgcagcgt gaccgctaca cttgccagcg    4380
ccctagcgcc cgctcctttc gctttcttcc cttcctttct cgccacgttc gccggctttc    4440
cccgtcaagc tctaaatcgg gggctccctt tagggttccg atttagtgct ttacggcacc    4500
tcgaccccaa aaaacttgat tagggtgatg gttcacgtag tgggccatcg ccctgataga    4560
cggtttttcg ccctttgacg ttggagtcca cgttctttaa tagtggactc ttgttccaaa    4620
ctggaacaac actcaaccct atctcggtct attcttttga tttataaggg attttgccga    4680
tttcggccta ttggttaaaa atgagctgat ttaacaaaa atttaacgcg aattaattct    4740
gtggaatgtg tgtcagttag tcgcgaggcc tccgcgccgg gttttggcgc ctcccgcggg    4800
cgcccccctc ctcacggcga cgctgccac gtcagacgaa gggcgcagcg agcgtcctga    4860
tccttccgcc cggacgctca ggacagcggc ccgctgctca taagactcgg ccttagaacc    4920
ccagtatcag cagaaggaca ttttaggacg ggacttgggt gactctaggg cactggtttt    4980
ctttccagag agcggaacag gcgaggaaaa gtagtcccctt ctcggcgatt ctgcggaggg    5040
atctccgtgg ggcggtgaac gccgatgatt atataaggac gcgccgggtg tggcacagct    5100
agttccgtcg cagccgggat ttgggtcgcg gttcttgttt gtggatcgct gtgatcgtca    5160
cttggtgagt agcgggctgc tgggctgcc ggggctttcg tggccgccgg gccgctcggt    5220
gggacggaag cgtgtggaga accgccaag ggctgtagtc tgggtccgcg agcaaggttg    5280
ccctgaactg ggggttgggg ggagcgcagc aaaatggcgg ctgttcccga gtcttgaatg    5340
gaagacgctt gtgaggcggg ctgtgaggtc gttgaaacaa ggtgggggc atggtgggcg    5400 gcaagaaccc aaggtcttga ggccttcgct aatgcgggaa agctcttatt cgggtgagat    5460
```

```
gggctggggc accatctggg gaccctgacg tgaagtttgt cactgactgg agaactcggt    5520
ttgtcgtctg ttgcggggc ggcagttatg gcggtgccgt tgggcagtgc acccgtacct    5580
ttgggagcgc gcgccctcgt cgtgtcgtga cgtcacccgt tctgttggct tataatgcag    5640 ggtgggggcca cctgccggta ggtgtgcggt aggcttttct ccgtcgcagg acgcagggtt    5700
cgggcctagg gtaggctctc ctgaatcgac aggcgccgga cctctggtga ggggagggat    5760
aagtgaggcg tcagtttctt tggtcggttt tatgtaccta tcttcttaag tagctgaagc    5820
tccggttttg aactatgcgc tcggggttgg cgagtgtgtt ttgtgaagtt ttttaggcac    5880
cttttgaaat gtaatcattt gggtcaatat gtaattttca gtgttagact agtaaattgt    5940
ccgctaaatt ctggccgttt ttggcttttt tgttagacgt cgaccgatcc tgagaacttc    6000
agggtgagtt tggggaccct tgattgttct ttctttttcg ctattgtaaa attcatgtta    6060
tatggagggg gcaaagtttt cagggtgttg tttagaatgg aagatgtcc cttgtatcac    6120 catgacccct catgataatt tgtttctttt cactttctac tctgttgaca accattgtct    6180
cctcttattt tcttttcatt ttctgtaact ttttcgttaa actttagctt gcatttgtaa    6240 cgaatttttta aattcacttt tgtttatttg tcagattgta agtactttct ctaatcactt    6300 tttttttcaag gcaatcaggg tatattatat tgtacttcag cacagttta gagaacaatt    6360 gttataatta aatgataagg tagaatattt ctgcatataa attctggctg gcgtggaaat    6420
attcttattg gtagaaacaa ctacaccctg gtcatcatcc tgcctttctc tttatggtta    6480
caatgatata cactgtttga gatgaggata aaatactctg agtccaaacc gggcccctct    6540
gctaaccatg ttcatgcctt cttctctttc ctacagctcc tgggcaacgt gctggttgtt    6600
gtgctgtctc atcatttttgg caaagaatt                                    6629

<210> SEQ ID NO 18
<211> LENGTH: 3264
<212> TYPE: DNA
<213> ORGANISM: Artificial
<220> FEATURE:
<223> OTHER INFORMATION: Synthetic construct

<400> SEQUENCE: 18
ggcctccgcg ccgggttttg gcgcctcccg cgggcgcccc cctcctcacg gcgagcgctg     60
ccacgtcaga cgaagggcgc agcgagcgtc ctgatccttc cgcccggacg ctcaggacag    120
cggcccgctg ctcataagac tcggccttag aaccccagta tcagcagaag gacattttag    180
gacgggactt gggtgactct agggcactgg ttttctttcc agagagcgga acaggcgagg    240
aaaagtagtc ccttctcggc gattctgcgg agggatctcc gtgggcggt gaacgccgat    300 gattatataa ggacgcgccg ggtgtggcac agctagttcc gtcgcagccg ggatttgggt    360
cgcggttctt gtttgtggat cgctgtgatc gtcacttggt gagtagcggg ctgctgggct    420
ggccggggct ttcgtggccg ccgggccgct cggtgggacg gaagcgtgtg gagagaccgc    480
caagggctgt agtctgggtc cgcgagcaag gttgccctga actgggggtt gggggagcg    540 cagcaaaatg gcggctgttc ccgagtcttg aatggaagac gcttgtgagg cgggctgtga    600
ggtcgttgaa acaaggtggg gggcatggtg gcggcaaga acccaaggtc ttgaggcctt    660
cgctaatgcg ggaaagctct tattcgggtg agatgggctg gggcaccatc tggggaccct    720
gacgtgaagt ttgtcactga ctggagaact cggtttgtcg tctgttgcgg gggcggcagt    780
tatggcggtg ccgttgggca gtgcacccgt acctttggga gcgcgcgccc tcgtcgtgtc    840
```

```
gtgacgtcac ccgttctgtt ggcttataat gcagggtggg gccacctgcc ggtaggtgtg    900
cggtaggctt ttctccgtcg caggacgcag ggttcgggcc tagggtaggc tctcctgaat    960
cgacaggcgc cggacctctg gtgaggggag ggataagtga ggcgtcagtt tctttggtcg   1020
gttttatgta cctatcttct taagtagctg aagctccggt tttgaactat gcgctcgggg   1080
ttggcgagtg tgttttgtga agttttttag gcacctttg  aaatgtaatc atttgggtca   1140
atatgtaatt ttcagtgtta gactagtaaa ttgtccgcta aattctggcc gttttggct    1200
tttttgttag acgtcgaccg atcctgagaa cttcagggtg agtttgggga cccttgattg   1260
ttctttcttt ttcgctattg taaaattcat gttatatgga gggggcaaag ttttcagggt   1320
gttgtttaga atgggaagat gtcccttgta tcaccatgga ccctcatgat aattttgttt   1380
ctttcacttt ctactctgtt gacaaccatt gtctcctctt atttctttt  catttctgt    1440
aacttttcg  ttaaactta  gcttgcattt gtaacgaatt tttaaattca cttttgttta   1500
tttgtcagat tgtaagtact ttctctaatc acttttttt  caaggcaatc agggtatatt   1560
atattgtact tcagcacagt tttagagaac aattgttata attaaatgat aaggtagaat   1620
atttctgcat ataaattctg gctggcgtgg aaatattctt attggtagaa acaactacac   1680
cctggtcatc atcctgcctt tctctttatg gttacaatga tatacactgt ttgagatgag   1740
gataaaatac tctgagtcca aaccgggccc ctctgctaac catgttcatg ccttcttctc   1800
tttcctacag ctcctgggca acgtgctggt tgttgtgctg tctcatcatt ttggcaaaga   1860
attaagctta tactcgagct ctagattggg aacccgggtc tctcgaattc atggtggtgg   1920
tggctgctgc tccttctgct gctacagctg ctcctaaggt gctgctgctg tctggacagc   1980
ctgcttctgg aggaagagct ctgcctctga tggtgcctgg acctagagct gctggatctg   2040
aggcttctgg aacacctcag gctagaaaga gacagagact gacacatctg tctcctgaag   2100
aaaaggctct gagaagaaag ctgaagaata gagtggctgc tcagacagct agagatagaa   2160
agaaggctag aatgtctgaa ctggaacagc aggtggtgga tctggaagaa gaaaatcata   2220
agctgcagct ggaaaatcag ctgctgagag aaaagacaca tggactggtg gtggaaaatc   2280
aggaactgag aacaagactg ggaatggata cactggatcc tgatgaagtg cctgaagtgg   2340
aagctaaggg atctggagtg agactggtgg ctggatctgc tgaatctgct gctggagctg   2400
gacctgtggt gacatctcct gaacatctgc ctatggattc tgatacagtg gcttcttctg   2460
attctgaatc tgatatcctg ctgggaatcc tggataagct ggatcctgtg atgtttttta   2520
agtgtccttc tcctgaatct gcttctctgg aagaactgcc tgaagtgtat cctgaaggac   2580
cttcttctct gcctgcttct ctgtctctgt ctgtgggaac atcttctgct aagctggaag   2640
ctatcaatga actgatcaga tttgatcatg tgtatacaaa gcctctggtg ctggaaatcc   2700
cttctgaaac agaatctcag acaaatgtgg tggtgaagat cgaagaagct cctctgtctt   2760
cttctgaaga agatcatcct gaatttatcg tgtctgtgaa gaaggaacct ctggaagatg   2820
attttatccc tgaactggga atctctaatc tgctgtcttc ttctcattgt ctgagacctc   2880
cttcttgtct gctggatgct cattctgatt gtggatatga aggatctcct tctccttttt   2940
ctgatatgtc ttctcctctg gaacagatc  attcttggga agatacattt gctaatgaac   3000
tgtttcctca gctgatctct gtgtgagcgg ccgctaatca gccataccac atttgtagag   3060
gttttacttg ctttaaaaaa cctcccacac ctcccctga  acctgaaaca taaaatgaat   3120
gcaattgttg ttgttaactt gtttattgca gcttataatg gttacaaata aagcaatagc   3180
atcacaaatt tcacaaataa agcatttttt tcactgcatt ctagttgtgg tttgtccaaa   3240
```
ctcatcaatg tatcttatca tgtc                                       3264

<210> SEQ ID NO 19
<211> LENGTH: 447
<212> TYPE: PRT
<213> ORGANISM: Homo sapiens

<400> SEQUENCE: 19

```
Glu Val Gln Val Leu Glu Ser Gly Gly Asp Leu Val Gln Pro Gly Gly
 1               5                  10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Ser Ala Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                85                  90                  95

Ala Lys Asp Gly Ala Trp Lys Met Ser Gly Leu Asp Val Trp Gly Gln
            100                 105                 110

Gly Thr Thr Val Ile Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365
```

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 20
<211> LENGTH: 110
<212> TYPE: PRT
<213> ORGANISM: Homo sapiens

<400> SEQUENCE: 20

Glu Ser Gly Gly Asp Leu Val Gln Pro Gly Gly Ser Leu Arg Leu Ser
1               5                   10                  15

Cys Ala Ala Ser Gly Phe Thr Phe Ser Ala Tyr Ala Met Thr Trp Val
                20                  25                  30

Arg Gln Ala Pro Gly Lys Gly Leu Glu Trp Val Ser Ala Ile Ser Gly
            35                  40                  45

Ser Gly Gly Ser Ala Tyr Tyr Ala Asp Ser Val Lys Gly Arg Phe Thr
        50                  55                  60

Ile Ser Arg Asp Asn Ser Lys Asn Thr Val Tyr Leu Gln Met Asn Ser
65                  70                  75                  80

Leu Arg Ala Glu Asp Thr Ala Val Tyr Tyr Cys Ala Lys Asp Gly Ala
                85                  90                  95

Trp Lys Met Ser Gly Leu Asp Val Trp Gly Gln Gly Thr Thr
                100                 105                 110

<210> SEQ ID NO 21
<211> LENGTH: 214
<212> TYPE: PRT
<213> ORGANISM: Homo sapiens

<400> SEQUENCE: 21

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
                20                  25                  30

Leu Ala Trp Tyr Gln Gln Lys Pro Gly Lys Ile Pro Arg Leu Leu Ile
            35                  40                  45

Tyr Thr Thr Ser Thr Leu Gln Ser Gly Val Pro Ser Arg Phe Arg Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 22
<211> LENGTH: 100
<212> TYPE: PRT
<213> ORGANISM: Homo sapiens

<400> SEQUENCE: 22

Gln Ser Pro Ala Ser Leu Ser Ala Ser Val Gly Asp Arg Val Thr Ile
1               5                   10                  15

Thr Cys Arg Ala Ser Gln Asp Ile Ser Asp Tyr Leu Ala Trp Tyr Gln
            20                  25                  30

Gln Lys Pro Gly Lys Ile Pro Arg Leu Leu Ile Tyr Thr Thr Ser Thr
        35                  40                  45

Leu Gln Ser Gly Val Pro Ser Arg Phe Arg Gly Ser Gly Ser Gly Thr
    50                  55                  60

Asp Phe Thr Leu Thr Ile Ser Ser Leu Gln Pro Glu Asp Val Ala Thr
65                  70                  75                  80

Tyr Tyr Cys Gln Lys Tyr Asp Ser Ala Pro Leu Thr Phe Gly Gly Gly
            85                  90                  95

Thr Lys Val Glu
        100

<210> SEQ ID NO 23
<211> LENGTH: 2971
<212> TYPE: DNA
<213> ORGANISM: Artificial
<220> FEATURE:
<223> OTHER INFORMATION: Synthetic construct

<400> SEQUENCE: 23
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtgggag gtctatataa gcagagctca tgatagaagc actctactat tcgtcgaccg   600
atcctgagaa cttcagggtg agtttgggga cccttgattg ttctttcttt ttcgctattg   660
taaaattcat gttatatgga gggggcaaag ttttcagggt gttgtttaga atgggaagat   720

```
gtcccttgta tcaccatgga ccctcatgat aattttgttt ctttcacttt ctactctgtt    780
gacaaccatt gtctcctctt attttctttt cattttctgt aacttttttcg ttaaacttta   840
gcttgcattt gtaacgaatt tttaaattca cttttgttta tttgtcagat tgtaagtact    900
ttctctaatc acttttttttt caaggcaatc agggtatatt atattgtact tcagcacagt   960
tttagagaac aattgttata attaaatgat aaggtagaat atttctgcat ataaattctg   1020
gctggcgtgg aaatattctt attggtagaa acaactacac cctggtcatc atcctgcctt   1080
tctctttatg gttacaatga tatacactgt ttgagatgag gataaaatac tctgagtcca   1140
aaccgggccc ctctgctaac catgttcatg ccttcttctc tttcctacag ctcctgggca   1200
acgtgctggt tgttgtgctg tctcatcatt ttggcaaaga attaagctta tactcgagct   1260
ctagattggg aacccgggtc tctcgaattc gagatctcca ccatgcacag acctagacgt   1320
cgtggaactc gtccacctcc actggcactg ctcgctgctc tcctcctggc tgcacgtggt   1380
gctgatgcag aggtgcaggt gttggagtct gggggagact tggtacagcc tgggggggtcc   1440
ctgagactct cctgtgcagc ctctggattc acctttagtg cctatgccat gacctgggtc   1500
cgccaggctc cagggaaggg gctggagtgg gtctcagcta ttagtggtag tggtggtagc   1560
gcatactacg cagactccgt gaagggccgg ttcaccatct ccagagacaa ttccaagaac   1620
acggtatatc tgcagatgaa cagcctgaga gccgaggaca cggccgtata ttactgtgcg   1680
aaagatgggg cctggaaaat gtccggtttg gacgtctggg gccaagggac cacggtcatc   1740
gtctcctcag cctccaccaa gggcccatcg gtcttccccc tggcgccctg ctccaggagc   1800
acctccgaga gcacagccgc cctgggctgc ctggtcaagg actacttccc cgaaccggtg   1860
acggtgtcgt ggaactcagg cgccctgacc agcggcgtgc acaccttccc ggctgtccta   1920
cagtcctcag gactctactc cctcagcagc gtggtgaccg tgccctccag cagcttgggc   1980
acgaagacct acacctgcaa cgtagatcac aagcccagca acaccaaggt ggacaagaga   2040
gttgagtcca aatatggtcc cccatgccca ccctgcccag cacctgagtt cctggggggga   2100
ccatcagtct tcctgttccc cccaaaaccc aaggacactc tcatgatctc ccggacccct   2160
gaggtcacgt gcgtggtggt ggacgtgagc caggaagacc ccgaggtcca gttcaactgg   2220
tacgtggatg gcgtggaggt gcataatgcc aagacaaagc cgcgggagga gcagttcaac   2280
agcacgtacc gtgtggtcag cgtcctcacc gtcctgcacc aggactggct gaacggcaag   2340
gagtacaagt gcaaggtctc caacaaaggc ctcccgtcct ccatcgagaa aaccatctcc   2400
aaagccaaag gcagccccg agagccacag gtgtacaccc tgcccccatc ccaggaggag   2460
atgaccaaga accaggtcag cctgacctgc ctggtcaaag gcttctaccc cagcgacatc   2520
gccgtggagt gggagagcaa tgggcagccg gagaacaact acaagaccac gcctcccgtg   2580
ctggactccg acggctcctt cttcctctac agcaggctca ccgtggacaa gagcaggtgg   2640
caggagggga atgtcttctc atgctccgtg atgcatgagg ctctgcacaa ccactacaca   2700
cagaagtccc tctccctgtc tctgggtaaa tgagcggccg ctaatcagcc ataccacatt   2760
tgtagaggtt ttacttgctt taaaaaacct cccacacctc ccctgaacc tgaaacataa    2820
aatgaatgca attgttgttg ttaacttgtt tattgcagct tataatggtt acaaataaag   2880
caatagcatc acaaatttca caaataaagc attttttttca ctgcattcta gttgtggttt   2940
gtccaaactc atcaatgtat cttatcatgt c                                   2971

<210> SEQ ID NO 24
<211> LENGTH: 7013
```

```
<212> TYPE: DNA
<213> ORGANISM: Artificial
<220> FEATURE:
<223> OTHER INFORMATION: Synthetic plasmid

<400> SEQUENCE: 24
tcgcgatgtg tgactagtta gttattaata gtaatcaatt acggggtcat tagttcatag      60
cccatatatg gagttccgcg ttacataact tacggtaaat ggcccgcctg gctgaccgcc     120
caacgacccc cgcccattga cgtcaataat gacgtatgtt cccatagtaa cgccaatagg     180
gactttccat tgacgtcaat gggtggagta tttacggtaa actgcccact tggcagtaca     240
tcaagtgtat catatgccaa gtacgccccc tattgacgtc aatgacggta atggcccgc      300 ctggcattat gcccagtaca tgaccttatg gactttcct acttggcagt acatctacgt      360
attagtcatc gctattacca tggtgatgcg gttttggcag tacatcaatg ggcgtggata     420
gcggtttgac tcacggggat ttccaagtct caccccatt gacgtcaatg ggagtttgtt      480
ttggcaccaa aatcaacggg actttccaaa atgtcgtaac aactccgccc cattgacgca     540
aatgggcggt aggcgtgtac ggtgggaggt ctatataagc agagctcatg atagaagcac     600
tctactattc gtcgaccgat cctgagaact tcagggtgag tttggggacc cttgattgtt     660
cttctttttt cgctattgta aaattcatgt tatatggagg gggcaaagtt ttcagggtgt     720
tgtttagaat gggaagatgt cccttgtatc accatggacc ctcatgataa ttttgtttct     780
ttcactttct actctgttga caaccattgt ctcctcttat tttcttttca ttttctgtaa     840 cttttcgtt aaactttagc ttgcatttgt aacgaatttt taaattcact tttgtttatt      900
tgtcagattg taagtacttt ctctaatcac ttttttttca aggcaatcag ggtatattat     960
attgtacttc agcacagttt tagagaacaa ttgttataat taaatgataa ggtagaatat    1020
ttctgcatat aaattctggc tggcgtggaa atattcttat tggtagaaac aactacaccc    1080
tggtcatcat cctgcctttc tctttatggt tacaatgata tacactgttt gagatgagga    1140
taaaatactc tgagtccaaa ccgggcccct ctgctaacca tgttcatgcc ttcttctctt    1200
tcctacagct cctgggcaac gtgctggttg ttgtgctgtc tcatcatttt ggcaaagaat    1260
taagcttata ctcgagctct agattgggaa cccgggtctc tcgaattcga gatctccacc    1320
atgcacagac ctagacgtcg tggaactcgt ccacctccac tggcactgct cgctgctctc    1380
ctcctggctg cacgtggtgc tgatgcagag gtgcaggtgt tggagtctgg gggagacttg    1440
gtacagcctg gggggtccct gagactctcc tgtgcagcct ctggattcac ctttagtgcc    1500
tatgccatga cctgggtccg ccaggctcca gggaagggc tggagtgggt ctcagctatt    1560
agtggtagtg gtggtagcgc atactacgca gactccgtga agggccggtt caccatctcc    1620
agagacaatt ccaagaacac ggtatatctg cagatgaaca gcctgagagc cgaggacacg    1680
gccgtatatt actgtgcgaa agatgggcc tggaaaatgt ccggtttgga cgtctgggc     1740 caagggacca cggtcatcgt ctcctcagcc tccaccaagg gccatcggt cttcccctg       1800 gcgccctgct ccaggagcac ctccgagagc acagccgccc tgggctgcct ggtcaaggac    1860
tacttccccg aaccggtgac ggtgtcgtgg aactcaggcg ccctgaccag cggcgtgcac    1920
accttcccgg ctgtcctaca gtcctcagga ctctactccc tcagcagcgt ggtgaccgtg    1980
ccctccagca gcttgggcac gaagacctac acctgcaacg tagatcacaa gcccagcaac    2040
accaaggtgg acaagagagt tgagtccaaa tatggtcccc catgcccacc ctgcccagca    2100
cctgagttcc tggggggacc atcagtcttc ctgttccccc caaaacccaa ggacactctc    2160
```

```
atgatctccc ggacccctga ggtcacgtgc gtggtggtgg acgtgagcca ggaagacccc    2220
gaggtccagt tcaactggta cgtggatggc gtggaggtgc ataatgccaa gacaaagccg    2280
cgggaggagc agttcaacag cacgtaccgt gtggtcagcg tcctcaccgt cctgcaccag    2340
gactggctga acggcaagga gtacaagtgc aaggtctcca acaaaggcct cccgtcctcc    2400
atcgagaaaa ccatctccaa agccaaaggg cagccccgag agccacaggt gtacaccctg    2460
cccccatccc aggaggagat gaccaagaac caggtcagcc tgacctgcct ggtcaaaggc    2520
ttctacccca gcgacatcgc cgtggagtgg gagagcaatg ggcagccgga gaacaactac    2580
aagaccacgc ctcccgtgct ggactccgac ggctccttct cctctacag caggctcacc    2640 gtggacaaga gcaggtggca ggaggggaat gtcttctcat gctccgtgat gcatgaggct    2700
ctgcacaacc actacacaca gaagtccctc tccctgtctc tgggtaaatg agcggccgct    2760
aatcagccat accacatttg tagaggtttt acttgcttta aaaaacctcc cacacctccc    2820
cctgaacctg aaacataaaa tgaatgcaat tgttgttgtt aacttgttta ttgcagctta    2880
taatggttac aaataaagca atagcatcac aaatttcaca ataaagcat ttttttcact    2940 gcattctagt tgtggtttgt ccaaactcat caatgtatct tatcatgtct accggtcctg    3000
cagggcccct ctcttcatgt gagcaaaagg ccagcaaaag gccaggaacc gtaaaaaggc    3060
cgcgttgctg gcgttttcc ataggctccg ccccctgac gagcatcaca aaaatcgacg    3120
ctcaagtcag aggtggcgaa acccgacagg actataaaga taccaggcgt ttccccctgg    3180
aagctccctc gtgcgctctc ctgttccgac cctgccgctt accggatacc tgtccgcctt    3240
tctcccttcg ggaagcgtgg cgctttctca atgctcacgc tgtaggtatc tcagttcggt    3300
gtaggtcgtt cgctccaagc tgggctgtgt gcacgaaccc cccgttcagc ccgaccgctg    3360
cgccttatcc ggtaactatc gtcttgagtc caacccggta agacacgact tatcgccact    3420
ggcagcagcc actggtaaca ggattagcag agcgaggtat gtaggcggtg ctacagagtt    3480
cttgaagtgg tggcctaact acggctacac tagaaggaca gtatttggta tctgcgctct    3540
gctgaagcca gttaccttcg gaaaaagagt tggtagctct tgatccggca aacaaaccac    3600
cgctggtagc ggtggttttt tgtttgcaa gcagcagatt acgcgcagaa aaaaaggatc    3660
tcaagaagat cctttgatct tttctacggg gtctgacgct cagtggaacg aaaactcacg    3720
ttaagggatt ttggtcatgg cgcgcctca tactcctgca ggcatgagat tatcaaaaag    3780
gatcttcacc tagatccttt taaattaaaa atgaagttt aaatcaatct aaagtatata    3840
tgagtaaact tggtctgaca gttaccaatg cttaatcagt gaggcaccta tctcagcgat    3900
ctgtctattt cgttcatcca tagttgcctg actccccgtc gtgtagataa ctacgatacg    3960
ggagggctta ccatctggcc ccagtgctgc aatgatacc cgagacccac gctcaccggc    4020
tccagattta tcagcaataa accagccagc cggaagggcc gagcgcagaa gtggtcctgc    4080
aactttatcc gcctccatcc agtctattaa ttgttgccgg gaagctagag taagtagttc    4140
gccagttaat agtttgcgca acgttgttgc cattgctaca ggcatcgtgg tgtcacgctc    4200
gtcgtttggt atggcttcat tcagctccgg ttcccaacga tcaaggcgag ttacatgatc    4260
ccccatgttg tgcaaaaaag cggttagctc cttcggtcct ccgatcgttg tcagaagtaa    4320
gttggccgca gtgttatcac tcatggttat ggcagcactg cataattctc ttactgtcat    4380
gccatccgta agatgctttt ctgtgactgg tgagtactca accaagtcat tctgagaata    4440
gtgtatgcgg cgaccgagtt gctcttgccc ggcgtcaata cgggataata ccgcgccaca    4500
tagcagaact ttaaaagtgc tcatcattgg aaaacgttct tcggggcgaa aactctcaag    4560
```

```
gatcttaccg ctgttgagat ccagttcgat gtaacccact cgtgcaccca actgatcttc    4620
agcatctttt actttcacca gcgtttctgg gtgagcaaaa acaggaaggc aaaatgccgc    4680
aaaaaaggga ataagggcga cacggaaatg ttgaatactc atactcttcc tttttcaata    4740
ttattgaagc atttatcagg gttattgtct catgagcgga tacatatttg aatgtattta    4800
gaaaaataaa caaatagggg ttccgcgcac atttccccga aaagtgccac ctgacgtcag    4860
gtaccaagcc taggcctcca aaaagcctc ctcactactt ctggaatagc tcagaggcag     4920
aggcggcctc ggcctctgca taaataaaaa aaattagtca gccatggggc ggagaatggg    4980
cggaactggg cggagttagg ggcgggatgg gcggagttag gggcgggact atggttgctg    5040
actaattgag atgcatgctt tgcatacttc tgcctgctgg ggagcctggg actttccac    5100 acctggttgc tgactaattg agatgcatgc tttgcatact ctgcctgct ggggagcctg     5160 gggactttcc acaccggatc caccatggat agatccggaa agcctgaact caccgcgacg    5220
tctgtcgaga gtttctgat cgaaaagttc gacagcgtct ccgacctgat gcagctctcg      5280
gagggcgaag aatctcgtgc tttcagcttc gatgtaggag ggcgtggata tgtcctgcgg    5340
gtaaatagct gcgccgatgg tttctacaaa gatcgttatg tttatcggca ctttgcatcg    5400
gccgcgctcc cgattccgga agtgcttgac attggggagt tcagcgagag cctgacctat    5460
tgcatctccc gccgtgcaca gggtgtcacg ttgcaagacc tgcctgaaac cgaactgccc    5520
gctgttctgc agccggtcgc ggaggccatg gatgcgatcg ctgcggccga tcttagccag    5580
acgagcgggt tcggcccatt cggaccgcaa ggaatcggtc aatacactac atggcgtgat    5640
ttcatatgcg cgattgctga tcccatgtg tatcactggc aaactgtgat ggacgacacc     5700
gtcagtgcgt ccgtcgcgca ggctctcgat gagctgatgc tttgggccga ggactgcccc    5760
gaagtccggc acctcgtgca cgcggatttc ggctccaaca atgtcctgac ggacaatggc    5820
cgcataacag cggtcattga ctggagcgag gcgatgttcg gggattccca atacgaggtc    5880
gccaacatct tcttctggag gccgtggttg gcttgtatgg agcagcagac gcgctacttc    5940
gagcggaggc atccggagct tgcaggatcg ccgcggctcc gggcgtatat gctccgcatt    6000
ggtcttgacc aactctatca gagcttggtt gacggcaatt tcgatgatgc agcttgggcg    6060
cagggtcgat gcgacgcaat cgtccgatcc ggagccggga ctgtcgggcg tacacaaatc    6120
gcccgcagaa gcgcggccgt ctggaccgat ggctgtgtag aagtactcgc cgatagtgga    6180
aaccgacgcc ccagcactcg tccgagggca aaggaataga gcgtgctgt aagtctgcag     6240 aaattgatga tctattaaac aataaagatg tccactaaaa tggaagtttt tcctgtcata    6300
ctttgttaag aagggtgaga acagagtacc tacattttga atggaaggat tggagctacg    6360
ggggtggggg tggggtggga ttagataaat gcctgctctt tactgaaggc tctttactat    6420
tgctttatga taatgtttca tagttggata tcataattta acaagcaaa accaaattaa     6480 gggccagctc attcctccca ctcatgatct atggatctat agatctctcg tgcagctggg    6540
gctctagggg gtatccccac gcgccctgta gcggcgcatt aagcgcggcg ggtgtggtgg    6600
ttacgcgcag cgtgaccgct acacttgcca gcgccctagc gcccgctcct ttcgctttct    6660
tcccttcctt tctcgccacg ttcgccggct ttccccgtca agctctaaat cgggggctcc    6720
ctttagggtt ccgatttagt gctttacggc acctcgaccc caaaaaactt gattagggtg    6780
atggttcacg tagtgggcca tcgccctgat agacggtttt tcgccctttg acgttggagt    6840
ccacgttctt taatagtgga ctcttgttcc aaactggaac aacactcaac cctatctcgg    6900
``` tctattctttt tgatttataa gggattttgc cgatttcggc ctattggtta aaaaatgagc    6960
tgatttaaca aaaatttaac gcgaattaat tctgtggaat gtgtgtcagt tag    7013

<210> SEQ ID NO 25
<211> LENGTH: 2272
<212> TYPE: DNA
<213> ORGANISM: Artificial
<220> FEATURE:
<223> OTHER INFORMATION: Synthetic construct

<400> SEQUENCE: 25

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctca tgatagaagc actctactat cgtcgaccg      600 atcctgagaa cttcagggtg agtttgggga cccttgattg ttctttcttt ttcgctattg     660
taaaattcat gttatatgga gggggcaaag ttttcagggt gttgtttaga atgggaagat     720
gtcccttgta tcaccatgga ccctcatgat aattttgttt ctttcacttt ctactctgtt     780
gacaaccatt gtctcctctt attttctttt cattttctgt aacttttcg ttaaacttta      840 gcttgcattt gtaacgaatt tttaaattca cttttgttta tttgtcagat tgtaagtact     900
ttctctaatc acttttttt caaggcaatc agggtatatt atattgtact tcagcacagt      960
tttagagaac aattgttata attaaatgat aaggtagaat atttctgcat ataaattctg    1020
gctggcgtgg aaatattctt attggtagaa acaactacac cctggtcatc atcctgcctt    1080
tctctttatg gttacaatga tatacactgt ttgagatgag gataaaatac tctgagtcca    1140
aaccgggccc ctctgctaac catgttcatg ccttcttctc tttcctacag ctcctgggca    1200
acgtgctggt tgttgtgctg tctcatcatt ttggcaaaga attaagctta tactcgagct    1260
ctagattggg aacccgggtc tctcgaattc gagatctcca ccatgcacag acctagacgt    1320
cgtggaactc gtccacctcc actggcactg ctcgctgctc tcctcctggc tgcacgtggt    1380
gctgatgcag acatccagat gacccagtct ccagcctccc tgtctgcatc tgttggagac    1440
agagtcacca tcacttgtcg ggcgagtcag gacattagcg attatttagc ctggtatcag    1500
cagaaaccag ggaaaattcc taggctcctg atctatacta catccacttt gcaatcaggg    1560
gtcccatctc ggttccgtgg cagtgggtct gggacagatt tcactctcac catcagcagc    1620
ctgcagcctg aagatgttgc aacttattac tgtcagaagt atgacagtgc cccgctcact    1680
ttcggcggag ggaccaaggt ggagatcaaa cgaactgtgg ctgcaccatc tgtcttcatc    1740
ttcccgccat ctgatgagca gttgaaatct ggaactgcct ctgttgtgtg cctgctgaat    1800
aacttctatc ccagagaggc caaagtacag tggaaggtgg ataacgccct ccaatcgggt    1860
aactcccagg agagtgtcac agagcaggac agcaaggaca gcacctacag cctcagcagc    1920
accctgacgc tgagcaaagc agactacgag aaacacaaag tctacgcctg cgaagtcacc    1980
```

```
catcagggcc tgagctcgcc cgtcacaaag agcttcaaca ggggagagtg ttaggcggcc   2040
gctaatcagc cataccacat ttgtagaggt tttacttgct ttaaaaaacc tcccacacct   2100 cccctgaac  ctgaaacata aatgaatgc  aattgttgtt gttaacttgt ttattgcagc    2160
ttataatggt tacaaataaa gcaatagcat cacaaatttc acaaataaag cattttttc    2220 actgcattct agttgtggtt tgtccaaact catcaatgta tcttatcatg tc            2272
```

<210> SEQ ID NO 26  
<211> LENGTH: 6335  
<212> TYPE: DNA  
<213> ORGANISM: Artificial  
<220> FEATURE:  
<223> OTHER INFORMATION: Synthetic plasmid

<400> SEQUENCE: 26

```
tcgagctcta gattgggaac ccgggtctct cgaattcgag atctccacca tgcacagacc    60
tagacgtcgt ggaactcgtc cacctccact ggcactgctc gctgctctcc tcctggctgc   120
acgtggtgct gatgcagaca tccagatgac ccagtctcca gcctccctgt ctgcatctgt   180
tggagacaga gtcaccatca cttgtcgggc gagtcaggac attagcgatt atttagcctg   240
gtatcagcag aaaccaggga aaattcctag gctcctgatc tatactacat ccactttgca   300 atcagggtc  ccatctcggt tccgtggcag tgggtctggg acagatttca ctctcaccat   360
cagcagcctg cagcctgaag atgttgcaac ttattactgt cagaagtatg acagtgcccc   420
gctcactttc ggcggaggga ccaaggtgga gatcaaacga actgtggctg caccatctgt   480
cttcatcttc ccgccatctg atgagcagtt gaaatctgga actgcctctg ttgtgtgcct   540
gctgaataac ttctatccca gagaggccaa agtacagtgg aaggtggata acgcctccca   600
atcgggtaac tcccaggaga gtgtcacaga gcaggacagc aaggacagca cctacagcct   660
cagcagcacc ctgacgctga gcaaagcaga ctacgagaaa cacaaagtct acgcctgcga   720
agtcacccat cagggcctga gctcgcccgt cacaaagagc ttcaacaggg gagagtgtta   780
ggcggccgct aatcagccat accacatttg tagaggtttt acttgcttta aaaaacctcc   840
cacacctccc cctgaacctg aaacataaaa tgaatgcaat tgttgttgtt aacttgttta   900
ttgcagctta taatggttac aaataaagca atagcatcac aaatttcaca ataaagcat    960 tttttcact  gcattctagt tgtggtttgt ccaaactcat caatgtatct tatcatgtct  1020
accggtaggg cccctctctt catgtgagca aaaggccagc aaaaggccag gaaccgtaaa  1080
aaggccgcgt tgctggcgtt tttccatagg ctccgccccc ctgacgagca tcacaaaaat  1140
cgacgctcaa gtcagaggtg gcgaaacccg acaggactat aaagatacca ggcgtttccc  1200
cctggaagct ccctcgtgcg ctctcctgtt ccgaccctgc cgcttaccgg atacctgtcc  1260
gcctttctcc cttcgggaag cgtggcgctt tctcaatgct cacgctgtag gtatctcagt  1320
tcggtgtagg tcgttcgctc caagctgggc tgtgtgcacg aaccccccgt tcagcccgac  1380
cgctgcgcct tatccggtaa ctatcgtctt gagtccaacc cggtaagaca cgacttatcg  1440
ccactggcag cagccactgg taacaggatt agcagagcga ggtatgtagg cggtgctaca  1500
gagttcttga agtggtggcc taactacggc tacactagaa ggacagtatt tggtatctgc  1560
gctctgctga agccagttac cttcggaaaa agagttggta gctcttgatc cggcaaacaa  1620
accaccgctg gtagcggtgg ttttttgtt  tgcaagcagc agattacgcg cagaaaaaaa  1680
ggatctcaag aagatccttt gatcttttct acggggtctg acgctcagtg aacgaaaac   1740
```

```
tcacgttaag ggattttggt catgggcgcg ggcatgagat tatcaaaaag gatcttcacc      1800
tagatccttt taaattaaaa atgaagtttt aaatcaatct aaagtatata tgagtaaact      1860
tggtctgaca gttaccaatg cttaatcagt gaggcaccta tctcagcgat ctgtctattt      1920
cgttcatcca tagttgcctg actcccgtc gtgtagataa ctacgatacg ggagggctta      1980
ccatctggcc ccagtgctgc aatgataccg cgagacccac gctcaccggc tccagattta      2040
tcagcaataa accagccagc cggaagggcc gagcgcagaa gtggtcctgc aactttatcc      2100
gcctccatcc agtctattaa ttgttgccgg gaagctagag taagtagttc gccagttaat      2160
agtttgcgca acgttgttgc cattgctaca ggcatcgtgg tgtcacgctc gtcgtttggt      2220
atggcttcat tcagctccgg ttcccaacga tcaaggcgag ttacatgatc ccccatgttg      2280
tgcaaaaaag cggttagctc cttcggtcct ccgatcgttg tcagaagtaa gttggccgca      2340
gtgttatcac tcatggttat ggcagcactg cataattctc ttactgtcat gccatccgta      2400
agatgctttt ctgtgactgg tgagtactca accaagtcat tctgagaata gtgtatgcgg      2460
cgaccgagtt gctcttgccc ggcgtcaata cgggataata ccgcgccaca tagcagaact      2520
ttaaaagtgc tcatcattgg aaaacgttct cggggcgaaa actctcaag gatcttaccg      2580 ctgttgagat ccagttcgat gtaacccact cgtgcaccca actgatcttc agcatctttt      2640
actttcacca gcgtttctgg gtgagcaaaa acaggaaggc aaaatgccgc aaaaaaggga      2700 ataaggggcga cacggaaatg ttgaatactc atactcttcc ttttcaata ttattgaagc      2760 atttatcagg gttattgtct catgagcgga tacatatttg aatgtattta gaaaaataaa      2820
caaatagggg ttccgcgcac atttccccga aaagtgccac ctgacgtcag gtacacttag      2880
gcgcgccatt agagttcctg caggctacat ggtaccaagc ctaggcctcc aaaaaagcct      2940
cctcactact tctggaatag ctcagaggca gaggcggcct cggcctctgc ataaataaaa      3000
aaaattagtc agccatgggg cggagaatgg gcggaactgg gcggagttag gggcgggatg      3060
ggcggagtta ggggcgggac tatggttgct gactaattga gatgcatgct ttgcatactt      3120
ctgcctgctg gggagcctgg ggactttcca cacctggttg ctgactaatt gagatgcatg      3180
ctttgcatac ttctgcctgc tggggagcct ggggactttc cacaccggat ccaccatgga      3240
tagatccgga aagcctgaac tcaccgcgac gtctgtcgag aagtttctga tcgaaaagtt      3300
cgacagcgtc tccgacctga tgcagctctc ggagggcgaa gaatctcgtg ctttcagctt      3360
cgatgtagga gggcgtggat atgtcctgcg ggtaaatagc tgcgccgatg gtttctacaa      3420
agatcgttat gtttatcggc actttgcatc ggccgcgctc ccgattccgg aagtgcttga      3480
cattggggag ttcagcgaga gcctgaccta ttgcatctcc cgccgtgcac agggtgtcac      3540
gttgcaagac ctgcctgaaa ccgaactgcc cgctgttctg cagccggtcg cggaggccat      3600
ggatgcgatc gctgcggccg atcttagcca gacgagcggg ttcggcccat tcggaccgca      3660
aggaatcggt caatacacta catggcgtga tttcatatgc gcgattgctg atccccatgt      3720
gtatcactgg caaactgtga tggacgacac cgtcagtgcg tccgtcgcgc aggctctcga      3780
tgagctgatg ctttgggccg aggactgccc cgaagtccgg cacctcgtgc acgcggattt      3840
cggctccaac aatgtcctga cggacaatgg ccgcataaca gcggtcattg actggagcga      3900
ggcgatgttc ggggattccc aatacgaggt cgccaacatc ttcttctgga ggccgtggtt      3960
ggcttgtatg gagcagcaga cgcgctactt cgagcggagg catccggagc ttgcaggatc      4020
gccgcggctc cgggcgtata tgctccgcat tggtcttgac caactctatc agagcttggt      4080
tgacggcaat ttcgatgatg cagcttgggc gcagggtcga tgcgacgcaa tcgtccgatc      4140
```

```
cggagccggg actgtcgggc gtacacaaat cgcccgcaga agcgcggccg tctggaccga   4200
tggctgtgta gaagtactcg ccgatagtgg aaaccgacgc cccagcactc gtccgagggc   4260
aaaggaatag acgcgtgctg taagtctgca gaaattgatg atctattaaa caataaagat   4320
gtccactaaa atggaagttt ttcctgtcat actttgttaa gaagggtgag aacagagtac   4380
ctacattttg aatggaagga ttggagctac gggggtgggg gtggggtggg attagataaa   4440
tgcctgctct ttactgaagg ctctttacta ttgcttatg ataatgtttc atagttggat    4500
atcataattt aaacaagcaa aaccaaatta agggccagct cattcctccc actcatgatc   4560
tatgatccta tagatctctc gtgcagctgg ggctctaggg ggtatcccca cgcgccctgt   4620
agcggcgcat taagcgcggc gggtgtggtg gttacgcgca gcgtgaccgc tacacttgcc   4680
agcgccctag cgcccgctcc tttcgctttc ttcccttcct ttctcgccac gttcgccggc   4740
tttccccgtc aagctctaaa tcggggctc  cctttagggt tccgatttag tgctttacgg    4800
cacctcgacc ccaaaaaact tgattagggt gatggttcac gtagtgggcc atcgccctga   4860
tagacggttt ttcgcccttt gacgttggag tccacgttct ttaatagtgg actcttgttc   4920
caaactggaa caacactcaa ccctatctcg gtctattctt ttgatttata agggattttg   4980
ccgatttcgg cctattggtt aaaaaatgag ctgatttaac aaaaatttaa cgcgaattaa   5040
ttctgtggaa tgtgtgtcag ttagtcgcga tgtgtgacta gttagttatt aatagtaatc   5100
aattacgggg tcattagttc atagcccata tatggagttc cgcgttacat aacttacggt   5160
aaatggcccg cctggctgac cgcccaacga ccccgccca  ttgacgtcaa taatgacgta   5220
tgttcccata gtaacgccaa tagggacttt ccattgacgt caatgggtgg agtatttacg   5280
gtaaactgcc cacttggcag tacatcaagt gtatcatatg ccaagtacgc cccctattga   5340
cgtcaatgac ggtaaatggc ccgcctggca ttatgcccag tacatgacct tatgggactt   5400
tcctacttgg cagtacatct acgtattagt catcgctatt accatggtga tgcggttttg   5460
gcagtacatc aatgggcgtg gatagcggtt tgactcacgg ggatttccaa gtctccaccc   5520
cattgacgtc aatgggagtt tgttttggca ccaaaatcaa cgggactttc caaaatgtcg   5580
taacaactcc gccccattga cgcaaatggg cggtaggcgt gtacggtggg aggtctatat   5640
aagcagagct catgatagaa gcactctact attcgtcgac cgatcctgag aacttcaggg   5700
tgagtttggg gacccttgat tgttcttcct ttttcgctat tgtaaaattc atgttatatg   5760
gagggggcaa agttttcagg gtgttgttta gaatgggaag atgtcccttg tatcaccatg   5820
gaccctcatg ataattttgt ttctttcact ttctactctg ttgacaacca ttgtctcctc   5880 ttatttctt  ttcattttct gtaactttt   cgttaaactt agcttgcat ttgtaacgaa    5940 tttttaaatt cactttgtt  tatttgtcag attgtaagta cttctctaa tcactttttt    6000 ttcaaggcaa tcagggtata ttatattgta cttcagcaca gttttagaga acaattgtta   6060
taattaaatg ataaggtaga atatttctgc atataaattc tggctggcgt ggaaatattc   6120
ttattggtag aaacaactac accctggtca tcatcctgcc tttctcttta tggttacaat   6180
gatatacact gtttgagatg aggataaaat actctgagtc caaaccgggc ccctctgcta   6240
accatgttca tgccttcttc tctttcctac agctcctggg caacgtgctg gttgttgtgc   6300
tgtctcatca ttttggcaaa gaattaagct tatac                              6335
```

<210> SEQ ID NO 27
<211> LENGTH: 452
<212> TYPE: PRT

<213> ORGANISM: Homo sapiens

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly Lys
        450

<210> SEQ ID NO 28
<211> LENGTH: 112
<212> TYPE: PRT
<213> ORGANISM: Homo sapiens

<400> SEQUENCE: 28

Glu Ser Gly Gly Gly Leu Val Gln Pro Gly Ser Leu Arg Leu Ser
1               5                  10                  15

Cys Ala Ala Ser Gly Phe Thr Phe Ser Ser Tyr Asp Ile His Trp Val
            20                  25                  30

Arg Gln Ala Thr Gly Lys Gly Leu Glu Trp Val Ser Ala Ile Gly Pro
        35                  40                  45

Ala Gly Asp Thr Tyr Tyr Pro Gly Ser Val Lys Gly Arg Phe Thr Ile
    50                  55                  60

Ser Arg Glu Asn Ala Lys Asn Ser Leu Tyr Leu Gln Met Asn Ser Leu
65                  70                  75                  80

Arg Ala Gly Asp Thr Ala Val Tyr Tyr Cys Ala Arg Gly Leu Ile Thr
                85                  90                  95

Phe Gly Gly Leu Ile Ala Pro Phe Asp Tyr Trp Gly Gln Gly Thr Leu
            100                 105                 110

<210> SEQ ID NO 29
<211> LENGTH: 214
<212> TYPE: PRT
<213> ORGANISM: Homo sapiens

<400> SEQUENCE: 29

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Asn Ser Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 30
<211> LENGTH: 107
<212> TYPE: PRT
<213> ORGANISM: Homo sapiens

<400> SEQUENCE: 30

Ile Val Leu Thr Gln Ser Pro Gly Thr Leu Ser Leu Ser Pro Gly Glu
1               5                   10                  15
Arg Ala Thr Leu Ser Cys Arg Ala Ser Gln Ser Val Ser Ser Thr Tyr
            20                  25                  30
Leu Ala Trp Tyr Gln Gln Lys Pro Gly Gln Ala Pro Arg Leu Leu Ile
        35                  40                  45
Tyr Gly Ala Ser Ser Arg Ala Thr Gly Ile Pro Asp Arg Phe Ser Gly
    50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys Gln His Tyr Asp Asn Ser Gln Thr
                85                  90                  95
Phe Gly Gln Gly Thr Lys Val Glu Ile Lys Arg
            100                 105

<210> SEQ ID NO 31
<211> LENGTH: 2986
<212> TYPE: DNA
<213> ORGANISM: Artificial
<220> FEATURE:
<223> OTHER INFORMATION: Synthetic construct

<400> SEQUENCE: 31
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg taggcgtgt      540
acggtgggag gtctatataa gcagagctca tgatagaagc actctactat tcgtcgaccg     600
atcctgagaa cttcagggtg agtttgggga cccttgattg ttctttcttt ttcgctattg     660
taaaattcat gttatatgga gggggcaaag ttttcagggt gttgtttaga atgggaagat     720
gtcccttgta tcaccatgga ccctcatgat aattttgttt ctttcacttt ctactctgtt     780
gacaaccatt gtctcctctt attttctttt cattttctgt aacttttcg ttaaacttta     840
```

```
gcttgcattt gtaacgaatt tttaaattca ctttttgttta tttgtcagat tgtaagtact    900
ttctctaatc actttttttt caaggcaatc agggtatatt atattgtact tcagcacagt    960
tttagagaac aattgttata attaaatgat aaggtagaat atttctgcat ataaattctg   1020
gctggcgtgg aaatattctt attggtagaa acaactacac cctggtcatc atcctgcctt   1080
tctctttatg gttacaatga tatacactgt ttgagatgag gataaaatac tctgagtcca   1140
aaccgggccc ctctgctaac catgttcatg ccttcttctc tttcctacag ctcctgggca   1200
acgtgctggt tgttgtgctg tctcatcatt ttggcaaaga attaagctta tactcgagct   1260
ctagattggg aacccgggtc tctcgaattc gagatctcca ccatgcacag acctagacgt   1320
cgtggaactc gtccacctcc actggcactg ctcgctgctc tcctcctggc tgcacgtggt   1380
gctgatgcag aggtgcagct ggtggagtct gggggaggct tggtacagcc ggggggtcc    1440
ctgagactct cctgtgcagc ctctggattc accttcagta gctacgacat acactgggtc   1500
cgtcaagcta caggaaaagg tctggagtgg gtctcagcta ttggtcctgc tggtgacaca   1560
tactatccag gctccgtgaa gggccgattc accatctcca gagaaaatgc caagaactcc   1620
ttgtatcttc aaatgaacag cctgagagcc ggggacacgg ctgtgtatta ctgtgcaaga   1680
ggtttgatta cgtttggggg gcttatcgcc ccgtttgact actggggcca gggaaccctg   1740
gtcaccgtct cctcagcctc caccaagggc ccatcggtct tccccctggc acctcctcc    1800
aagagcacct ctgggggcac agcggccctg ggctgcctgg tcaaggacta cttccccgaa   1860
ccggtgacgg tgtcgtggaa ctcaggcgcc ctgaccagcg gcgtgcacac cttcccggct   1920
gtcctacagt cctcaggact ctactccctc agcagcgtgg tgaccgtgcc ctccagcagc   1980
ttgggcaccc agacctacat ctgcaacgtg aatcacaagc ccagcaacac caaggtggac   2040
aagaaagttg agcccaaatc ttgtgacaaa actcacacat gcccaccgtg cccagcacct   2100
gaactcctgg ggggaccgtc agtcttcctc ttccccccaa aacccaagga caccctcatg   2160
atctcccgga cccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca aagccctccc agcccccatc   2400
gagaaaacca tctccaaagc caaagggcag ccccgagaac cacaggtgta caccctgccc   2460
ccatcccggg atgagctgac caagaaccag gtcagcctga cctgcctggt caaaggcttc   2520
tatcccagcg acatcgccgt ggagtgggag agcaatgggc agccggagaa caactacaag   2580
accacgcctc ccgtgctgga ctccgacggc tccttcttcc tctacagcaa gctcaccgtg   2640
gacaagagca ggtggcagca ggggaacgtc ttctcatgct ccgtgatgca tgaggctctg   2700
cacaaccact acacgcagaa gtccctctcc ctgtctccgg gtaaatgagc ggccgctaat   2760
cagccatacc acatttgtag aggttttact tgctttaaaa aacctcccac acctccccct   2820
gaacctgaaa cataaaatga atgcaattgt tgttgttaac ttgtttattg cagcttataa   2880
tggttacaaa taaagcaata gcatcacaaa tttcacaaat aaagcatttt tttcactgca   2940
ttctagttgt ggtttgtcca aactcatcaa tgtatcttat catgtc                  2986
```

<210> SEQ ID NO 32
<211> LENGTH: 7028
<212> TYPE: DNA
<213> ORGANISM: Artificial
<220> FEATURE:
<223> OTHER INFORMATION: Synthetic plasmid

<400> SEQUENCE: 32

```
tcgcgatgtg tgactagtta gttattaata gtaatcaatt acggggtcat tagttcatag      60
cccatatatg gagttccgcg ttacataact tacggtaaat ggcccgcctg gctgaccgcc     120
caacgacccc cgcccattga cgtcaataat gacgtatgtt cccatagtaa cgccaatagg     180
gactttccat tgacgtcaat gggtggagta tttacggtaa actgcccact tggcagtaca     240
tcaagtgtat catatgccaa gtacgccccc tattgacgtc aatgacggta aatggcccgc     300
ctggcattat gcccagtaca tgaccttatg gactttcct acttggcagt acatctacgt      360
attagtcatc gctattacca tggtgatgcg gttttggcag tacatcaatg ggcgtggata     420
gcggtttgac tcacggggat ttccaagtct ccaccccatt gacgtcaatg ggagtttgtt     480
ttggcaccaa aatcaacggg actttccaaa atgtcgtaac aactccgccc cattgacgca     540
aatgggcggt aggcgtgtac ggtgggaggt ctatataagc agagctcatg atagaagcac     600
tctactattc gtcgaccgat cctgagaact tcagggtgag tttggggacc cttgattgtt     660
ctttcttttt cgctattgta aaattcatgt tatatggagg gggcaaagtt ttcagggtgt     720
tgtttagaat gggaagatgt cccttgtatc accatggacc ctcatgataa ttttgtttct     780
ttcactttct actctgttga caaccattgt ctcctcttat tttcttttca ttttctgtaa     840
cttttttcgtt aaactttagc ttgcatttgt aacgaatttt taaattcact tttgtttatt    900
tgtcagattg taagtacttt ctctaatcac ttttttttca aggcaatcag ggtatattat     960
attgtacttc agcacagttt tagagaacaa ttgttataat taaatgataa ggtagaatat    1020
ttctgcatat aaattctggc tggcgtggaa atattcttat tggtagaaac aactacaccc    1080
tggtcatcat cctgcctttc tctttatggt tacaatgata tacactgttt gagatgagga    1140
taaaatactc tgagtccaaa ccgggcccct ctgctaacca tgttcatgcc ttcttctctt    1200
tcctacagct cctgggcaac gtgctggttg ttgtgctgtc tcatcatttt ggcaaagaat    1260
taagcttata ctcgagctct agattgggaa cccgggtctc tcgaattcga gatctccacc    1320
atgcacagac ctagacgtcg tggaactcgt ccacctccac tggcactgct cgctgctctc    1380
ctcctggctg cacgtggtgc tgatgcagag gtgcagctgg tggagtctgg gggaggcttg    1440
gtacagccgg gggggtccct gagactctcc tgtgcagcct ctggattcac cttcagtagc    1500
tacgacatac actgggtccg tcaagctaca ggaaaaggtc tggagtgggt ctcagctatt    1560
ggtcctgctg gtgacacata ctatccaggc tccgtgaagg gccgattcac catctccaga    1620
gaaaatgcca agaactcctt gtatcttcaa atgaacagcc tgagagccgg gacacggct     1680
gtgtattact gtgcaagagg tttgattacg tttgggggc ttatcgcccc gtttgactac     1740
tggggccagg gaaccctggt caccgtctcc tcagcctcca ccaagggccc atcggtcttc    1800
cccctggcac cctcctccaa gagcacctct ggggcacag cggccctggg ctgcctggtc     1860
aaggactact ccccgaacc ggtgacggtg tcgtggaact caggcgccct gaccagcggc    1920
gtgcacacct tcccggctgt cctacagtcc tcaggactct actccctcag cagcgtggtg    1980
accgtgccct ccagcagctt gggcacccag acctacatct gcaacgtgaa tcacaagccc    2040
agcaacacca aggtggacaa gaaagttgag cccaaatctt gtgacaaaac tcacacatgc    2100
ccaccgtgcc cagcacctga actcctgggg ggaccgtcag tcttcctctt ccccccaaaa    2160
cccaaggaca cctccatgat ctcccggacc cctgaggtca catgcgtggt ggtggacgtg    2220
agccacgaag accctgaggt caagttcaac tggtacgtgg acggcgtgga ggtgcataat    2280
```

```
gccaagacaa agccgcggga ggagcagtac aacagcacgt accgtgtggt cagcgtcctc    2340
accgtcctgc accaggactg gctgaatggc aaggagtaca agtgcaaggt ctccaacaaa    2400
gccctcccag cccccatcga gaaaaccatc tccaaagcca agggcagcc ccgagaacca     2460 caggtgtaca ccctgccccc atcccgggat gagctgacca agaaccaggt cagcctgacc    2520
tgcctggtca aaggcttcta tcccagcgac atcgccgtgg agtgggagag caatgggcag    2580
ccggagaaca actacaagac cacgcctccc gtgctggact ccgacggctc cttcttcctc    2640
tacagcaagc tcaccgtgga caagagcagg tggcagcagg ggaacgtctt ctcatgctcc    2700
gtgatgcatg aggctctgca caaccactac acgcagaagt ccctctcccct gtctccgggt   2760 aaatgagcgg ccgctaatca gccataccac atttgtagag gttttacttg ctttaaaaaa    2820
cctcccacac ctccccctga acctgaaaca taaaatgaat gcaattgttg ttgttaactt    2880
gtttattgca gcttataatg gttacaaata aagcaatagc atcacaaatt tcacaaataa    2940
agcatttttt tcactgcatt ctagttgtgg tttgtccaaa ctcatcaatg tatcttatca    3000
tgtctaccgg tcctgcaggg cccctctctt catgtgagca aaaggccagc aaaaggccag    3060
gaaccgtaaa aaggccgcgt tgctggcgtt tttccatagg ctccgccccc ctgacgagca    3120
tcacaaaaat cgacgctcaa gtcagaggtg gcgaaacccg acaggactat aaagatacca    3180
ggcgtttccc cctggaagct ccctcgtgcg ctctcctgtt ccgaccctgc cgcttaccgg    3240
atacctgtcc gcctttctcc cttcgggaag cgtggcgctt tctcaatgct cacgctgtag    3300
gtatctcagt tcggtgtagg tcgttcgctc caagctgggc tgtgtgcacg aaccccccgt    3360
tcagcccgac cgctgcgcct tatccggtaa ctatcgtctt gagtccaacc cggtaagaca    3420
cgacttatcg ccactggcag cagccactgg taacaggatt agcagagcga ggtatgtagg    3480
cggtgctaca gagttcttga agtggtggcc taactacggc tacactagaa ggacagtatt    3540
tggtatctgc gctctgctga agccagttac cttcggaaaa agagttggta gctcttgatc    3600
cggcaaacaa accaccgctg gtagcggtgg ttttttttgtt tgcaagcagc agattacgcg    3660
cagaaaaaaa ggatctcaag aagatccttt gatcttttct acggggtctg acgctcagtg    3720
gaacgaaaac tcacgttaag ggattttggt catgggcgcg cctcatactc ctgcaggcat    3780
gagattatca aaaaggatct tcacctagat ccttttaaat taaaaatgaa gttttaaatc    3840
aatctaaagt atatatgagt aaacttggtc tgacagttac caatgcttaa tcagtgaggc    3900
acctatctca gcgatctgtc tatttcgttc atccatagtt gcctgactcc ccgtcgtgta    3960
gataactacg atacgggagg gcttaccatc tggccccagt gctgcaatga taccgcgaga    4020
cccacgctca ccggctccag atttatcagc aataaaccag ccagccggaa gggccgagcg    4080
cagaagtggt cctgcaactt tatccgcctc catccagtct attaattgtt gccgggaagc    4140
tagagtaagt agttcgccag ttaatagttt gcgcaacgtt gttgccattg ctacaggcat    4200
cgtggtgtca cgctcgtcgt ttggtatggc ttcattcagc tccggttccc aacgatcaag    4260
gcgagttaca tgatccccca tgttgtgcaa aaaagcggtt agctccttcg gtcctccgat    4320
cgttgtcaga agtaagttgg ccgcagtgtt atcactcatg gttatggcag cactgcataa    4380
ttctcttact gtcatgccat ccgtaagatg cttttctgtg actggtgagt actcaaccaa    4440
gtcattctga gaatagtgta tgcggcgacc gagttgctct tgcccggcgt caatacggga    4500
taataccgcg ccacatagca gaactttaaa agtgctcatc attggaaaac gttcttcggg    4560
gcgaaaactc tcaaggatct taccgctgtt gagatccagt tcgatgtaac ccactcgtgc    4620
acccaactga tcttcagcat cttttacttt caccagcgtt tctgggtgag caaaaacagg    4680
```

```
aaggcaaaat gccgcaaaaa agggaataag ggcgacacgg aaatgttgaa tactcatact   4740
cttccttttt caatattatt gaagcattta tcagggttat tgtctcatga gcggatacat   4800
atttgaatgt atttagaaaa ataaacaaat aggggttccg cgcacatttc cccgaaaagt   4860
gccacctgac gtcaggtacc aagcctaggc ctccaaaaaa gcctcctcac tacttctgga   4920
atagctcaga ggcagaggcg gcctcggcct ctgcataaat aaaaaaaatt agtcagccat   4980
ggggcggaga atgggcggaa ctgggcgagt taggggcgg gatgggcgga gttaggggcg    5040
ggactatggt tgctgactaa ttgagatgca tgctttgcat acttctgcct gctggggagc   5100
ctggggactt tccacacctg gttgctgact aattgagatg catgctttgc atacttctgc   5160
ctgctgggga gcctggggac tttccacacc ggatccacca tggatagatc cggaaagcct   5220
gaactcaccg cgacgtctgt cgagaagttt ctgatcgaaa agttcgacag cgtctccgac   5280
ctgatgcagc tctcggaggg cgaagaatct cgtgctttca gcttcgatgt aggagggcgt   5340
ggatatgtcc tgcgggtaaa tagctgcgcc gatggtttct acaaagatcg ttatgtttat   5400
cggcactttg catcggccgc gctcccgatt ccggaagtgc ttgacattgg ggagttcagc   5460
gagagcctga cctattgcat ctcccgccgt gcacagggtg tcacgttgca agacctgcct   5520
gaaaccgaac tgcccgctgt tctgcagccg gtcgcggagg ccatggatgc gatcgctgcg   5580
gccgatctta gccagacgag cgggttcggc ccattcggac cgcaaggaat cggtcaatac   5640
actacatggc gtgatttcat atgcgcgatt gctgatcccc atgtgtatca ctggcaaact   5700 gtgatgacg acaccgtcag tgcgtccgtc gcgcaggctc tcgatgagct gatgctttgg    5760
gccgaggact gccccgaagt ccggcacctc gtgcacgcgg atttcggctc caacaatgtc   5820 ctgacgaca atggccgcat aacagcggtc attgactgga gcgaggcgat gttcggggat   5880
tcccaatacg aggtcgccaa catcttcttc tggaggccgt ggttggcttg tatggagcag   5940
cagacgcgct acttcgagcg gaggcatccg gagcttgcag atcgccgcg gctccgggcg    6000 tatatgctcc gcattggtct tgaccaactc tatcagagct tggttgacgg caatttcgat   6060
gatgcagctt gggcgcaggg tcgatgcgac gcaatcgtcc gatccggagc cgggactgtc   6120
gggcgtacac aaatcgcccg cagaagcgcg gccgtctgga ccgatggctg tgtagaagta   6180
ctcgccgata gtggaaaccg acgccccagc actcgtccga gggcaaagga atagacgcgt   6240
gctgtaagtc tgcagaaatt gatgatctat taaacaataa agatgtccac taaaatggaa   6300 gttttttcctg tcatactttg ttaagaaggg tgagaacaga gtacctacat tttgaatgga   6360
aggattggag ctacggggt gggggtgggg tgggattaga taaatgcctg ctctttactg    6420
aaggctcttt actattgctt tatgataatg tttcatagtt ggatatcata atttaaacaa   6480
gcaaaaccaa attaagggcc agctcattcc tcccactcat gatctatgga tctatagatc   6540
tctcgtgcag ctggggctct agggggtatc cccacgcgcc ctgtagcggc gcattaagcg   6600
cggcgggtgt ggtggttacg cgcagcgtga ccgctacact tgccagcgcc ctagcgcccg   6660
ctcctttcgc tttcttccct tcctttctcg ccacgttcgc cggctttccc cgtcaagctc   6720
taaatcgggg gctcccttta gggttccgat ttagtgcttt acggcacctc gaccccaaaa   6780
aacttgatta gggtgatggt tcacgtagtg gccatcgcc ctgatagacg ttttttcgcc    6840
ctttgacgtt ggagtccacg ttctttaata gtggactctt gttccaaact ggaacaacac   6900
tcaaccctat ctcggtctat tcttttgatt tataagggat tttgccgatt tcggcctatt   6960
ggttaaaaaa tgagctgatt taacaaaaat ttaacgcgaa ttaattctgt ggaatgtgtg   7020
```

```
tcagttag                                                             7028

<210> SEQ ID NO 33
<211> LENGTH: 2272
<212> TYPE: DNA
<213> ORGANISM: Artificial
<220> FEATURE:
<223> OTHER INFORMATION: Synthetic construct

<400> SEQUENCE: 33
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctca tgatagaagc actctactat tcgtcgaccg     600
atcctgagaa cttcagggtg agtttgggga cccttgattg ttctttcttt ttcgctattg     660
taaaattcat gttatatgga gggggcaaag ttttcagggt gttgtttaga atgggaagat     720
gtcccttgta tcaccatgga ccctcatgat aattttgttt ctttcacttt ctactctgtt     780
gacaaccatt gtctcctctt attttctttt cattttctgt aacttttttcg ttaaacttta     840 gcttgcattt gtaacgaatt tttaaattca cttttgttta tttgtcagat tgtaagtact     900
ttctctaatc actttttttt caaggcaatc agggtatatt atattgtact tcagcacagt     960
tttagagaac aattgttata attaaatgat aaggtagaat attctgcat ataaattctg     1020 gctggcgtgg aaatattctt attggtagaa acaactacac cctggtcatc atcctgcctt    1080
tctctttatg gttacaatga tatacactgt ttgagatgag gataaaatac tctgagtcca    1140
aaccgggccc ctctgctaac catgttcatg ccttcttctc tttcctacag ctcctgggca    1200
acgtgctggt tgttgtgctg tctcatcatt ttggcaaaga attaagctta tactcgagct    1260
ctagattggg aacccgggtc tctcgaattc gagatctcca ccatgcacag acctagacgt    1320
cgtggaactc gtccacctcc actggcactg ctcgctgctc tcctcctggc tgcacgtggt    1380
gctgatgcag aaattgtgtt gacgcagtct ccaggcaccc tgtctttgtc tccagggaa    1440 agagccaccc tctcctgcag ggccagtcag agtgttagca gcacctactt agcctggtac    1500
cagcagaaac ctggccaggc tcccaggctc ctcatctatg gtgcatccag cagggccact    1560
ggcatcccag acaggttcag tggcagtggg tctgggacag acttcactct caccatcagc    1620
agactggagc ctgaagattt tgcagtgtat tactgtcagc attatgataa ctcacaaacg    1680
ttcggccaag ggaccaaggt ggagatcaaa cgaactgtgg ctgcaccatc tgtcttcatc    1740
ttcccgccat ctgatgagca gttgaaatct ggaactgcct ctgttgtgtg cctgctgaat    1800
aacttctatc ccagagaggc caaagtacag tggaaggtgg ataacgccct ccaatcgggt    1860
aactcccagg agagtgtcac agagcaggac agcaaggaca gcacctacag cctcagcagc    1920
accctgacgc tgagcaaagc agactacgag aaacacaaag tctacgcctg cgaagtcacc    1980
catcagggcc tgagctcgcc cgtcacaaag agcttcaaca ggggagagtg ttaggcggcc    2040
```

```
gctaatcagc cataccacat ttgtagaggt tttacttgct ttaaaaaacc tcccacacct    2100
ccccctgaac ctgaaacata aaatgaatgc aattgttgtt gttaacttgt ttattgcagc    2160
ttataatggt tacaaataaa gcaatagcat cacaaatttc acaaataaag catttttttc    2220
actgcattct agttgtggtt tgtccaaact catcaatgta tcttatcatg tc            2272
```

<210> SEQ ID NO 34
<211> LENGTH: 6335
<212> TYPE: DNA
<213> ORGANISM: Artificial
<220> FEATURE:
<223> OTHER INFORMATION: Synthetic plasmid

<400> SEQUENCE: 34

```
tcgagctcta gattgggaac ccgggtctct cgaattcgag atctccacca tgcacagacc      60
tagacgtcgt ggaactcgtc cacctccact ggcactgctc gctgctctcc tcctggctgc     120
acgtggtgct gatgcagaaa ttgtgttgac gcagtctcca ggcaccctgt ctttgtctcc     180
aggggaaaga gccacctctc ctgcagggc cagtcagagt gttagcagca cctacttagc      240
ctggtaccag cagaaacctg gccaggctcc caggctcctc atctatggtg catccagcag     300
ggccactggc atcccagaca ggttcagtgg cagtgggtct gggacagact tcactctcac     360
catcagcaga ctggagcctg aagattttgc agtgtattac tgtcagcatt atgataactc     420
acaaacgttc ggccaaggga ccaaggtgga gatcaaacga actgtggctg caccatctgt     480
cttcatcttc ccgccatctg atgagcagtt gaaatctgga actgcctctg ttgtgtgcct     540
gctgaataac ttctatccca gagaggccaa agtacagtgg aaggtggata cgccctcca      600 atcgggtaac tcccaggaga gtgtcacaga gcaggacagc aaggacagca cctacagcct     660
cagcagcacc ctgacgctga gcaaagcaga ctacgagaaa cacaaagtct acgcctgcga     720
agtcacccat caggcctga gctcgcccgt cacaaagagc ttcaacaggg gagagtgtta     780
ggcggccgct aatcagccat accacatttg tagaggtttt acttgcttta aaaaacctcc     840
cacacctccc cctgaacctg aaacataaaa tgaatgcaat tgttgttgtt aacttgttta     900
ttgcagctta atggttac aaataaagca atagcatcac aaatttcaca aataaagcat      960 tttttttcact gcattctagt tgtggtttgt ccaaactcat caatgtatct tatcatgtct    1020
accggtaggg ccccctctctt catgtgagca aaaggccagc aaaaggccag gaaccgtaaa    1080
aaggccgcgt tgctggcgtt tttccatagg ctccgccccc ctgacgagca tcacaaaaat    1140
cgacgctcaa gtcagaggtg gcgaaacccg acaggactat aaagatacca ggcgtttccc    1200
cctggaagct ccctcgtgcg ctctcctgtt ccgaccctgc cgcttaccgg atacctgtcc    1260
gcctttctcc cttcgggaag cgtggcgctt tctcaatgct cacgctgtag gtatctcagt    1320
tcggtgtagg tcgttcgctc caagctgggc tgtgtgcacg aaccccccgt tcagcccgac    1380
cgctgcgcct tatccggtaa ctatcgtctt gagtccaacc cggtaagaca cgacttatcg    1440
ccactggcag cagccactgg taacaggatt agcagagcga ggtatgtagg cggtgctaca    1500
gagttcttga agtggtggcc taactacggc tacactagaa ggacagtatt tggtatctgc    1560
gctctgctga agccagttac cttcggaaaa agagttggta gctcttgatc cggcaaacaa    1620
accaccgctg gtagcggtgg tttttttgtt tgcaagcagc agattacgcg cagaaaaaaa    1680
ggatctcaag aagatccttt gatcttttct acggggtctg acgctcagtg gaacgaaaac    1740
tcacgttaag ggattttggt catgggcgcg ggcatgagat tatcaaaaag gatcttcacc    1800
```

```
tagatccttt taaattaaaa atgaagtttt aaatcaatct aaagtatata tgagtaaact    1860
tggtctgaca gttaccaatg cttaatcagt gaggcaccta tctcagcgat ctgtctattt    1920
cgttcatcca tagttgcctg actccccgtc gtgtagataa ctacgatacg ggagggctta    1980
ccatctggcc ccagtgctgc aatgataccg cgagacccac gctcaccggc tccagattta    2040
tcagcaataa accagccagc cggaagggcc gagcgcagaa gtggtcctgc aactttatcc    2100
gcctccatcc agtctattaa ttgttgccgg gaagctagag taagtagttc gccagttaat    2160
agtttgcgca acgttgttgc cattgctaca ggcatcgtgg tgtcacgctc gtcgtttggt    2220
atggcttcat tcagctccgg ttcccaacga tcaaggcgag ttacatgatc ccccatgttg    2280
tgcaaaaaag cggttagctc cttcggtcct ccgatcgttg tcagaagtaa gttggccgca    2340
gtgttatcac tcatggttat ggcagcactg cataattctc ttactgtcat gccatccgta    2400
agatgctttt ctgtgactgg tgagtactca accaagtcat tctgagaata gtgtatgcgg    2460
cgaccgagtt gctcttgccc ggcgtcaata cgggataata ccgcgccaca tagcagaact    2520
ttaaaagtgc tcatcattgg aaaacgttct tcggggcgaa aactctcaag gatcttaccg    2580
ctgttgagat ccagttcgat gtaacccact cgtgcaccca actgatcttc agcatctttt    2640
actttcacca gcgtttctgg gtgagcaaaa acaggaaggc aaaatgccgc aaaaaaggga    2700 ataaggcga cacggaaatg ttgaatactc atactcttcc ttttcaata ttattgaagc    2760 atttatcagg gttattgtct catgagcgga tacatatttg aatgtattta gaaaataaa    2820 caaataggg ttccgcgcac atttccccga aaagtgccac ctgacgtcag gtacacttag    2880
gcgcgccatt agagttcctg caggctacat ggtaccaagc ctaggcctcc aaaaaagcct    2940
cctcactact tctggaatag ctcagaggca gaggcggcct cggcctctgc ataaataaa    3000 aaaattagtc agccatgggg cggagaatgg gcggaactgg gcggagttag gggcgggatg    3060
ggcggagtta ggggcgggac tatggttgct gactaattga gatgcatgct ttgcatactt    3120
ctgcctgctg gggagcctgg ggactttcca cacctggttg ctgactaatt gagatgcatg    3180
ctttgcatac ttctgcctgc tggggagcct ggggactttc cacaccggat ccaccatgga    3240
tagatccgga aagcctgaac tcaccgcgac gtctgtcgag aagtttctga tcgaaaagtt    3300
cgacagcgtc tccgacctga tgcagctctc ggagggcgaa gaatctcgtg ctttcagctt    3360
cgatgtagga gggcgtggat atgtcctgcg ggtaaatagc tgcgccgatg gtttctacaa    3420
agatcgttat gtttatcggc actttgcatc ggccgcgctc ccgattccgg aagtgcttga    3480
cattggggag ttcagcgaga gcctgaccta ttgcatctcc cgccgtgcac agggtgtcac    3540
gttgcaagac ctgcctgaaa ccgaactgcc cgctgttctg cagccggtcg cggaggccat    3600
ggatgcgatc gctgcggccg atcttagcca gacgagcggg ttcggcccat tcggaccgca    3660
aggaatcggt caatacacta catggcgtga tttcatatgc gcgattgctg atccccatgt    3720
gtatcactgg caaactgtga tggacgacac cgtcagtgcg tccgtcgcgc aggctctcga    3780
tgagctgatg ctttgggccg aggactgccc cgaagtccgg cacctcgtgc acgcggattt    3840
cggctccaac aatgtcctga cggacaatgg ccgcataaca gcggtcattg actggagcga    3900
ggcgatgttc ggggattccc aatacgaggt cgccaacatc ttcttctgga ggccgtggtt    3960
ggcttgtatg gagcagcaga cgcgctactt cgagcggagg catccggagc ttgcaggatc    4020
gccgcggctc cgggcgtata tgctccgcat tggtcttgac caactctatc agagcttggt    4080
tgacggcaat ttcgatgatg cagcttgggc gcagggtcga tgcgacgcaa tcgtccgatc    4140
cggagccggg actgtcgggc gtacacaaat cgcccgcaga agcgcggccg tctggaccga    4200
```

```
tggctgtgta gaagtactcg ccgatagtgg aaaccgacgc cccagcactc gtccgagggc    4260
aaaggaatag acgcgtgctg taagtctgca gaaattgatg atctattaaa caataaagat    4320
gtccactaaa atggaagttt ttcctgtcat actttgttaa gaagggtgag aacagagtac    4380
ctacattttg aatggaagga ttggagctac gggggtgggg gtggggtggg attagataaa    4440
tgcctgctct ttactgaagg ctctttacta ttgctttatg ataatgtttc atagttggat    4500
atcataattt aaacaagcaa aaccaaatta agggccagct cattcctccc actcatgatc    4560
tatggatcta tagatctctc gtgcagctgg ggctctaggg ggtatcccca cgcgccctgt    4620
agcggcgcat taagcgcggc gggtgtggtg gttacgcgca gcgtgaccgc tacacttgcc    4680
agcgccctag cgcccgctcc tttcgctttc ttcccttcct ttctcgccac gttcgccggc    4740
tttccccgtc aagctctaaa tcgggggctc cctttagggt tccgatttag tgctttacgg    4800
cacctcgacc ccaaaaaact tgattagggt gatggttcac gtagtgggcc atcgccctga    4860
tagacggttt ttcgcccttt gacgttggag tccacgttct ttaatagtgg actcttgttc    4920
caaactggaa caacactcaa ccctatctcg gtctattctt ttgatttata agggattttg    4980
ccgatttcgg cctattggtt aaaaaatgag ctgatttaac aaaaatttaa cgcgaattaa    5040
ttctgtggaa tgtgtgtcag ttagtcgcga tgtgtgacta gttagttatt aatagtaatc    5100
aattacgggg tcattagttc atagcccata tatggagttc cgcgttacat aacttacggt    5160
aaatggcccg cctggctgac cgcccaacga ccccgcccca ttgacgtcaa taatgacgta    5220
tgttcccata gtaacgccaa tagggacttt ccattgacgt caatgggtgg agtatttacg    5280
gtaaactgcc cacttggcag tacatcaagt gtatcatatg ccaagtacgc cccctattga    5340
cgtcaatgac ggtaaatggc ccgcctggca ttatgcccag tacatgacct tatgggactt    5400
tcctacttgg cagtacatct acgtattagt catcgctatt accatggtga tgcggttttg    5460
gcagtacatc aatgggcgtg atagcggtt tgactcacgg ggatttccaa gtctccaccc    5520
cattgacgtc aatgggagtt tgttttggca ccaaaatcaa cgggactttc caaaatgtcg    5580
taacaactcc gccccattga cgcaaatggg cggtaggcgt gtacggtggg aggtctatat    5640
aagcagagct catgatagaa gcactctact attcgtcgac cgatcctgag aacttcaggg    5700
tgagtttggg gacccttgat tgttctttct ttttcgctat tgtaaaattc atgttatatg    5760
gagggggcaa agttttcagg gtgttgttta gaatgggaag atgtcccttg tatcaccatg    5820
gaccctcatg ataattttgt ttctttcact ttctactctg ttgacaacca ttgtctcctc    5880
ttattttctt ttcattttct gtaacttttt cgttaaactt tagcttgcat tgtaacgaa    5940 tttttaaatt cacttttgtt tatttgtcag attgtaagta ctttctctaa tcactttttt    6000
ttcaaggcaa tcagggtata ttatattgta cttcagcaca gttttagaga acaattgtta    6060
taattaaatg ataaggtaga atatttctgc atataaattc tggctggcgt ggaaatattc    6120
ttattggtag aaacaactac accctggtca tcatcctgcc tttctcttta tggttacaat    6180
gatatacact gtttgagatg aggataaaat actctgagtc caaaccgggc ccctctgcta    6240
accatgttca tgccttcttc tctttcctac agctcctggg caacgtgctg gttgttgtgc    6300
tgtctcatca ttttggcaaa gaattaagct tatac                              6335
```

<210> SEQ ID NO 35
<211> LENGTH: 449
<212> TYPE: PRT
<213> ORGANISM: Homo sapiens

```
<400> SEQUENCE: 35

Gln Val Gln Leu Gln Gln Ser Gly Ala Gly Leu Leu Lys Pro Ser Glu
1               5                   10                  15

Thr Leu Ser Leu Thr Cys Thr Val Tyr Gly Gly Ser Phe Ser Ile His
            20                  25                  30

His Trp Thr Trp Ile Arg His Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ala Val Thr Ala Ala Asp Thr Ala Val Tyr Tyr Cys Ala
                85                  90                  95

Arg Gly Leu Arg Phe Leu Asp Trp Leu Ser Ser Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415
```

```
Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

Lys

<210> SEQ ID NO 36
<211> LENGTH: 103
<212> TYPE: PRT
<213> ORGANISM: Homo sapiens

<400> SEQUENCE: 36

Gln Ser Gly Ala Gly Leu Leu Lys Pro Ser Glu Thr Leu Ser Leu Thr
1               5                   10                  15

Cys Thr Val Tyr Gly Gly Ser Phe Ser Ile His His Trp Thr Trp Ile
            20                  25                  30

Arg His Pro Pro Gly Lys Gly Leu Glu Trp Ile Gly Glu Ile Asn His
        35                  40                  45

Arg Gly Ser Thr Asn Tyr Asn Pro Ser Leu Lys Ser Arg Val Thr Ile
    50                  55                  60

Ser Ile Asp Thr Ser Lys Asn Gln Phe Ser Leu Lys Leu Ser Ala Val
65                  70                  75                  80

Thr Ala Ala Asp Thr Ala Val Tyr Tyr Cys Ala Arg Gly Leu Arg Phe
                85                  90                  95

Leu Asp Trp Leu Ser Ser Tyr
            100

<210> SEQ ID NO 37
<211> LENGTH: 214
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asp Tyr
            20                  25                  30

Leu Ala Trp Tyr Gln Gln Lys Pro Gly Lys Val Pro Asn Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Thr Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 38
<211> LENGTH: 107
<212> TYPE: PRT
<213> ORGANISM: Homo sapiens

<400> SEQUENCE: 38

Ile Gln Met Thr Gln Ser Pro Ser Ser Leu Ser Ala Ser Val Gly Asp
1               5                   10                  15

Arg Val Thr Ile Thr Cys Arg Ala Ser Gln Gly Ile Ser Asp Tyr Leu
            20                  25                  30

Ala Trp Tyr Gln Gln Lys Pro Gly Lys Val Pro Asn Leu Leu Ile Tyr
        35                  40                  45

Ala Ala Ser Ala Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Asn Tyr Asn Thr Ala Pro Leu Thr
                85                  90                  95

Phe Gly Gly Gly Thr Lys Val Glu Ile Lys Arg
            100                 105

<210> SEQ ID NO 39
<211> LENGTH: 2977
<212> TYPE: DNA
<213> ORGANISM: Artificial
<220> FEATURE:
<223> OTHER INFORMATION: Synthetic construct

<400> SEQUENCE: 39
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacg caaatgggcg gtaggcgtgt    540
acggtgggag gtctatataa gcagagctca tgatagaagc actctactat cgtcgaccg    600 atcctgagaa cttcagggtg agtttgggga cccttgattg ttctttcttt ttcgctattg    660
taaaattcat gttatatgga gggggcaaag ttttcagggt gttgtttaga atgggaagat    720
gtcccttgta tcaccatgga ccctcatgat aattttgttt ctttcacttt ctactctgtt    780
gacaaccatt gtctcctctt attttctttt cattttctgt aacttttttcg ttaaactttta    840 gcttgcattt gtaacgaatt tttaaattca cttttgtttta tttgtcagat tgtaagtact    900
ttctctaatc acttttttt caaggcaatc agggtatatt atattgtact tcagcacagt    960

```
tttagagaac aattgttata attaaatgat aaggtagaat atttctgcat ataaattctg   1020
gctggcgtgg aaatattctt attggtagaa acaactacac cctggtcatc atcctgcctt   1080
tctctttatg gttacaatga tatacactgt ttgagatgag gataaaatac tctgagtcca   1140
aaccgggccc ctctgctaac catgttcatg ccttcttctc tttcctacag ctcctgggca   1200
acgtgctggt tgttgtgctg tctcatcatt ttggcaaaga attaagctta tactcgagct   1260
ctagattggg aacccgggtc tctcgaattc gagatctcca ccatgcacag acctagacgt   1320
cgtggaactc gtccacctcc actggcactg ctcgctgctc tcctcctggc tgcacgtggt   1380
gctgatgcac aggtacagct gcagcagtcg ggcgcaggac tgttgaagcc ttcggagacc   1440
ctgtccctca cctgcactgt ctatggtgga tccttcagta ttcatcactg gacctggatc   1500
cgccatcccc cagggaaggg gctggagtgg attggggaga tcaatcatcg tggaagcacc   1560
aactacaacc cgtccctcaa gagtcgagtc accatatcaa tagacacgtc caagaaccag   1620
ttctccctga gctgagcgc tgtgaccgcc gcggacacgg ctgtatatta ctgtgcgaga   1680
ggcttacgat ttttggactg gttatcgtcc tactttgact actggggcca gggaaccctg   1740
gtcaccgtct cctcagcctc caccaagggc ccatcggtct tccccctggc gccctgctcc   1800
aggagcacct ccgagagcac agccgccctg ggctgcctgg tcaaggacta cttccccgaa   1860
ccggtgacgg tgtcgtggaa ctcaggcgcc ctgaccagcg gcgtgcacac cttcccggct   1920
gtcctacagt cctcaggact ctactccctc agcagcgtgg tgaccgtgcc ctccagcagc   1980
ttgggcacga agacctacac ctgcaacgta gatcacaagc ccagcaacac caaggtggac   2040
aagagagttg agtccaaata tggtccccca tgcccaccct gcccagcacc tgagttcctg   2100
gggggaccat cagtcttcct gttccccca aaacccaagg acactctcat gatctcccgg   2160
acccctgagg tcacgtgcgt ggtggtggac gtgagccagg aagaccccga ggtccagttc   2220
aactggtacg tggatggcgt ggaggtgcat aatgccaaga caaagccgcg ggaggagcag   2280
ttcaacagca cgtaccgtgt ggtcagcgtc ctcaccgtcc tgcaccagga ctggctgaac   2340
ggcaaggagt acaagtgcaa ggtctccaac aaaggcctcc cgtcctccat cgagaaaacc   2400
atctccaaag ccaaagggca gccccgagag ccacaggtgt acaccctgcc cccatcccag   2460
gaggagatga ccaagaacca ggtcagcctg acctgcctgg tcaaaggctt ctaccccagc   2520
gacatcgccg tggagtggga gagcaatggg cagccggaga caactacaa gaccacgcct   2580 cccgtgctgg actccgacgg ctccttcttc ctctacagca ggctcaccgt ggacaagagc   2640
aggtggcagc aggggaatgt cttctcatgc tccgtgatgc atgaggctct gcacaaccac   2700
tacacacaga gtccctctc cctgtctctg ggtaaatgag cggccgctaa tcagccatac   2760
cacatttgta gaggttttac ttgctttaaa aaacctccca cacctccccc tgaacctgaa   2820
acataaaatg aatgcaattg ttgttgttaa cttgtttatt gcagcttata atggttacaa   2880
ataaagcaat agcatcacaa atttcacaaa taaagcattt ttttcactgc attctagttg   2940
tggtttgtcc aaactcatca atgtatctta tcatgtc                           2977
```

<210> SEQ ID NO 40
<211> LENGTH: 7019
<212> TYPE: DNA
<213> ORGANISM: Artificial
<220> FEATURE:
<223> OTHER INFORMATION: Synthetic plasmid

<400> SEQUENCE: 40

```
tcgcgatgtg tgactagtta gttattaata gtaatcaatt acggggtcat tagttcatag    60
cccatatatg gagttccgcg ttacataact tacggtaaat ggcccgcctg gctgaccgcc   120
caacgacccc cgcccattga cgtcaataat gacgtatgtt cccatagtaa cgccaatagg   180
gactttccat tgacgtcaat gggtggagta tttacggtaa actgcccact tggcagtaca   240
tcaagtgtat catatgccaa gtacgcccc tattgacgtc aatgacggta aatggcccgc    300
ctggcattat gcccagtaca tgaccttatg gactttcct acttggcagt acatctacgt    360
attagtcatc gctattacca tggtgatgcg gttttggcag tacatcaatg ggcgtggata   420
gcggtttgac tcacggggat ttccaagtct ccaccccatt gacgtcaatg ggagtttgtt   480
ttggcaccaa aatcaacggg actttccaaa atgtcgtaac aactccgccc cattgacgca   540
aatgggcggt aggcgtgtac ggtgggaggt ctatataagc agagctcatg atagaagcac   600
tctactattc gtcgaccgat cctgagaact tcagggtgag tttggggacc cttgattgtt   660
cttttctttt cgctattgta aaattcatgt tatatggagg gggcaaagtt ttcagggtgt   720
tgtttagaat gggaagatgt cccttgtatc accatgacc ctcatgataa ttttgtttct    780
ttcactttct actctgttga caaccattgt ctcctcttat tttctttca ttttctgtaa    840 cttttcgtt aaactttagc ttgcatttgt aacgaatttt taaattcact tttgtttatt    900
tgtcagattg taagtacttt ctctaatcac tttttttca aggcaatcag ggtatattat    960
attgtacttc agcacagttt tagagaacaa ttgttataat taaatgataa ggtagaatat  1020
ttctgcatat aaattctggc tggcgtggaa atattcttat tggtagaaac aactacaccc  1080
tggtcatcat cctgccttc tctttatggt tacaatgata tacactgttt gagatgagga   1140
taaaatactc tgagtccaaa ccgggcccct ctgctaacca tgttcatgcc ttcttctctt  1200
tcctacagct cctgggcaac gtgctggttg ttgtgctgtc tcatcatttt ggcaaagaat  1260
taagcttata ctcgagctct agattgggaa cccgggtctc tcgaattcga gatctccacc  1320
atgcacagac ctagacgtcg tggaactcgt ccacctccac tggcactgct cgctgctctc  1380
ctcctggctg cacgtggtgc tgatgcacag gtacagctgc agcagtcggg cgcaggactg  1440
ttgaagcctt cggagaccct gtccctcacc tgcactgtct atggtggatc cttcagtatt  1500
catcactgga cctggatccg ccatccccca gggaaggggc tggagtggat tggggagatc  1560
aatcatcgtg gaagcaccaa ctacaacccg tccctcaaga gtcgagtcac catatcaata  1620
gacacgtcca agaaccagtt ctccctgaag ctgagcgctg tgaccgccgc ggacacggct  1680
gtatattact gtgcgagagg cttacgattt ttggactggt tatcgtccta ctttgactac  1740
tggggccagg gaaccctggt caccgtctcc tcagcctcca ccaagggccc atcggtcttc  1800
cccctggcgc cctgctccag gagcacctcc gagagcacag ccgccctggg ctgcctggtc  1860
aaggactact ccccgaacc ggtgacggtg tcgtggaact caggcgccct gaccagcggc   1920
gtgcacacct tcccggctgt cctacagtcc tcaggactct actccctcag cagcgtggtg  1980
accgtgccct ccagcagctt gggcacgaag acctacacct gcaacgtaga tcacaagccc  2040
agcaacacca aggtggacaa gagagttgag tccaaatatg gtcccccatg cccaccctgc  2100
ccagcacctg agttcctggg gggaccatca gtcttcctgt tccccccaaa acccaaggac  2160
actctcatga tctcccggac ccctgaggtc acgtgcgtgg tggtggacgt gagccaggaa  2220
gacccccagg tccagttcaa ctggtacgtg gatggcgtgg aggtgcataa tgccaagaca  2280
aagccgcggg aggagcagtt caacagcacg taccgtgtgg tcagcgtcct caccgtcctg  2340
caccaggact ggctgaacgg caaggagtac aagtgcaagg tctccaacaa aggcctcccg  2400
```

```
tcctccatcg agaaaaccat ctccaaagcc aaagggcagc cccgagagcc acaggtgtac    2460
accctgcccc catcccagga ggagatgacc aagaaccagg tcagcctgac ctgcctggtc    2520
aaaggcttct accccagcga catcgccgtg gagtgggaga gcaatgggca gccggagaac    2580
aactacaaga ccacgcctcc cgtgctggac tccgacggct ccttcttcct ctacagcagg    2640
ctcaccgtgg acaagagcag gtggcaggag gggaatgtct tctcatgctc cgtgatgcat    2700
gaggctctgc acaaccacta cacacagaag tccctctccc tgtctctggg taaatgagcg    2760
gccgctaatc agccatacca catttgtaga ggttttactt gctttaaaaa acctcccaca    2820 cctcccctg  aacctgaaac ataaaatgaa tgcaattgtt gttgttaact tgtttattgc    2880
agcttataat ggttacaaat aaagcaatag catcacaaat ttcacaaata aagcattttt    2940
ttcactgcat tctagttgtg gtttgtccaa actcatcaat gtatcttatc atgtctaccg    3000
gtcctgcagg gcccctctct tcatgtgagc aaaaggccag caaaggcca  ggaaccgtaa    3060 aaaggccgcg ttgctggcgt ttttccatag gctccgcccc cctgacgagc atcacaaaaa    3120
tcgacgctca agtcagaggt ggcgaaaccc gacaggacta taaagatacc aggcgtttcc    3180
ccctggaagc tccctcgtgc gctctcctgt tccgaccctg ccgcttaccg gatacctgtc    3240
cgcctttctc ccttcgggaa gcgtggcgct ttctcaatgc tcacgctgta ggtatctcag    3300
ttcggtgtag gtcgttcgct ccaagctggg ctgtgtgcac gaaccccccg ttcagcccga    3360
ccgctgcgcc ttatccggta actatcgtct tgagtccaac ccggtaagac acgacttatc    3420
gccactggca gcagccactg gtaacaggat tagcagagcg aggtatgtag gcggtgctac    3480
agagttcttg aagtggtggc ctaactacgg ctacactaga aggacagtat ttggtatctg    3540
cgctctgctg aagccagtta ccttcggaaa aagagttggt agctcttgat ccggcaaaca    3600
aaccaccgct ggtagcggtg gtttttttgt ttgcaagcag cagattacgc gcagaaaaaa    3660
aggatctcaa gaagatcctt tgatcttttc tacggggtct gacgctcagt ggaacgaaaa    3720
ctcacgttaa gggattttgg tcatgggcgc gcctcatact cctgcaggca tgagattatc    3780
aaaaaggatc ttcacctaga tccttttaaa ttaaaaatga agttttaaat caatctaaag    3840
tatatatgag taaacttggt ctgacagtta ccaatgctta atcagtgagg cacctatctc    3900
agcgatctgt ctatttcgtt catccatagt tgcctgactc cccgtcgtgt agataactac    3960
gatacgggag ggcttaccat ctggccccag tgctgcaatg ataccgcgag acccacgctc    4020
accggctcca gatttatcag caataaacca gccagccgga agggccgagc gcagaagtgg    4080
tcctgcaact ttatccgcct ccatccagtc tattaattgt tgccgggaag ctagagtaag    4140
tagttcgcca gttaatagtt tgcgcaacgt tgttgccatt gctacaggca tcgtggtgtc    4200
acgctcgtcg tttggtatgg cttcattcag ctccggttcc caacgatcaa ggcgagttac    4260
atgatccccc atgttgtgca aaaaagcggt tagctccttc ggtcctccga tcgttgtcag    4320
aagtaagttg gccgcagtgt tatcactcat ggttatggca gcactgcata attctcttac    4380
tgtcatgcca tccgtaagat gcttttctgt gactggtgag tactcaacca agtcattctg    4440
agaatagtgt atgcggcgac cgagttgctc ttgcccggcg tcaatacggg ataataccgc    4500
gccacatagc agaactttaa aagtgctcat cattggaaaa cgttcttcgg ggcgaaaact    4560
ctcaaggatc ttaccgctgt tgagatccag ttcgatgtaa cccactcgtg cacccaactg    4620
atcttcagca tcttttactt tcaccagcgt ttctgggtga gcaaaaacag gaaggcaaaa    4680
tgccgcaaaa aagggaataa gggcgacacg gaaatgttga atactcatac tcttcctttt    4740
```

```
tcaatattat tgaagcattt atcagggtta ttgtctcatg agcggataca tatttgaatg      4800
tatttagaaa aataaacaaa tagggggttcc gcgcacattt ccccgaaaag tgccacctga     4860
cgtcaggtac caagcctagg cctccaaaaa agcctcctca ctacttctgg aatagctcag     4920
aggcagaggc ggcctcggcc tctgcataaa taaaaaaaat tagtcagcca tggggcggag     4980
aatgggcgga actgggcgga gttaggggcg ggatgggcgg agttaggggc gggactatgg     5040
ttgctgacta attgagatgc atgctttgca tacttctgcc tgctggggag cctggggact     5100
ttccacacct ggttgctgac taattgagat gcatgctttg catacttctg cctgctgggg     5160
agcctgggga ctttccacac cggatccacc atggatagat ccggaaagcc tgaactcacc     5220
gcgacgtctg tcgagaagtt tctgatcgaa aagttcgaca gcgtctccga cctgatgcag     5280
ctctcggagg gcgaagaatc tcgtgctttc agcttcgatg taggagggcg tggatatgtc     5340
ctgcgggtaa atagctgcgc cgatggtttc tacaaagatc gttatgttta tcggcacttt     5400
gcatcggccg cgctcccgat tccggaagtg cttgacattg gggagttcag cgagagcctg     5460
acctattgca tctcccgccg tgcacagggt gtcacgttgc aagacctgcc tgaaaccgaa     5520
ctgcccgctg ttctgcagcc ggtcgcggag gccatggatg cgatcgctgc ggccgatctt     5580
agccagacga gcgggttcgg cccattcgga ccgcaaggaa tcggtcaata cactacatgg     5640
cgtgatttca tatgcgcgat tgctgatccc catgtgtatc actggcaaac tgtgatggac     5700
gacaccgtca gtgcgtccgt cgcgcaggct ctcgatgagc tgatgcttg ggccgaggac     5760 tgccccgaag tccggcacct cgtgcacgcg gatttcggct ccaacaatgt cctgacggac     5820
aatgccgcca taacagcggt cattgactgg agcgaggcga tgttcgggga ttcccaatac     5880
gaggtcgcca acatcttctt ctggaggccg tggttggctt gtatggagca gcagacgcgc     5940
tacttcgagc ggaggcatcc ggagcttgca ggatcgccgc ggctccgggc gtatatgctc     6000
cgcattggtc ttgaccaact ctatcagagc ttggttgacg gcaatttcga tgatgcagct     6060
tgggcgcagg tcgatgcgga cgcaatcgtc cgatccggag ccgggactgt cgggcgtaca     6120
caaatcgccc gcagaagcgc ggccgtctgg accgatggct gtgtagaagt actcgccgat     6180
agtggaaacc gacgccccag cactcgtccg agggcaaagg aatagacgcg tgctgtaagt     6240
ctgcagaaat tgatgatcta ttaaacaata aagatgtcca ctaaaatgga agttttttcct    6300 gtcatacttt gttaagaagg gtgagaacag agtacctaca ttttgaatgg aaggattgga    6360
gctacggggg tgggggtggg gtgggattag ataaatgcct gctctttact gaaggctctt    6420
tactattgct ttatgataat gtttcatagt tggatatcat aatttaaaca agcaaaacca    6480
aattaagggc cagctcattc ctcccactca tgatctatgg atctatagat ctctcgtgca    6540 gctgggctc taggggtat cccacgcgc cctgtagcgg cgcattaagc gcggcgggtg        6600
tggtggttac gcgcagcgtg accgctacac ttgccagcgc cctagcgccc gctcctttcg    6660
ctttcttccc ttcctttctc gccacgttcg ccggctttcc ccgtcaagct ctaaatcggg    6720
ggctcccttt agggttccga tttagtgctt tacggcacct cgaccccaaa aaacttgatt    6780
agggtgatgg ttcacgtagt gggccatcgc cctgatagac ggttttttcgc cctttgacgt    6840 tggagtccac gttctttaat agtggactct tgttccaaac tggaacaaca ctcaacccta    6900
tctcggtcta ttcttttgat ttataaggga ttttgccgat ttcggcctat tggttaaaaa    6960
atgagctgat ttaacaaaaa tttaacgcga attaattctg tggaatgtgt gtcagttag     7019
```

<210> SEQ ID NO 41
<211> LENGTH: 2272

<212> TYPE: DNA
<213> ORGANISM: Artificial
<220> FEATURE:
<223> OTHER INFORMATION: Synthetic construct

<400> SEQUENCE: 41

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtgggag gtctatataa gcagagctca tgatagaagc actctactat cgtcgaccg   600
atcctgagaa cttcagggtg agtttgggga cccttgattg ttctttcttt ttcgctattg   660
taaaattcat gttatatgga gggggcaaag ttttcagggt gttgtttaga atgggaagat   720
gtcccttgta tcaccatgga ccctcatgat aattttgttt ctttcacttt ctactctgtt   780
gacaaccatt gtctcctctt attttctttt cattttctgt aacttttttcg ttaaacttta   840
gcttgcattt gtaacgaatt tttaaattca cttttgttta tttgtcagat tgtaagtact   900
ttctctaatc actttttttt caaggcaatc agggtatatt atattgtact tcagcacagt   960
tttagagaac aattgttata attaaatgat aaggtagaat atttctgcat ataaattctg  1020
gctggcgtgg aaatattctt attggtagaa acaactacac cctggtcatc atcctgcctt  1080
tctctttatg gttacaatga tatacactgt ttgagatgag gataaaatac tctgagtcca  1140
aaccgggccc ctctgctaac catgttcatg ccttcttctc tttcctacag ctcctgggca  1200
acgtgctggt tgttgtgctg tctcatcatt ttggcaaaga attaagctta tactcgagct  1260
ctagattggg aacccgggtc tctcgaattc gagatctcca ccatgcacag acctagacgt  1320
cgtggaactc gtccacctcc actggcactg ctcgctgctc tcctcctggc tgcacgtggt  1380
gctgatgcag acatccagat gacccagtct ccatcctccc tgtctgcatc tgtaggagac  1440
agagtcacca tcacttgccg ggcgagtcag ggcattagcg attatttagc ctggtatcag  1500
cagaaaccag ggaaagttcc taacctcctg atctatgctg cgtccgcttt acaatcaggg  1560
gtcccatctc gtttcagtgg cagtggatct gggacagatt tcactctcac catcagcagc  1620
ctgcagcctg aggatgttgc aacttattac tgtcaaaatt ataacactgc ccgctcact   1680
ttcggcgggg ggaccaaggt ggaaatcaaa cgaactgtgg ctgcaccatc tgtcttcatc  1740
ttcccgccat ctgatgagca gttgaaatct ggaactgcct ctgttgtgtg cctgctgaat  1800
aacttctatc ccagagaggc caaagtacag tggaaggtgg ataacgccct ccaatcgggt  1860
aactcccagg agagtgtcac agagcaggac agcaaggaca gcacctacag cctcagcagc  1920
accctgacgc tgagcaaagc agactacgag aaacacaaag tctacgcctg cgaagtcacc  1980
catcagggcc tgagctcgcc cgtcacaaag agcttcaaca ggggagagtg ttaggcggcc  2040
gctaatcagc cataccacat ttgtagaggt tttacttgct ttaaaaaacc tcccacacct  2100
ccccctgaac ctgaaacata aaatgaatgc aattgttgtt gttaacttgt ttattgcagc  2160
```

```
ttataatggt tacaaataaa gcaatagcat cacaaatttc acaaataaag cattttttc    2220 actgcattct agttgtggtt tgtccaaact catcaatgta tcttatcatg tc            2272

<210> SEQ ID NO 42
<211> LENGTH: 6335
<212> TYPE: DNA
<213> ORGANISM: Artificial
<220> FEATURE:
<223> OTHER INFORMATION: Synthetic plasmid

<400> SEQUENCE: 42
tcgagctcta gattgggaac ccgggtctct cgaattcgag atctccacca tgcacagacc     60
tagacgtcgt ggaactcgtc cacctccact ggcactgctc gctgctctcc tcctggctgc    120
acgtggtgct gatgcagaca tccagatgac ccagtctcca tcctccctgt ctgcatctgt    180
aggagacaga gtcaccatca cttgccgggc gagtcagggc attagcgatt atttagcctg    240
gtatcagcag aaaccaggga agttcctaa cctcctgatc tatgctgcgt ccgctttaca     300
atcaggggtc ccatctcgtt tcagtggcag tggatctggg acagatttca ctctcaccat    360
cagcagcctg cagcctgagg atgttgcaac ttattactgt caaaattata acactgcccc    420
gctcactttc ggcgggggga ccaaggtgga atcaaacga actgtggctg caccatctgt    480
cttcatcttc ccgccatctg atgagcagtt gaaatctgga actgcctctg ttgtgtgcct    540
gctgaataac ttctatccca gagaggccaa agtacagtgg aaggtggata cgccctcca    600 atcgggtaac tcccaggaga gtgtcacaga gcaggacagc aaggacagca cctacagcct    660
cagcagcacc ctgacgctga gcaaagcaga ctacgagaaa cacaaagtct acgcctgcga    720
agtcacccat cagggcctga gctcgcccgt cacaaagagc ttcaacaggg gagagtgtta    780
ggcggccgct aatcagccat accacatttg tagaggtttt acttgcttta aaaaacctcc    840
cacacctccc cctgaacctg aaacataaaa tgaatgcaat tgttgttgtt aacttgttta    900
ttgcagctta taatggttac aaataaagca atagcatcac aaatttcaca aataaagcat    960
ttttttcact gcattctagt tgtggtttgt ccaaactcat caatgtatct tatcatgtct   1020
accggtaggg cccctctctt catgtgagca aaaggccagc aaaaggccag gaaccgtaaa   1080
aaggccgcgt tgctggcgtt tttccatagg ctccgccccc ctgacgagca tcacaaaaat   1140
cgacgctcaa gtcagaggtg gcgaaacccg acaggactat aaagatacca ggcgtttccc   1200
cctggaagct ccctcgtgcg ctctcctgtt ccgaccctgc cgcttaccgg atacctgtcc   1260
gcctttctcc cttcgggaag cgtggcgctt tctcaatgct cacgctgtag gtatctcagt   1320
tcggtgtagg tcgttcgctc caagctgggc tgtgtgcacg aaccccccgt tcagcccgac   1380
cgctgcgcct tatccggtaa ctatcgtctt gagtccaacc cggtaagaca cgacttatcg   1440
ccactggcag cagccactgg taacaggatt agcagagcga ggtatgtagg cggtgctaca   1500
gagttcttga agtggtggcc taactacggc tacactagaa ggacagtatt tggtatctgc   1560
gctctgctga agccagttac cttcggaaaa agagttggta gctcttgatc cggcaaacaa   1620
accaccgctg gtagcggtgg tttttttgtt tgcaagcagc agattacgcg cagaaaaaaa   1680
ggatctcaag aagatccttt gatcttttct acggggtctg acgctcagtg gaacgaaaac   1740
tcacgttaag ggattttggt catgggcgcg gcatgagat tatcaaaaag gatcttcacc    1800
tagatccttt taaattaaaa atgaagtttt aaatcaatct aaagtatata tgagtaaact   1860
tggtctgaca gttaccaatg cttaatcagt gaggcaccta tctcagcgat ctgtctattt   1920
cgttcatcca tagttgcctg actccccgtc gtgtagataa ctacgatacg ggagggctta   1980
```

```
ccatctggcc ccagtgctgc aatgataccg cgagacccac gctcaccggc tccagattta    2040
tcagcaataa accagccagc cggaagggcc gagcgcagaa gtggtcctgc aactttatcc    2100
gcctccatcc agtctattaa ttgttgccgg gaagctagag taagtagttc gccagttaat    2160
agtttgcgca acgttgttgc cattgctaca ggcatcgtgg tgtcacgctc gtcgtttggt    2220
atggcttcat tcagctccgg ttcccaacga tcaaggcgag ttacatgatc ccccatgttg    2280
tgcaaaaaag cggttagctc cttcggtcct ccgatcgttg tcagaagtaa gttggccgca    2340
gtgttatcac tcatggttat ggcagcactg cataattctc ttactgtcat gccatccgta    2400
agatgctttt ctgtgactgg tgagtactca accaagtcat tctgagaata gtgtatgcgg    2460
cgaccgagtt gctcttgccc ggcgtcaata cgggataata ccgcgccaca tagcagaact    2520
ttaaaagtgc tcatcattgg aaaacgttct cggggcgaaa actctcaag gatcttaccg    2580 ctgttgagat ccagttcgat gtaacccact cgtgcaccca actgatcttc agcatctttt    2640
actttcacca gcgtttctgg gtgagcaaaa acaggaaggc aaaatgccgc aaaaaaggga    2700
ataagggcga cacggaaatg ttgaatactc atactcttcc ttttcaata ttattgaagc    2760 atttatcagg gttattgtct catgagcgga tacatatttg aatgtattta gaaaaataaa    2820
caaatagggg ttccgcgcac atttccccga aaagtgccac ctgacgtcag gtacacttag    2880
gcgcgccatt agagttcctg caggctacat ggtaccaagc ctaggcctcc aaaaaagcct    2940
cctcactact tctgaatag ctcagaggca gaggcggcct cggcctctgc ataaataaaa    3000
aaaattagtc agccatgggg cggagaatgg gcggaactgg gcggagttag gggcgggatg    3060
ggcggagtta ggggcgggac tatggttgct gactaattga gatgcatgct ttgcatactt    3120
ctgcctgctg gggagcctgg ggactttcca cacctggttg ctgactaatt gagatgcatg    3180 cttttgcatac ttctgcctgc tggggagcct ggggactttc cacaccggat ccaccatgga    3240
tagatccgga aagcctgaac tcaccgcgac gtctgtcgag aagtttctga tcgaaaagtt    3300
cgacagcgtc tccgacctga tgcagctctc ggagggcgaa gaatctcgtg ctttcagctt    3360
cgatgtagga gggcgtggat atgtcctgcg ggtaaatagc tgcgccgatg gtttctacaa    3420
agatcgttat gtttatcggc actttgcatc ggccgcgctc ccgattccgg aagtgcttga    3480
cattggggag ttcagcgaga gcctgaccta ttgcatctcc cgccgtgcac agggtgtcac    3540
gttgcaagac ctgcctgaaa ccgaactgcc cgctgttctg cagccggtcg cggaggccat    3600
ggatgcgatc gctgcggccg atcttagcca gacgagcggg ttcggcccat tcggaccgca    3660
aggaatcggt caatacacta catggcgtga tttcatatgc gcgattgctg atccccatgt    3720
gtatcactgg caaactgtga tggacgacac cgtcagtgcg tccgtcgcgc aggctctcga    3780
tgagctgatg ctttgggccg aggactgccc cgaagtccgg cacctcgtgc acgcggattt    3840
cggctccaac aatgtcctga cggacaatgg ccgcataaca gcggtcattg actggagcga    3900
ggcgatgttc ggggattccc aatacgaggt cgccaacatc ttcttctgga ggccgtggtt    3960
ggcttgtatg gagcagcaga cgcgctactt cgagcggagg catccggagc ttgcaggatc    4020
gccgcggctc cgggcgtata tgctccgcat tggtcttgac caactctatc agagcttggt    4080
tgacggcaat ttcgatgatg cagcttgggc gcagggtcga tgcgacgcaa tcgtccgatc    4140
cggagccggg actgtcgggc gtacacaaat cgcccgcaga agcgcggccg tctggaccga    4200
tggctgtgta gaagtactcg ccgatagtgg aaaccgacgc cccagcactc gtccgagggc    4260
aaaggaatag acgcgtgctg taagtctgca gaaattgatg atctattaaa caataaagat    4320
```

```
gtccactaaa atggaagttt ttcctgtcat actttgttaa gaagggtgag aacagagtac    4380
ctacattttg aatggaagga ttggagctac gggggtgggg gtggggtggg attagataaa    4440
tgcctgctct ttactgaagg ctctttacta ttgctttatg ataatgtttc atagttggat    4500
atcataattt aaacaagcaa aaccaaatta agggccagct cattcctccc actcatgatc    4560
tatggatcta tagatctctc gtgcagctgg ggctctaggg ggtatcccca cgcgccctgt    4620
agcggcgcat taagcgcggc gggtgtggtg gttacgcgca gcgtgaccgc tacacttgcc    4680
agcgccctag cgcccgctcc tttcgctttc ttcccttcct ttctcgccac gttcgccggc    4740 tttcccccgtc aagctctaaa tcgggggctc cctttagggt tccgatttag tgctttacgg    4800
cacctcgacc ccaaaaaact tgattagggt gatggttcac gtagtgggcc atcgccctga    4860
tagacggttt ttcgcccttt gacgttggag tccacgttct ttaatagtgg actcttgttc    4920
caaactggaa caacactcaa ccctatctcg gtctattctt ttgatttata agggattttg    4980
ccgatttcgg cctattggtt aaaaaatgag ctgatttaac aaaaatttaa cgcgaattaa    5040
ttctgtggaa tgtgtgtcag ttagtcgcga tgtgtgacta gttagttatt aatagtaatc    5100
aattacgggg tcattagttc atagcccata tatggagttc cgcgttacat aacttacggt    5160
aaatggcccg cctggctgac cgcccaacga ccccccgccca ttgacgtcaa taatgacgta    5220
tgttcccata gtaacgccaa tagggacttt ccattgacgt caatgggtgg agtatttacg    5280
gtaaactgcc cacttggcag tacatcaagt gtatcatatg ccaagtacgc ccctattga    5340 cgtcaatgac ggtaaatggc ccgcctggca ttatgcccag tacatgacct tatgggactt    5400
tcctacttgg cagtacatct acgtattagt catcgctatt accatggtga tgcggttttg    5460
gcagtacatc aatgggcgtg gatagcggtt tgactcacgg ggatttccaa gtctccaccc    5520
cattgacgtc aatgggagtt tgttttggca ccaaaatcaa cgggactttc caaaatgtcg    5580
taacaactcc gccccattga cgcaaatggg cggtaggcgt gtacggtggg aggtctatat    5640
aagcagagct catgatagaa gcactctact attcgtcgac cgatcctgag aacttcaggg    5700
tgagtttggg gaccccttgat tgttctttct ttttcgctat tgtaaaattc atgttatatg    5760 gaggggggcaa agttttcagg gtgttgttta gaatgggaag atgtcccttg tatcaccatg    5820
gaccctcatg ataattttgt ttctttcact ttctactctg ttgacaacca ttgtctcctc    5880 ttatttttctt ttcattttct gtaacttttt cgttaaactt tagcttgcat ttgtaacgaa    5940 ttttttaaatt cacttttgtt tatttgtcag attgtaagta ctttctctaa tcactttttt    6000
ttcaaggcaa tcagggtata ttatattgta cttcagcaca gttttagaga acaattgtta    6060
taattaaatg ataaggtaga atatttctgc atataaattc tggctggcgt ggaaatattc    6120
ttattggtag aaacaactac accctggtca tcatcctgcc tttctctta tggttacaat    6180 gatatacact gtttgagatg aggataaaat actctgagtc caaaccgggc ccctctgcta    6240
accatgttca tgccttcttc tctttcctac agctcctggg caacgtgctg gttgttgtgc    6300
tgtctcatca ttttggcaaa gaattaagct tatac                                6335
```

<210> SEQ ID NO 43
<211> LENGTH: 115
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa can be any naturally occurring amino acid

```
<220> FEATURE:
<221> NAME/KEY: MISC_FEATURE
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: Xaa can be any naturally occurring amino acid
<220> FEATURE:
<221> NAME/KEY: MISC_FEATURE
<222> LOCATION: (34)..(35)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Xaa can be any naturally occurring amino acid
<220> FEATURE:
<221> NAME/KEY: MISC_FEATURE
<222> LOCATION: (96)..(96)
<223> OTHER INFORMATION: Xaa can be any naturally occurring amino acid
<220> FEATURE:
<221> NAME/KEY: MISC_FEATURE
<222> LOCATION: (100)..(100)
<223> OTHER INFORMATION: Xaa can be any naturally occurring amino acid
<220> FEATURE:
<221> NAME/KEY: MISC_FEATURE
<222> LOCATION: (111)..(111)
<220> FEATURE:
<221> NAME/KEY: MISC_FEATURE
<222> LOCATION: (114)..(114)
<223> OTHER INFORMATION: Xaa can be any naturally occurring amino acid

<400> SEQUENCE: 43

Xaa Asp Val Trp Gly Gln Gly Thr Thr Val Xaa Val Ser Ser Ala Ser
1               5                   10                  15

Thr Lys Gly Pro Ser Val Phe Pro Leu Ala Pro Xaa Ser Xaa Ser Thr
            20                  25                  30

Ser Xaa Xaa Thr Ala Ala Leu Gly Cys Leu Val Lys Asp Tyr Phe Pro
        35                  40                  45

Glu Pro Val Thr Val Ser Trp Asn Ser Gly Ala Leu Thr Ser Gly Val
50                  55                  60

His Thr Phe Pro Ala Val Leu Gln Ser Ser Gly Leu Tyr Ser Leu Ser
65                  70                  75                  80

Ser Val Val Thr Val Pro Ser Ser Ser Leu Gly Thr Xaa Thr Tyr Xaa
                85                  90                  95

Cys Asn Val Xaa His Lys Pro Ser Asn Thr Lys Val Asp Lys Xaa Val
            100                 105                 110

Glu Xaa Lys
        115

<210> SEQ ID NO 44
<211> LENGTH: 225
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: Xaa can be any naturally occurring amino acid
<220> FEATURE:
<221> NAME/KEY: MISC_FEATURE
```

```
<222> LOCATION: (53)..(53)
<223> OTHER INFORMATION: Xaa can be any naturally occurring amino acid
<220> FEATURE:
<221> NAME/KEY: MISC_FEATURE
<222> LOCATION: (75)..(75)
<223> OTHER INFORMATION: Xaa can be any naturally occurring amino acid
<220> FEATURE:
<221> NAME/KEY: MISC_FEATURE
<222> LOCATION: (106)..(106)
<223> OTHER INFORMATION: Xaa can be any naturally occurring amino acid
<220> FEATURE:
<221> NAME/KEY: MISC_FEATURE
<222> LOCATION: (109)..(110)
<223> OTHER INFORMATION: Xaa can be any naturally occurring amino acid
<220> FEATURE:
<221> NAME/KEY: MISC_FEATURE
<222> LOCATION: (134)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: MISC_FEATURE
<222> LOCATION: (188)..(188)
<223> OTHER INFORMATION: Xaa can be any naturally occurring amino acid
<220> FEATURE:
<221> NAME/KEY: MISC_FEATURE
<222> LOCATION: (198)..(198)
<223> OTHER INFORMATION: Xaa can be any naturally occurring amino acid
<220> FEATURE:
<221> NAME/KEY: MISC_FEATURE
<222> LOCATION: (224)..(224)
<223> OTHER INFORMATION: Xaa can be any naturally occurring amino acid

<400> SEQUENCE: 44

Tyr Gly Pro Pro Cys Pro Pro Cys Pro Ala Pro Glu Xaa Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser Xaa Glu
        35                  40                  45

Asp Pro Glu Val Xaa Phe Asn Trp Tyr Val Asp Gly Val Glu Val His
    50                  55                  60

Asn Ala Lys Thr Lys Pro Arg Glu Glu Xaa Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Xaa Leu Pro Xaa Xaa Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Xaa Xaa Glu Xaa Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Xaa Leu Thr Val Asp
            180                 185                 190

Lys Ser Arg Trp Gln Xaa Gly Asn Val Phe Ser Cys Ser Val Met His
        195                 200                 205

Glu Ala Leu His Asn His Tyr Thr Gln Lys Ser Leu Ser Leu Ser Xaa
    210                 215                 220
```

Gly
225

<210> SEQ ID NO 45
<211> LENGTH: 60
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (21)..(22)
<223> OTHER INFORMATION: Xaa can be any naturally occurring amino acid
<220> FEATURE:
<221> NAME/KEY: MISC_FEATURE
<222> LOCATION: (24)..(27)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (34)..(34)
<223> OTHER INFORMATION: Xaa can be any naturally occurring amino acid
<220> FEATURE:
<221> NAME/KEY: MISC_FEATURE
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: MISC_FEATURE
<222> LOCATION: (54)..(54)
<223> OTHER INFORMATION: Xaa can be any naturally occurring amino acid
<220> FEATURE:
<221> NAME/KEY: MISC_FEATURE
<222> LOCATION: (56)..(56)
<223> OTHER INFORMATION: Xaa can be any naturally occurring amino acid

<400> SEQUENCE: 45

Ser Asp Tyr Leu Ala Trp Tyr Gln Gln Lys Pro Gly Xaa Xaa Pro Xaa
1               5                   10                  15

Leu Leu Ile Tyr Xaa Xaa Ser Xaa Xaa Xaa Xaa Gly Val Pro Xaa Arg
            20                  25                  30

Phe Xaa Gly Ser Gly Ser Gly Thr Asp Phe Thr Leu Thr Ile Ser Xaa
        35                  40                  45

Leu Xaa Pro Glu Asp Xaa Ala Xaa Tyr Tyr Cys Gln
    50                  55                  60

<210> SEQ ID NO 46
<211> LENGTH: 118
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (4)..(4)
<223> OTHER INFORMATION: Xaa can be any naturally occurring amino acid

<400> SEQUENCE: 46

-continued

```
Thr Phe Gly Xaa Gly Thr Lys Val Glu Ile Lys Arg Thr Val Ala Ala
1               5                   10                  15

Pro Ser Val Phe Ile Phe Pro Pro Ser Asp Glu Gln Leu Lys Ser Gly
                20              25                  30

Thr Ala Ser Val Val Cys Leu Leu Asn Asn Phe Tyr Pro Arg Glu Ala
            35              40              45

Lys Val Gln Trp Lys Val Asp Asn Ala Leu Gln Ser Gly Asn Ser Gln
    50              55              60

Glu Ser Val Thr Glu Gln Asp Ser Lys Asp Ser Thr Tyr Ser Leu Ser
65              70              75              80

Ser Thr Leu Thr Leu Ser Lys Ala Asp Tyr Glu Lys His Lys Val Tyr
            85              90              95

Ala Cys Glu Val Thr His Gln Gly Leu Ser Ser Pro Val Thr Lys Ser
            100             105             110

Phe Asn Arg Gly Glu Cys
            115
```

PRODUCTION CELL LINE ENHANCERS

CROSS-REFERENCE TO RELATED APPLICATIONS

This application is (1) a continuation of U.S. patent application Ser. No. 15/201,104 filed 1 Jul. 2016, now U.S. Pat. No. 9,688,751, and which is a divisional of U.S. patent application Ser. No. 14/555,220 filed 26 Nov. 2014, now U.S. Pat. No. 9,382,315, and which is divisional of U.S. patent application Ser. No. 13/904,587 filed 29 May 2013, now U.S. Pat. No. 9,079,954, and which is a continuation-in-part of PCT International Application No. PCT/US2013/043116, filed 29 May 2013, which claims the benefit of U.S. patent application Ser. No. 13/904,587, filed 29 May 2013, now U.S. Pat. No. 9,079,954, and claims the benefit under 35 U.S.C. § 119(e) of U.S. Provisional Patent Application No. 61/652,549 filed 29 May 2012; and (2) a continuation of U.S. patent application Ser. No. 14/737,090, filed on Jun. 11, 2015, which is a continuation of U.S. patent application Ser. No. 13/904,587, filed on May 29, 2013, now U.S. Pat. No. 9,079,954, and which claims the benefit under 35 U.S.C. § 119(e) of U.S. Provisional Patent Application No. 61/652, 549 filed 29 May 2012, each of which is herein specifically incorporated by reference in its entirety.

SEQUENCE LISTING

This application incorporates by reference the sequence listing submitted in computer readable form as file 8150US08_ST25.txt created on May 25, 2017 (206,456 bytes).

FIELD OF THE INVENTION

The invention relates to a cell or cells expressing a recombinant stress-response lectin for the improved production of a multi-subunit protein. Specifically, the invention provides a mammalian cell and cell-line derived therefrom containing a gene encoding EDEM2, and which yields antibody at a high titer.

BACKGROUND OF THE INVENTION

The manufacture of therapeutically active proteins requires proper folding and processing prior to secretion. Proper folding is particularly relevant for proteins, such as antibodies, which consist of multiple subunits that must be properly assembled before secretion. Eukaryotic cells have adapted a system that ensures the proper folding of proteins and the removal of misfolded proteins from the secretory pathway. This system is called the unfolded protein response (UPR) pathway, and it is triggered by the accumulation of misfolded proteins in the endoplasmic reticulum (ER).

An early event of the UPR is the activation of the transcription factor Xbp1, which in turn activates the transcription of endoplasmic reticulum degradation-enhancing alpha-mannosidase-like protein 2 (EDEM2), a member of the endoplasmic reticulum associated degradation (ERAD) pathway. EDEM2 facilitates the removal of misfolded proteins. The ERAD pathway comprises five steps: (1) chaperone-mediated recognition of malformed proteins, (2) targeting of malformed proteins to the retrotranslocation machinery or E3-ligases, which involves EDEM2, (3) initiation of retrotranslocation; (4) ubiquitylation and further retrotranslocation; and (5) proteosome targeting and degradation.

Antibodies are multi-subunit proteins comprising two heavy chains and two light chains, which must be properly folded and associated to form a functional heterotetramer. Any improvement in the efficient and accurate processing of the heavy and light chains to improve the yield or titer of functional antibody heterotetramers is desired.

SUMMARY OF THE INVENTION

Applicants made the surprising discovery that the ectopic expression of EDEM2 in a protein-manufacturing cell line increases the average output of protein per cell, increases the titer of protein secreted into the media, and increases the integrated cell density of production cell lines.

Thus, in one aspect, the invention provides a cell containing (a) a recombinant polynucleotide that encodes a stress-induced mannose-binding lectin and (b) a polynucleotide that encodes a multi-subunit protein. In some embodiments, the stress-induced mannose-binding lectin is an EDEM2 protein, non-limiting examples of which are provided in Table 1, and the multi-subunit protein is an antibody. In other embodiments, the cell also contains a polynucleotide that encodes the active spliced form of XBP1, non-limiting examples of which are provided in Table 2. In one embodiment, the cell is a mammalian cell, such as a CHO cell used in the manufacture of biopharmaceuticals.

In another aspect, the invention provides a cell line derived from the cell described in the previous aspect. By "derived from", what is meant is a population of cells clonally descended from an individual cell and having some select qualities, such as the ability to produce active protein at a given titer, or the ability to proliferate to a particular density. In some embodiments, the cell line, which is derived from a cell harboring the recombinant polynucleotide encoding a stress-induced mannose-binding lectin and a polynucleotide encoding a multi-subunit protein, is capable of producing the multi-subunit protein at a titer of at least 3 grams per liter of media (g/L), at least 5 g/L, or at least 8 g/L. In some embodiments, the cell line can attain an integrated cell density (ICD) that is at least 30% greater, at least 50% greater, at least 60% greater, or at least 90% greater than the integrated cell density attainable by a cell line derived from what is essentially the same cell but without the recombinant polynucleotide encoding the stress-induced mannose-binding lectin.

In another aspect, the invention provides an isolated or recombinant polynucleotide comprising a nucleic acid sequence encoding an EDEM2 protein, which is operably linked (cis) to a constitutive and ubiquitously expressed mammalian promoter, such as the ubiquitin C promoter. In some embodiments, the EDEM2 protein has the amino acid of SEQ ID NO: 8, or an amino acid sequence that is at least 92% identical to any one of SEQ ID NO: 1-7. In some embodiments, the polynucleotide comprises a nucleic acid sequence of SEQ ID NO: 16. In one particular embodiment, the polynucleotide consists of a nucleic acid sequence of SEQ ID NO: 14; and in another particular embodiment, SEQ ID NO: 15.

In another aspect, the invention provides an isolated or recombinant polynucleotide comprising a nucleic acid sequence encoding an XBP1 protein, which is operably linked to (in cis) a constitutive and ubiquitously expressed mammalian promoter, such as the ubiquitin C promoter. In some embodiments, the XBP1 protein has the amino acid of SEQ ID NO: 13, or an amino acid sequence that is at least 86% identical to any one of SEQ ID NO: 9-12. In some embodiments, the polynucleotide comprises a nucleic acid sequence of SEQ ID NO: 18. In one particular embodiment, the polynucleotide consists of a nucleic acid sequence of SEQ ID NO: 17.

In another aspect, the invention provides a cell that contains an EDEM2-encoding polynucleotide, as described in the prior aspect, and a polynucleotide that encodes a multi-subunit protein, such as an antibody. In some embodiments, the cell also contains an XBP1-encoding polynucleotide, as described in the preceding aspect. In one embodiment, the multi-subunit protein is an antibody, and the heavy chain of the antibody comprises an amino acid sequence of SEQ ID NO: 43 and SEQ ID NO: 44, and the light chain of the antibody comprises an amino acid sequence of SEQ ID NO: 45 and SEQ ID NO: 46. In this and several embodiments, each polypeptide subunit of the multi-subunit protein is encoded by a separate polynucleotide. Thus, for example, a polynucleotide encoding an antibody may include a polynucleotide encoding a heavy chain and a polynucleotide encoding a light chain, hence two subunits. In some embodiments, the cell is a Chinese hamster ovary (CHO) cell.

In one embodiment, the encoded multi-subunit protein is an anti-GDF8 antibody having a heavy chain variable region amino acid sequence of SEQ ID NO: 20 and a light chain variable region amino acid sequence of SEQ ID NO: 22. In one embodiment, the anti-GDF8 antibody comprises a heavy chain having an amino acid sequence of SEQ ID NO: 19 and a light chain having an amino acid sequence of SEQ ID NO: 21. In one embodiment, the polynucleotide that encodes the heavy chain of the anti-GDF8 antibody comprises a nucleic acid sequence of SEQ ID NO: 23; and the polynucleotide that encodes the light chain of the anti-GDF8 antibody comprises a nucleic acid sequence of SEQ ID NO: 25. In one embodiment, the polynucleotide that encodes the heavy chain of the anti-GDF8 antibody consists of a nucleic acid sequence of SEQ ID NO: 24; and the polynucleotide that encodes the light chain of the anti-GDF8 antibody consists of a nucleic acid sequence of SEQ ID NO: 26.

In another embodiment, the encoded multi-subunit protein is an anti-ANG2 antibody having a heavy chain variable region amino acid sequence of SEQ ID NO: 28 and a light chain variable region amino acid sequence of SEQ ID NO: 30. In one embodiment, the anti-ANG2 antibody comprises a heavy chain having an amino acid sequence of SEQ ID NO: 27 and a light chain having an amino acid sequence of SEQ ID NO: 29. In one embodiment, the polynucleotide that encodes the heavy chain of the anti-ANG2 antibody comprises a nucleic acid sequence of SEQ ID NO: 31; and the polynucleotide that encodes the light chain of the anti-ANG2 antibody comprises a nucleic acid sequence of SEQ ID NO: 33. In one embodiment, the polynucleotide that encodes the heavy chain of the anti-ANG2 antibody consists of a nucleic acid sequence of SEQ ID NO: 32; and the polynucleotide that encodes the light chain of the anti-ANG2 antibody consists of a nucleic acid sequence of SEQ ID NO: 34.

In another embodiment, the encoded multi-subunit protein is an anti-ANGPTL4 antibody having a heavy chain variable region amino acid sequence of SEQ ID NO: 36 and a light chain variable region amino acid sequence of SEQ ID NO: 38. In one embodiment, the anti-ANGPTL4 antibody comprises a heavy chain having an amino acid sequence of SEQ ID NO: 35 and a light chain having an amino acid sequence of SEQ ID NO: 37. In one embodiment, the polynucleotide that encodes the heavy chain of the anti-ANGPTL4 antibody comprises a nucleic acid sequence of SEQ ID NO: 39; and the polynucleotide that encodes the light chain of the anti-ANGPTL4 antibody comprises a nucleic acid sequence of SEQ ID NO: 41. In one embodiment, the polynucleotide that encodes the heavy chain of the anti-ANGPTL4 antibody consists of a nucleic acid sequence of SEQ ID NO: 40; and the polynucleotide that encodes the light chain of the anti-ANGPTL4 antibody consists of a nucleic acid sequence of SEQ ID NO: 42.

In another aspect, the invention provides a method of manufacturing a multi-subunit protein, by culturing a cell of the previous aspect in a medium, wherein the multi-subunit protein is synthesized in the cell and subsequently secreted into the medium. In some embodiments, the multi-subunit protein is an antibody, such as for example anti-GDF8, anti-ANG2, anti-ANGPTL4, or an antibody having a heavy chain sequence of SEQ ID NO: 43 and 44, and a light chain sequence of SEQ ID NO: 45 and 46. In some embodiments, the multi-subunit protein attains a titer of at least 3 g/L, at least 5 g/L, at least 6 g/L, or at least 8 g/L. In some embodiments, the cell proliferates in the medium and establishes an integrated cell density of about $\geq 5 \times 10^7$ cell-day/mL, about $\geq 1 \times 10^8$ cell-day/mL, or about $\geq 1.5 \times 10^8$ cell-day/mL.

In another aspect, the invention provides a multi-subunit protein, which is manufactured according to the method described in the preceding aspect. In one embodiment, the manufactured protein is an antibody. In some embodiments, the antibody consists of a heavy chain, which comprises an amino acid sequence of SEQ ID NO: 43 and SEQ ID NO: 44, and a light chain, which comprises an amino acid sequence of SEQ ID NO: 45 and SEQ ID NO: 46. In one specific embodiment, the manufactured multi-subunit protein is an anti-GDF8 antibody having a heavy chain variable region amino acid sequence of SEQ ID NO: 20 and a light chain variable region amino acid sequence of SEQ ID NO: 22. In another specific embodiment, the manufactured multi-subunit protein is an anti-ANG2 antibody having a heavy chain variable region amino acid sequence of SEQ ID NO: 28 and a light chain variable region amino acid sequence of SEQ ID NO: 30. In yet another specific embodiment, the manufactured multi-subunit protein is an anti-ANGPTL4 antibody having a heavy chain variable region amino acid sequence of SEQ ID NO: 36 and a light chain variable region amino acid sequence of SEQ ID NO: 38.

BRIEF DESCRIPTION OF THE DRAWINGS

FIG. 2A shows the FACS scans (flow cytometry-based autologous secretion trap (FASTR)) of several clones expressing XBP1. Inconsistency in the peaks is indicative of unstable growth (i.e. a variable or heterogeneous mixture) of the cells in the clones tested.

FIG. 2B shows the FACS scans of several clones expressing EDEM2, having little to no variation in the peaks representative of clonal stability in the clones tested. FIG. 2B depicts the clonal stability of several clonal cell-lines expressing EDEM2 and an antibody of interest.

DESCRIPTION OF THE INVENTION

Figure 1A:
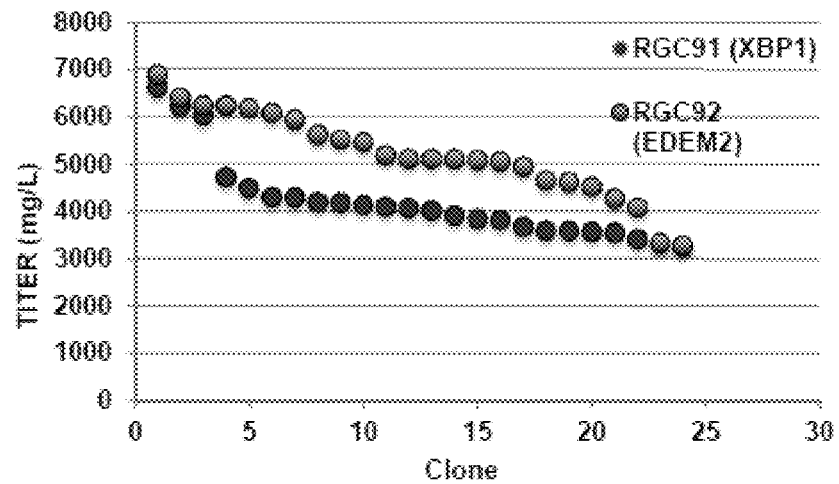
FIG. 1A shows consistently higher protein titer (in mg/L) for EDEM2-expressing clonal cell-lines (gray circles) compared to XBP1-expressing clonal cell-lines (black circles).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference in their entirety.

As used herein, the term "recombinant polynucleotide", which is used interchangeably with "isolated polynucleotide", means a nucleic acid polymer such as a ribonucleic acid or a deoxyribonucleic acid, either single stranded or double stranded, originating by genetic engineering manipulations. A recombinant polynucleotide may be a circular plasmid or a linear construct existing in vitro or within a cell as an episome. A recombinant polynucleotide may be a construct that is integrated within a larger polynucleotide molecule or supermolecular structure, such as a linear or circular chromosome. The larger polynucleotide molecule or supermolecular structure may be within a cell or within the nucleus of a cell. Thus, a recombinant polynucleotide may be integrated within a chromosome of a cell.

As used herein, the term "stress-induced mannose-binding lectin" refers to a mannose-binding protein, which means a protein that binds or is capable of binding mannose, derivatives of mannose, such as mannose-6-phosphate, or a glycoprotein that expresses mannose or a mannose derivative in its glycocalyx; and whose activity is upregulated during stress. Cellular stress includes inter alia starvation, DNA damage, hypoxia, poisoning, shear stress and other mechanical stresses, tumor stress, and the accumulation of misfolded proteins in the endoplasmic reticulum. Exemplary stress-induced mannose-binding lectins include the EDEM proteins EDEM1, EDEM2 and EDEM3, Yos 9, OS9, and XTP3-B (see Vembar and Brodsky, Nat. Rev. Mol. Cell. Biol. 9(12): 944-957, 2008, and references cited therein).

As used herein, the term "EDEM2" means any ortholog, homolog, or conservatively substituted variant of endoplasmic reticulum degradation-enhancing alpha-mannosidase-like protein. EDEM2 proteins are generally known in the art to be involved endoplasmic reticulum-associated degradation (ERAD), being up-regulated by Xbp-1 and facilitating the extraction of misfolded glycoproteins from the calnexin cycle for removal. (See Mast et al., Glycobiology 15(4): 421-436, 2004; Olivari and Molinari, FEBS Lett. 581: 3658-3664, 2007; Olivari et al., J. Biol. Chem. 280(4): 2424-2428, 2005; and Vembar and Brodsky 2008, which are herein incorporated by reference.) Exemplary EDEM2 sequences are depicted in Table 1, which is cross-referenced to the Sequence Listing.

TABLE 1

| Animal | SEQ ID NO: | % id human | % id mouse | % id hamster |
|---|---|---|---|---|
| Mouse | 1 | 93 | 100 | 96 |
| Rat | 2 | 94 | 98 | 96 |
| Hamster | 3 | 93 | 96 | 100 |
| Human | 4 | 100 | 93 | 93 |
| Chimpanzee | 5 | 99 | 94 | 93 |
| Orangutan | 6 | 97 | 92 | 92 |
| Zebra fish | 7 | 69 | 70 | 69 |
| Consensus | 8 | 100 | 100 | 100 |

As used herein, the term "Xbp1", also known as XBP1 or X-box binding protein 1, means any ortholog, homolog, or conservatively substituted variant of Xbp1. Xbp1 is a transcription factor and functional element of the UPR. ER stress activates both (1) the transcription factor ATF6, which in turn upregulates the transcription of Xbp1 mRNA, and (2) the ER membrane protein IRE1, which mediates the splicing of the precursor Xbp1 mRNA to produce active Xbp1. As mentioned above, activated Xbp1 in turn upregulates the activity of EDEM2. (See Yoshida et al., Cell Structure and Function 31(2): 117-125, 2006; and Olivari, 2005.) Exemplary Xbp1 amino acid sequences are depicted in Table 2, which is cross-referenced to the Sequence Listing.

TABLE 2

| Animal | SEQ ID NO | % id human | % id mouse | % id hamster |
|---|---|---|---|---|
| Mouse | 9 | 86 | 100 | 92 |
| Hamster | 10 | 86 | 92 | 100 |
| Human | 11 | 100 | 86 | 86 |
| Zebra fish | 12 | 47 | 47 | 48 |
| Consensus | 13 | 100 | 100 | 100 |

As used herein, the term "antibody" is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody". Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. An "isolated antibody" or "purified antibody" may be substantially free of other cellular material or chemicals.

The term "specifically binds", or the like, means that an antibody or antigen-binding fragment thereof forms a complex with an antigen that is relatively stable under physiologic conditions. Specific binding can be characterized by a dissociation constant of at least about $1 \times 10^{-6}$ M or greater. Methods for determining whether two molecules specifically bind are well known in the art and include, for example, equilibrium dialysis, surface plasmon resonance, and the like. An isolated antibody that specifically binds human GDF8 (for example) may, however, have cross-reactivity to other antigens, such as GDF8 molecules from other species (orthologs).

Various antibodies are used as examples of multi-subunit proteins secreted by cells harboring the polynucleotide encoding a stress-induced mannose-binding lectin. Those examples include anti-GDF8, anti-ANG2, and anti-ANGPTL4 antibodies. These and similar antibodies are described in US Pat. Apps. No. 20110293630, 20110027286, and 20110159015 respectively, which are incorporated herein by reference.

As used herein, the term "cell" refers to a prokaryotic or eukaryotic cell capable of replicating DNA, transcribing RNA, translating polypeptides, and secreting proteins. Cells include animal cells used in the commercial production of biological products, such as insect cells (e.g., Schneider cells, Sf9 cells, Sf21 cells, Tn-368 cells, BTI-TN-5B1-4 cells; see Jarvis, Methods Enzymol. 463: 191-222, 2009; and Potter et al., Int. Rev. Immunol. 10(2-3): 103-112, 1993) and mammalian cells (e.g., CHO or CHO-K1 cells, COS or COS-7 cells, HEK293 cells, PC12 cells, HeLa cells, Hybridoma cells; Trill et al., Curr. Opin. Biotechnol. 6(5): 553-560, 1995; Kipriyanov and Little, Mo. Biotechnol. 12(2): 173-201, 1999). In one embodiment, the cell is a CHO-K1 cell containing the described UPR pathway polynucleotides. For a description of CHO-K1 cells, see also Kao et al., Proc. Nat'l. Acad. Sci. USA 60: 1275-1281, 1968.

As used herein, the term "promoter" means a genetic sequence generally in cis and located upstream of a protein coding sequence, and which facilitates the transcription of the protein coding sequence. Promoters can be regulated (developmental, tissue specific, or inducible (chemical, temperature)) or constitutively active. In certain embodiments, the polynucleotides that encode proteins are operably linked to a constitutive promoter. By "operably linked", what is meant is that the protein-encoding polynucleotide is located three-prime (downstream) and cis of the promoter, and under control of the promoter. In certain embodiments, the promoter is a constitutive mammalian promoter, such as the ubiquitin C promoter (see Schorpp et al., Nucl. Acids Res. 24(9): 1787-1788, 1996); Byun et al., Biochem. Biophys. Res. Comm 332(2): 518-523, 2005) or the CMV-IE promoter (see Addison et al., J. Gen. Virol. 78(7): 1653-1661, 1997; Hunninghake et al., J. Virol. 63(7): 3026-3033, 1989), or the hCMV-IE promoter (human cytomegalovirus immediate early gene promoter) (see Stinski & Roehr, J. Virol. 55(2): 431-441, 1985; Hunninghake et al., J. Virol. 63(7): 3026-3033, 1989).

As used herein, the phrase "integrated cell density", or "ICD" means the density of cells in a culture medium taken as an integral over a period of time, expressed as cell-days per mL. In some embodiments, the ICD is measured around the twelfth day of cells in culture.

As used herein, the term "culture" means both (1) the composition comprising cells, medium, and secreted multi-subunit protein, and (2) the act of incubating the cells in medium, regardless of whether the cells are actively dividing or not. Cells can be cultured in a vessel as small as a 25 mL flask or smaller, and as large as a commercial bioreactor of 10,000 liters or larger. "Medium" refers to the culture medium, which comprises inter alia nutrients, lipids, amino acids, nucleic acids, buffers and trace elements to allow the growth, proliferation, or maintenance of cells, and the production of the multi-subunit protein by the cells. Cell culture media include serum-free and hydrolysate-free defined media as well as media supplemented with sera (e.g., fetal bovine serum (FBS)) or protein hydrolysates. Non-limiting examples of media, which can be commercially acquired, include RPMI medium 1640, Dulbecco's Modified Eagle Medium (DMEM), DMEM/F12 mixture, F10 nutrient mixture, Ham's F12 nutrient mixture, and minimum essential media (MEM).

As used herein, the phrase "conservatively substituted variant", as applied to polypeptides, means a polypeptide having an amino acid sequence with one of more conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-45, herein incorporated by reference. A "moderately conservative" replacement is any change having a nonnegative value in the PAM250 log-likelihood matrix.

EMBODIMENTS

The Cell

In one aspect, the invention provides a cell useful in the production of a protein having therapeutic or research utility. In some embodiments, the protein consists of multiple subunits, which must be properly folded and assembled to produce sufficient quantities of active protein. Antibodies are an example of multi-subunit proteins having therapeutic or research utility. In some embodiments, the cell harbors a recombinant genetic construct (i.e., a polynucleotide) that encodes one or more of the individual subunits of the multi-subunit protein. In other embodiments, the genetic construct encoding the individual polypeptide subunits is naturally occurring, such as for example the nucleic acid sequences encoding the subunits of an antibody in a B cell.

To facilitate the proper assembly and secretion of the multi-subunit protein, the cell contains a recombinant polynucleotide that encodes a stress-induced mannose-binding lectin, which in some embodiments is a component of the ERAD. In some embodiments, the stress-induced mannose-binding lectin is an endoplasmic reticulum degradation-enhancing alpha-mannosidase-like protein 2 (EDEM2). It is envisioned that any encoded EDEM2 or conservatively-substituted variant can be successfully employed in the instant invention. Table 1 lists some examples of vertebrate EDEM2 proteins. A multiple pairwise comparison of those protein sequences, which was performed using the Clustal W program of Thompson et al., Nucl. Acids Rev. 22(22): 4673-80, 1994 (see also Yuan et al., Bioinformatics 15(10): 862-3, 1999), revealed that each of the disclosed EDEM2 polynucleotide sequences is at least 69% identical to each other EDEM2 sequence. A Clustal W comparison of the disclosed mammalian EDEM2 sequences revealed that each sequence is at least 92% identical to the other. Thus, in some embodiments, the cell contains a polynucleotide that encodes an EDEM2 polypeptide having a sequence that is at least 92% to any one of a mammalian EDEM2. A consensus EDEM2 amino acid sequence was built by aligning a mouse, rat, hamster, chimpanzee, and human EDEM2 polypeptide amino acid sequences. That consensus sequence is depicted as SEQ ID NO: 8. Thus, in some embodiments, the cell contains a polynucleotide that encodes an EDEM2 polypeptide having an amino acid sequence of SEQ ID NO: 8.

In various embodiments, the cell contains a recombinant polynucleotide that encodes an EDEM2 polypeptide having an amino acid sequence that is at least 92% identical to the mouse EDEM2 (mEDEM2) amino acid sequence; and in a particular embodiment, the polypeptide is mEDEM2 or a conservatively substituted variant thereof.

In some embodiments, the multi-subunit protein is an antibody, and the cell contains a polynucleotide encoding any one or more of a polypeptide comprising an amino acid sequence of SEQ ID NO: 43, SEQ ID NO: 44, SEQ ID NO: 45, and SEQ ID NO: 46. SEQ ID NO: 43 and 44 each represent consensus sequences of the roughly N-terminal and C-terminal portions, respectively, of particular antibody heavy chains. Thus, the polynucleotide encoding a protein subunit in one embodiment encodes a polypeptide comprising both SEQ ID NO: 43 and SEQ ID NO: 44. SEQ ID NO: 45 and 46 each represent consensus sequences of the roughly N-terminal and C-terminal portions, respectively, of particular antibody light chains. Thus, the polynucleotide encoding a protein subunit in one embodiment encodes a polypeptide comprising both SEQ ID NO: 45 and SEQ ID NO: 46. In some embodiments, in addition to the recombinant polynucleotide encoding the EDEM2 protein, the cell contains at least two polynucleotides, each of which encodes a particular subunit of the multi-subunit protein. For example, and as exemplified below, the cell contains a polynucleotide encoding an antibody heavy chain comprising an amino acid sequence of SEQ ID NO: 43 and SEQ ID NO: 44, and another polynucleotide encoding an antibody light chain comprising an amino acid sequence of SEQ ID NO: 45 and SEQ ID NO: 46.

In some embodiments, the cell, in addition to containing the stress-response polynucleotide and one or more polynucleotides encoding a polypeptide subunit, as described above, also contains a polynucleotide that encodes an unfolded protein response transcription factor that operates upstream of EDEM2. The upstream transcription factor is in some cases the spliced form of an XBP1. It is envisioned that any encoded XBP1 can be successfully employed in the instant invention. Table 2 lists some examples of sequences of vertebrate XBP1 spliced-form polypeptides. A multiple pairwise comparison of those polypeptide sequences, which was performed using Clustal W (Thompson 1994; Yuan 1999), revealed that each of the disclosed spliced XBP1 polynucleotide sequences is at least 48% identical to each other XBP1 sequence. A Clustal W comparison of the disclosed mammalian XBP1 sequences revealed that each sequence is at least 86% identical to the other. Thus, in some embodiments, the cell contains a polynucleotide that encodes a spliced-form of an XBP1 polypeptide having a sequence that is at least 86% to any one of a mammalian spliced XBP1. A consensus XBP1 amino acid sequence was built by aligning a mouse, hamster, and human XBP1 amino acid sequences. That consensus sequence is depicted as SEQ ID NO: 13. Thus, in some embodiments, the cell contains a polynucleotide that encodes an XBP1 polypeptide having an amino acid sequence of SEQ ID NO: 13.

In various embodiments, the cell contains a polynucleotide that encodes an XBP1 polypeptide having an amino acid sequence that is at least 86% identical to the mouse XBP1 (mXBP1) amino acid sequence (SEQ ID NO: 9); and in a particular embodiment, the polypeptide is mXBP1, or a conservatively substituted variant thereof.

The invention envisions that any cell may be used to harbor the lectin-encoding polypeptide for the production of a properly folded and active multi-subunit protein. Such cells include the well-known protein production cells such as the bacterium *Escherichia coli* and similar prokaryotic cells, the yeasts *Pichia pastoris* and other *Pichia* and non-pichia yeasts, plant cell explants, such as those of *Nicotiana*, insect cells, such as Schneider 2 cells, Sf9 and Sf21, and the *Trichoplusia ni*-derived High Five cells, and the mammalian cells typically used in bioproduction, such as CHO, CHO-K1, COS, HeLa, HEK293, Jurkat, and PC12 cells. In some embodiments, the cell is a CHO-K1 or a modified CHO-K1 cell such as that which is taught in U.S. Pat. Nos. 7,435,553, 7,514,545, and 7,771,997, as well as U.S. Published Patent Application No. US 2010-0304436 A1, each of which is incorporated herein by reference in its entirety.

In some particular embodiments, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence that encodes a polypeptide comprising the amino acid sequences of SEQ ID NO: 43 and 44, and (4) an antibody light chain-encoding polynucleotide comprising a nucleotide sequence that encodes a polypeptide comprising the amino acid sequences of SEQ ID NO: 45 and 46.

In one particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO:18, (3) an antibody heavy chain-encoding polynucleotide comprising a nucleotide sequence of SEQ ID NO: 23, and (4) an antibody light chain-encoding polynucleotide comprising a nucleotide sequence of SEQ ID NO: 25.

In another particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 31, and (4) an antibody light chain-encoding polynucleotide comprising a nucleotide sequence of SEQ ID NO: 33.

In yet another particular embodiment, the invention provides ex vivo a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 39, and (4) an antibody light chain-encoding polynucleotide comprising a nucleotide sequence of SEQ ID NO: 41.

The Cell Line

In another aspect, the invention provides a cell line, which comprises a plurality of cells descended by clonal expansion from a cell described above. At least 50%, at least 60%, at least 70%, at least 80%, at least 90%, at least 95%, at least 98%, at least 99%, or about 100% of the constituent cells of the cell line contain a recombinant polynucleotide that encodes a stress-induced mannose-binding lectin, which in some embodiments is a component of the ERAD. In some embodiments, the stress-induced mannose-binding lectin is an endoplasmic reticulum degradation-enhancing alpha-mannosidase-like protein 2 (EDEM2). It is envisioned that any encoded EDEM2 or conservatively-substituted variant thereof can be successfully employed in the instant invention. Table 1, as discussed in the previous section, lists some examples of vertebrate EDEM2 proteins. In some embodiments, the constituent cell contains a polynucleotide that encodes an EDEM2 polypeptide having a sequence that is at least 92% identical to any mammalian EDEM2. In some embodiments, the constituent cell contains a polynucleotide that encodes an EDEM2 polypeptide having the mammalian consensus amino acid sequence of SEQ ID NO: 8. In some embodiments, the constituent cell contains a recombinant polynucleotide of SEQ ID NO: 1 or a conservatively substituted variant thereof.

In some embodiments, the multi-subunit protein that is produced by the cell line is an antibody, and the constituent cell of the cell line contains a polynucleotide encoding any one or more of a polypeptide comprising an amino acid sequence of SEQ ID NO: 43 and SEQ ID NO: 44 (which represent consensus sequences of the N-terminal and C-terminal portions, respectively, of particular antibody heavy chains), and SEQ ID NO: 45 and SEQ ID NO: 46 (which represent consensus sequences of the N-terminal and C-terminal portions, respectively, of particular antibody light chains). In some embodiments, in addition to the recombinant polynucleotide encoding the EDEM2 protein, the constituent cell of the cell line contains at least two polynucleotides, each of which encodes a particular subunit of the multi-subunit protein. For example, the constituent cell contains a polynucleotide encoding an antibody heavy chain comprising an amino acid sequence of SEQ ID NO: 43 and SEQ ID NO: 44, and another polynucleotide encoding an antibody light chain comprising an amino acid sequence of SEQ ID NO: 45 and SEQ ID NO: 46.

In some embodiments, the constituent cell, in addition to containing the stress-response polynucleotide and one or more polynucleotides encoding a polypeptide subunit, as described above, also contains a polynucleotide that encodes an unfolded protein response transcription factor, which operates upstream of EDEM2, such as a spliced form of an XBP1. It is envisioned that any encoded XBP1 can be successfully employed in the instant invention. Table 2, as discussed in the preceding section, lists some examples of sequences of vertebrate XBP1 spliced-form polypeptides. Clustal W analysis of those sequences revealed that each of the disclosed spliced XBP1 polynucleotide sequences is at least 48% identical to each other XBP1 sequence; and a comparison of the mammalian XBP1 sequences revealed that each sequence is at least 86% identical to the other. Thus, in some embodiments, the constituent cell of the cell line contains a polynucleotide that encodes a spliced-form of an XBP1 polypeptide having a sequence that is at least 86% to any one of a mammalian spliced XBP1. In some embodiments, the constituent cell contains a polynucleotide that encodes an XBP1 polypeptide having a consensus amino acid sequence of SEQ ID NO: 13.

In various embodiments, the cell contains a polynucleotide that encodes an XBP1 polypeptide having an amino acid sequence that is at least 86% identical to the mouse XBP1 (mXBP1) amino acid sequence (SEQ ID NO: 9); and in a particular embodiment, the polypeptide is mXBP1 of SEQ ID NO: 9, or a conservatively substituted variant thereof.

The invention envisions that the cell line comprises constituent cells whose parent is selected from a list of well-known protein production cells such as, e.g., the bacterium *Escherichia coli* and similar prokaryotic cells, the yeasts *Pichia pastoris* and other *Pichia* and non-pichia yeasts, plant cell explants, such as those of *Nicotiana*, insect cells, such as Schneider 2 cells, Sf9 and Sf21, and the *Trichoplusia ni*-derived High Five cells, and the mammalian cells typically used in bioproduction, such as CHO, CHO-K1, COS, HeLa, HEK293, Jurkat, and PC12 cells. In some embodiments, the cell is a CHO-K1 or a modified CHO-K1 cell, such as that which is taught in U.S. Pat. Nos. 7,435,553, 7,514,545, and 7,771,997, as well as U.S. Published Patent Application No. US 2010-0304436 A1.

In some embodiments, the cell line, which is cultured in media, is capable of producing the multi-subunit protein and secreting the properly assembled multi-subunit protein into the media to a titer that is at least 3 g/L, at least 5 g/L, or at least 8 g/L.

Furthermore, the constituent cells of the cell line are capable proliferating in culture to such an extent as to attain an integrated cell density that is about 30% greater than the integrated cell density of a cell line that does not contain the recombinant polynucleotide encoding the stress-induced mannose-binding lectin. In some cases, the cell line is able to attain an integrated cell density that is at least about 50% greater, at least 60% greater, or at least 90% greater than the integrated cell density of a cell line that does not contain the recombinant polynucleotide that encodes a stress-induced mannose-binding lectin. In some embodiments, the integrated cell density of the cell line is assessed after about 12 days in culture.

In some particular embodiments, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence that encodes a polypeptide comprising the amino acid sequences of SEQ ID NO: 43 and 44, and (4) an antibody light chain-encoding polynucleotide comprising a nucleotide sequence that encodes a polypeptide comprising the amino acid sequences of SEQ ID NO: 45 and 46.

In one particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 23, and (4) an antibody light chain-encoding polynucleotide comprising a nucleotide sequence of SEQ ID NO: 25.

In another particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1- encoding polynucleotide comprising a nucleotide sequence of SEQ ID NO: 18, (3) an antibody heavy chain-encoding polynucleotide comprising a nucleotide sequence of SEQ ID NO: 31, and (4) an antibody light chain-encoding polynucleotide comprising a nucleotide sequence of SEQ ID NO: 33.

In yet another particular embodiment, the invention provides a cell-line comprising clonally-derived constituent cells, wherein the constituent cell is a CHO-K1 cell that contains (1) a mEDEM2-encoding polynucleotide comprising a nucleotide sequence of SEQ ID NO: 16, (2) an XBP1-encoding polynucleotide comprising a nucleotide sequence of SEQ ID NO: 18, (3) an antibody heavy chain-encoding polynucleotide comprising a nucleotide sequence of SEQ ID NO: 39, and (4) an antibody light chain-encoding polynucleotide comprising a nucleotide sequence of SEQ ID NO: 41.

The EDEM2 Polynucleotide

In another aspect, the invention provides a polynucleotide that encodes an EDEM2 protein. The EDEM2-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the EDEM2-encoding polynucleotide is within a gene, meaning that it is under the control of and down stream of a promoter, and upstream of a polyadenylation site. The EDEM2-encoding polynucleotide or gene can be within a plasmid or other circular or linear vector. The EDEM2-encoding polynucleotide or gene can be within a circular or linear DNA construct, which can be within a cell as an episome or integrated into the cellular genome.

As described above, the EDEM2-encoding polynucleotide encodes any ortholog, homolog or conservatively substituted EDEM2 polypeptide of Table 1, or an EDEM2 polypeptide having an amino acid sequence that is at least 92% identical to any one of SEQ ID NO: 1-5 and 8, including the mammalian consensus sequence of SEQ ID NO: 8.

In some cases, the recombinant or isolated EDEM2-encoding polynucleotide is operably linked to a mammalian promoter. The promoter can be any promoter, but in some cases it is a mammalian promoter, such as for example a ubiquitin C promoter.

In a particular embodiment, the EDEM2-encoding polynucleotide essentially consists of, from 5' to 3', a promoter, such as a ubiquitin C promoter, followed by an optional intron, such as a beta globin intron, followed by an EDEM2 coding sequence, followed by a polyadenylation sequence, such as an SV40 pA sequence. A specific example, which is also a particular embodiment, of such an EDEM2-encoding polynucleotide is described by SEQ ID NO: 16. Conserved variants of that sequence are also envisioned to be embodiments of the invention.

In some cases, the recombinant EDEM2-encoding polynucleotide is part of a plasmid, which can be linear, circular, episomal, integrated, a static DNA construct, or a vector for delivering the EDEM2 gene or expressing the EDEM2 protein. In one particular embodiment, the plasmid contains (1) an EDEM2 gene, which is under the control of a ubiquitin C promoter and terminates with an SV40 polyadenylation signal, and (2) a selectable marker, such as a polynucleotide encoding a polypeptide that confers resistance to zeocin or a polynucleotide encoding a polypeptide that confers resistance to neomycin, under the control of a promoter, such as an SV40 promoter, and terminated with a polyadenylation sequence, such as a PGK pA sequence. In one particular embodiment, the plasmid comprises, in a circular format running in a 5' to 3' direction, a ubiquitin C promoter, a beta globin intron, an EDEM2 coding sequence, an SV40 pA sequence, an SV40 promoter, a neomycin-resistance coding sequence, and a PGK pA sequence. A specific example of this embodiment is exemplified by a plasmid having the sequence of SEQ ID NO: 14. In another particular embodiment, the plasmid comprises, in a circular format running in a 5' to 3' direction, a ubiquitin C promoter, a beta globin intron, an EDEM2 coding sequence, an SV40 pA sequence, an SV40 promoter, a zeocin-resistance coding sequence, and a PGK pA sequence. A specific example of this embodiment is exemplified by a plasmid having the sequence of SEQ ID NO: 15.

The XBP1 Polynucleotide

In another aspect, the invention provides a polynucleotide that encodes an XBP1 protein. The XBP1-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the XBP1-encoding polynucleotide is within a gene, meaning that it is under the control of and down stream of a promoter, and upstream of a polyadenylation site. The XBP1-encoding polynucleotide can be within a plasmid or other circular or linear vector. The XBP1-encoding polynucleotide or gene can be within a circular or linear DNA construct, which can be within a cell as an episome, or integrated into the cellular genome.

As described above, the XBP1-encoding polynucleotide encodes any ortholog, homolog or conservatively substituted XBP1 polypeptide of Table 2, or an XBP1 polypeptide having an amino acid sequence that is at least 86% identical to any one of SEQ ID NO: 9, 10, and 11, including the mammalian consensus sequence of SEQ ID NO: 13.

In some cases, the recombinant or isolated XBP1-encoding polynucleotide is operably linked to a mammalian promoter. The promoter can be any promoter, but in some cases it is a mammalian promoter, such as for example a ubiquitin C promoter.

In a particular embodiment, the XBP1-encoding polynucleotide essentially consists of, from 5' to 3', a promoter, such as a ubiquitin C promoter, followed by an optional intron, such as a beta globin intron, followed by an XBP1 coding sequence, followed by a polyadenylation sequence, such as an SV40 pA sequence. SEQ ID NO: 18 describes an example of an XBP1-encoding polynucleotide. Conserved variants of that exemplary sequence are also envisioned to be embodiments of the invention.

In some cases, the recombinant XBP1-encoding polynucleotide is part of a plasmid, which can be linear, circular, episomal, integrated, a static DNA construct, or a vector for delivering the XBP1 gene or expressing the spliced and active XBP1 protein. In one particular embodiment, the plasmid contains (1) an XBP1 gene, which is under the control of a ubiquitin C promoter and terminates with an SV40 polyadenylation signal, and (2) a selectable marker, such as a polynucleotide encoding a polypeptide that confers resistance to zeocin or a polynucleotide encoding a polypeptide that confers resistance to neomycin, under the control of a promoter, such as an SV40 promoter, and terminated with a polyadenylation sequence, such as a PGK pA sequence. In one particular embodiment, the plasmid comprises, in a circular format running in a 5' to 3' direction, a ubiquitin C promoter, a beta globin intron, an XBP1 coding sequence, an SV40 pA sequence, an SV40 promoter, a zeocin-resistance coding sequence, and a PGK pA sequence.

A specific example of this embodiment is exemplified by a circular plasmid having the sequence of SEQ ID NO: 17.

The Antibody Heavy and Light Chain-Encoding Polynucleotides

In another aspect, the invention provides a polynucleotide that encodes an antibody heavy chain polypeptide (HC). The HC-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the HC-encoding polynucleotide is within a gene, meaning that it is under the control of and down stream from a promoter, and upstream of a polyadenylation site. The HC-encoding polynucleotide may be within a plasmid or other circular or linear vector. The HC-encoding polynucleotide or gene may be within a circular or linear DNA construct, which may be within a cell as an episome or integrated into the cellular genome.

In some cases, the recombinant or isolated HC-encoding polynucleotide is operably linked to a mammalian promoter. The promoter can be any promoter, but in some cases it is a mammalian promoter, such as for example a ubiquitin C promoter or an hCMV-IE promoter.

In a particular embodiment, the HC-encoding polynucleotide is an HC gene, which essentially comprises, from 5' to 3', a promoter, for example an hCMV-IE promoter, followed by an optional intron, such as a beta globin intron, followed by a heavy chain coding sequence, such as for example a sequence encoding an amino acid sequence of SEQ ID NO: 43 and 44, SEQ ID NO: 19, SEQ ID NO: 27, or SEQ ID NO: 35, followed by a polyadenylation sequence, for example an SV40 pA sequence. A specific example of an HC gene is described by SEQ ID NO: 23, SEQ ID NO: 31, or SEQ ID NO: 39. Conserved variants of any one of these sequences are also envisioned to be embodiments of the invention.

In some cases, the recombinant HC-encoding polynucleotide is part of a plasmid, which can be linear, circular, episomal, integrated, a static DNA construct, or a vector for delivering the heavy chain gene or expressing the heavy chain sububunit. In one particular embodiment, the plasmid contains (1) an HC gene, which is under the control of an hCMV-IE promoter and terminates with an SV40 polyadenylation signal, and (2) a selectable marker, such as a polynucleotide encoding a polypeptide that confers resistance to hygromycin, under the control of a promoter, such as an SV40 promoter, and terminated with a polyadenylation sequence, such as a PGK pA sequence. In one particular embodiment, the plasmid comprises, in a circular format running in a 5' to 3' direction, an hCMV-IE promoter, a beta globin intron, an antibody heavy chain coding sequence (which encodes a HC having an amino acid of SEQ ID NO: 43 and 44, SEQ ID NO: 19, SEQ ID NO: 27, or SEQ ID NO: 35), an SV40 pA sequence, an SV40 promoter, a hygromycin-resistance coding sequence, and a PGK pA sequence. A specific example and particular embodiment of such a plasmid containing an HC gene is described by SEQ ID NO: 24, SEQ ID NO: 32, or SEQ ID NO: 40. Conserved variants of any one of these sequences are also envisioned to be embodiments of the invention.

In another aspect, the invention provides a polynucleotide that encodes an antibody light chain polypeptide (LC). The LC-encoding polynucleotide is recombinant and can be manufactured, stored, used or expressed in vitro, as in a test tube, or an in vitro translation system, or in vivo, such as in a cell, which can be ex vivo, as in a cell culture, or in vivo, as in an organism. In some embodiments, the LC-encoding polynucleotide is within a gene, meaning that it is under the control of and down stream from a promoter, and upstream of a polyadenylation site. The LC-encoding polynucleotide or gene may be within a plasmid or other circular or linear vector. The LC-encoding polynucleotide or gene may be within a circular or linear DNA construct, which may be within a cell as an episome or integrated into the cellular genome.

In some cases, the recombinant or isolated LC-encoding polynucleotide is operably linked to a mammalian promoter. The promoter can be any promoter, but in some cases it is a mammalian promoter, such as, e.g., a ubiquitin C promoter or an hCMV-IE promoter.

In a particular embodiment, the LC-encoding polynucleotide is an LC gene, which essentially comprises, from 5' to 3', a promoter, for example an hCMV-IE promoter, followed by an optional intron, such as a beta globin intron, followed by a light chain coding sequence, such as for example a sequence encoding an amino acid sequence of SEQ ID NO: 45 and 46, SEQ ID NO: 21, SEQ ID NO: 29, or SEQ ID NO: 37, followed by a polyadenylation sequence, such as an SV40 pA sequence. A specific example and particular embodiment of such an LC gene is described by SEQ ID NO: 25, SEQ ID NO: 33, or SEQ ID NO: 41. Conserved variants of any one of these sequences are also envisioned to be embodiments of the invention.

In some cases, the recombinant LC-encoding polynucleotide is part of a plasmid, which may be linear, circular, episomal, integrated, a static DNA construct, or a vector for delivering the light chain gene or expressing the light chain sububunit. In one particular embodiment, the plasmid contains (1) an LC gene, which is under the control of an hCMV-IE promoter and terminates with an SV40 polyadenylation signal, and (2) a selectable marker, such as a polynucleotide encoding a polypeptide that confers resistance to hygromycin, under the control of a promoter, such as an SV40 promoter, and terminated with a polyadenylation sequence, such as a PGK pA sequence. In one particular embodiment, the plasmid comprises, in a circular format running in a 5' to 3' direction, an hCMV-IE promoter, a beta globin intron, an antibody light chain coding sequence (which encodes a LC having an amino acid of SEQ ID NO: 45 and 46, SEQ ID NO: 21, SEQ ID NO: 29, or SEQ ID NO: 37), an SV40 pA sequence, an SV40 promoter, a hygromycin-resistance coding sequence, and a PGK pA sequence. A specific example and particular embodiment of such a plasmid containing an LC gene is described by SEQ ID NO: 26, SEQ ID NO: 34, or SEQ ID NO: 42. Conserved variants of any one of these sequences are also envisioned to be embodiments of the invention.

Methods of Manufacturing Multi-Subunit Proteins

In another aspect, the invention provides a method for manufacturing a multi-subunit protein by culturing a cell, or a constituent cell of a cell line, which is capable of producing and secreting relatively large amounts of a properly assembled multi-subunit protein, in a medium, wherein the multi-subunit component is secreted into the medium at a relatively high titer. The cell utilized in this manufacturing process is a cell described in the foregoing aspects, which contains an ERAD lectin-encoding polynucleotide described herein.

Methods of culturing cells, and in particular mammalian cells, for the purpose of producing useful recombinant proteins is well-known in the art (e.g., see De Jesus & Wurm, Eur. J. Pharm. Biopharm. 78:184-188, 2011, and references cited therein). Briefly, cells containing the described polynucleotides are cultured in media, which may contain sera or hydrolysates, or may be chemically defined and optimized for protein production. The cultures may be fed-batch cultures or continuous cultures, as in a chemostat. The cells may be cultured in lab bench size flasks (.about.25 mL), production scale-up bioreactors (1-5 L), or industrial scale bioreactors (5,000-25,000 L). Production runs may last for several weeks to a month, during which time the multi-subunit protein is secreted into the media.

The subject cell has an enhanced ability to produce and secrete properly assembled multi-subunit proteins. In some embodiments, the multi-subunit protein, for example an antibody, is secreted into the media at a rate of at least 94 pg/cell/day, at least 37 pg/cell/day, or at least 39 pg/cell/day. In some embodiments, the multi-subunit protein attains a titer of at least at least 3 g/L, at least 5 g/L, at least 6 g/L, or at least 8 g/L after about twelve days of culture.

Furthermore, the subject cell has an enhanced ability to proliferate and attain a relatively high cell density, further optimizing productivity. In some embodiments, the cell or cell-line seed train attains an integrated cell density in culture of at least $5 \times 10^7$ cell-day/mL, at least $1 \times 10^8$ cell-day/mL or at least $1.5 \times 10^8$ cell-day/mL.

Optionally, the secreted multi-subunit protein is subsequently purified from the medium into which it was secreted. Protein purification methods are well-known in the art (see e.g., Kelley, mAbs 1(5):443-452). In some embodiments, the protein is harvested by centrifugation to remove the cells from the liquid media supernatant, followed by various chromatography steps and a filtration step to remove inter alia viruses and other contaminants or adulterants. In some embodiments, the chromatography steps include an ion exchange step, such as cation-exchange or anion-exchange. Various affinity chromatographic media may also be employed, such as protein A chromatography for the purification of antibodies.

Optionally, the manufacturing method may include the antecedent steps of creating the cell. Thus, in some embodiments, the method of manufacturing the multi-subunit protein comprises the step of transfecting the cell with the vector that encodes the stress-induced mannose-binding lectin, as described above, followed by selecting stable integrants thereof. Non-limiting examples of vectors include those genetic constructs that contain a polynucleotide that encodes an EDEM2 having an amino acid sequence of any one of SEQ ID NO: 1-8, an amino acid sequence that is at least 92% identical to any one of SEQ ID NO: 1-8, or any one of a conservatively substituted variant of SEQ ID NO: 1-8. Useful vectors also include, for example, a plasmid harboring the gene of SEQ ID NO: 16, the plasmid of SEQ ID NO: 15, and the plasmid of SEQ ID NO: 14. One should keep in mind that the plasmid sequences (e.g., SEQ ID NO: 14, 15, 17, 24, 26, 32, 34, 40, and 42) are circular sequences described in a linear manner in the sequence listing. Thus, in those cases, the 3-prime-most nucleotide of the written sequence may be considered to be immediately 5-prime of the 5-prime-most nucleotide of the sequence as written. In the example of the plasmid of SEQ ID NO: 14, transformants are selected through resistance to neomycin; for SEQ ID NO: 15, by selection through ZEOCIN resistance.

Detailed methods for the construction of polynucleotides and vectors comprising same, are described in U.S. Pat. Nos. 7,435,553 and 7,771,997, which are incorporated herein by reference, and in, e.g., Zwarthoff et al., J. Gen. Virol. 66(4):685-91, 1985; Mory et al., DNA. 5(3):181-93, 1986; and Pichler et al., Biotechnol. Bioeng. 108(2):386-94, 2011.

The starting cell, into which the vector that encodes the stress-induced mannose-binding lectin is placed, may already contain the constructs or genetic elements encoding or regulating the expression of the subunits of the multi-subunit protein, or XBP1 for those embodiments utilizing XBP1. Alternatively, the vector that encodes the stress-induced mannose-binding lectin may be put inside the cell first, and followed by the other constructs.

Multi-Subunit Proteins Manufactured by the Process

In another aspect, the invention provides a multi-subunit protein that is made according to the process disclosed herein. Given the inclusion of one or more elements that facilitate the proper folding, assembly, and post-translational modification of a multi-subunit protein, such as an antibody, one of ordinary skill in the art would reasonably expect such a protein to have distinct structural and functional qualities. For example, an antibody manufactured by the disclosed process is reasonably believed to have a particular glycosylation pattern and a quantitatively greater proportion of non-aggregated heterotetramers.

EXAMPLES

The following examples are presented so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by mole, molecular weight is average molecular weight, percent concentration (%) means the mass of the solute in grams divided by the volume of the solution in milliliters times 100% (e.g., 10% substance X means 0.1 gram of substance X per milliliter of solution), temperature is in degrees Centigrade, and pressure is at or near atmospheric pressure.

Example 1 Cell Lines

CHO-K1 derived host cell line was transfected with two plasmids encoding heavy and light chain of a human antibody. Both plasmids contain the hph gene conferring resistance to hygromycin B (Asselbergs and Pronk, 1992, Mol. Biol. Rep., 17(1):61-70). Cells were transfected using LIPOFECTAMIN reagent (Invitrogen cat.#18324020). Briefly, one day before transfection 3.5 million cells were plated on a 10 cm plate in complete F12 (Invitrogen cat.#11765) containing 10% fetal bovine serum (FBS) (Invitrogen cat.#10100). On the day of transfection the cells were washed once and medium was replaced with OPTIMEM from (Invitrogen cat.#31985). DNA/Lipofectamin complexes were prepared in OPTIMEM medium and then added to the cells. The medium was changed again to the complete F12 with 10% FBS 6 hours later. The stable integration of the plasmids was selected using hygromycin B selection agent at 400 µg/ml. Clonal antibody expressing cell lines were isolated using the FASTR technology (described in the U.S. Pat. No. 6,919,183, which is herein incorporated by reference for the expression in a cell of a cell surface capture molecule that binds to a protein of interest to aid in the selection of those cells with high expression of the protein of interest).

The antibody expressing lines were then re-transfected with the EDEM2 encoding plasmid. EDEM2 plasmids contained either neomycin phosphotransferase (plasmid construct designated "p3") or sh ble (plasmid "p7") genes to confer resistance to either G418 or zeocin respectively. The same transfection method was used. Depending on the selectable marker, cells were selected with either G418 or zeocin at 400 µg/ml or 250 µg/ml, respectively. The clonal cell lines were then isolated using FASTR technology.

TABLE 3

CELL LINES

| Name | Enhancers | Constructs | Protein |
|------|-----------|------------|---------|
| C1 | EDEM2 + XBP1 | HC/LC = p1/p2 | anti-Ang2 |
| C2 | XBP1 | EDEM2 = p3 | |
| | | XBP1 = p4 | |
| C3 | EDEM2 + XBP1 | HC/LC = p5/p6 | anti-GDF8 |
| C4 | XBP1 | EDEM2 = p7 | |
| C5 | EDEM2 | XBP1 = p4 | |
| C6 | EDEM2 + XBP1 | HC/LC = p8/p9 | anti-AngPtl4 |
| C7 | XBP1 | EDEM2 = p3 | |
| | | XBP1 = p4 | |

Example 2

The antibody production was evaluated in a scaled-down 12-day fed batch process using shaker flasks. In this method the cells were seeded in a shaker flask at the density of 0.8 million cells per mL in the production medium (defined media with high amino acid). The culture was maintained for about 12 days, and was supplemented with three feeds as well as glucose. The viable cell density, and antibody titer were monitored throughout the batch.

To determine the effect of mEDEM2 on enhanced protein production, the production of proteins by CHO cell lines containing mEDEM2 and mXBP1 were compared to production by control cells that contained mXBP1, but not mEDEM2. Protein titers were higher in those cell lines expressing mEDEM2 versus those cell lines that did not express mEDEM2.

TABLE 4

TITERS

| Cell Line | Enhancers | Production rate (pg/cell/day) | Titer g/L (% increase) |
|-----------|-----------|-------------------------------|------------------------|
| C1 | EDEM2 + XBP1 | 39 | 8.1 (93) |
| C2 | XBP1 | 39 | 4.2 |
| C3 | EDEM2 + XBP1 | 37 | 5.9 (55) |
| C8 | XBP1 | 32 | 3.8 |
| C6 | EDEM2 + XBP1 | 94 | 5.3 (152) |
| C7 | XBP1 | 52 | 2.1 |
| C5 | EDEM2 | 29 | 3.1 (343) |
| C9 | — | 9 | 0.7 |

Example 3 Integrated Cell Days

Integrated Cell Density ("ICD") is a phrase used to describe the growth of the culture throughout the fed batch process. In the course of the 12-day production assay, we monitored viable cell density on days 0, 3, 5, 7, 10, and 12. This data was then plotted against time. ICD is the integral of viable cell density, calculated as the area under the cell density curve. EDEM2 transfected lines have higher ICD in a 12-day fed batch process (see Table 5).

TABLE 5

INTEGRATED CELL DENSITIES

| Cell Line | Enhancers | ICD $10^6$ cell-day/mL (% increase) |
|-----------|-----------|-------------------------------------|
| C1 | EDEM2 + XBP1 | 205 (93) |
| C2 | XBP1 | 106 |
| C3 | EDEM2 + XBP1 | 157 (34) |
| C4 | XBP1 | 117 |
| C6 | EDEM2 + XBP1 | 56 (51) |
| C7 | XBP1 | 37 |
| C5 | EDEM2 | 116 (59) |
| C9 | — | 73 |

Example 4 Anti-GDF8 Antibody Production

The effect of ectopic expression of EDEM2, XBP1, or both on the production of an anti-GDF8 antibody having a heavy chain sequence of SEQ ID NO: 19 and a light chain sequence of SEQ ID NO: 21 was examined. Individual cell-lines were examined for titer and integrated cell density and placed into "bins", or ranges of values. Ectopic expression of EDEM2 significantly increased the number of cell lines that express antibody in the 5-6 g/L titer range. The combination of XBP1 and EDEM2 showed more than an additive effect toward the increase in high titer cell lines. The expression of EDEM2 in the antibody secreting cells also significantly increased the number of cell lines that attain a high ICD (see Table 6).

TABLE 6

| con-struct | Titre Bins (g/L) | | | | ICD Bins ($10^6$ cell-day/mL) | | |
|---|---|---|---|---|---|---|---|
| | <1 | 1-3 | 3-5 | 5-6 | 30-50 | 50-100 | 100-200 |
| E + X | 0% | 33.3% | 44.4% | 22.2% | 11.1% | 50% | 38.9% |
| X | 0% | 37.5% | 54% | 8.3% | 14.3% | 85.7% | 0% |
| E | 0% | 33% | 60% | 7% | 0% | 27% | 73% |
| — | 82% | 18% | 0% | 0% | 13% | 67% | 21% |

Example 5 Productivity and Stability of EDEM2-Expressing Cells

The effect of ectopic expression of XBP1 or EDEM2 on the production of a monospecific antibody of interest (identified as clonal cell lines RGC91 or RGC92, respectively) was examined. Individual cell lines were examined for protein titer and integrated cell density, as well as stability.

Modified CHO K1 host cells stably expressing XBP1 (RGC91) or EDEM2 (RGC92) at a transcriptionally active locus (U.S. Pat. No. 8,389,239B2, issued Mar. 5, 2013) were transfected with a recombinant plasmid vector comprising the antibody gene of interest and a hygromycin resistance gene (hyg).

400 µg/mL hygromycin was used for selection of transfected cells. Positive integrants expressing the antibody of interest (randomly integrated in the CHO genome), and also stably expressing either XBP1 or EDEM2, were confirmed and isolated by fluorescence-activated cell sorting (FACS) analysis. The isolated clones were expanded in suspension cultures in serum-free production medium. Clones were isolated from selected pools and were subjected to a 12 day fed batch productivity assay, and the protein titer of the antibody of interest was determined. Integrated cell density is calculated by measuring viable cell count on a given day in the production assay (counts are taken every 3 days and plotted on a curve against cell count).

Figure 1B:
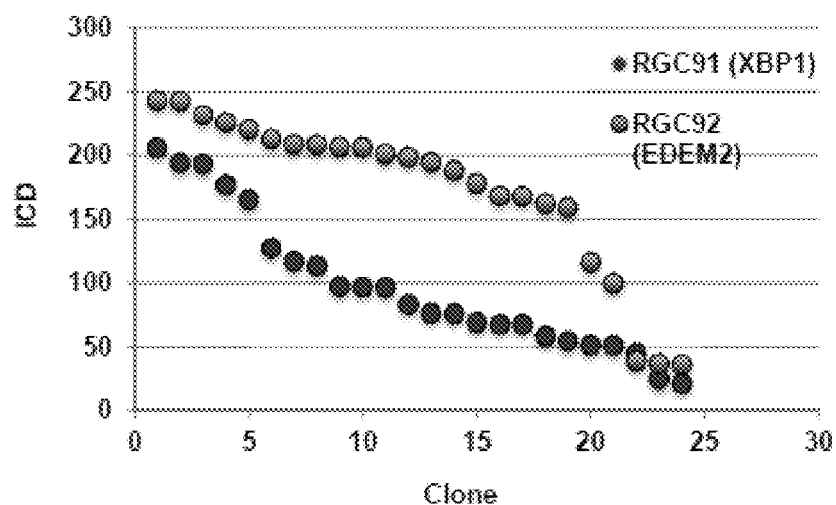
FIG. 1B depicts the integrated cell density (cell-days/mL) for EDEM2-expressing clones (gray circles) compared to XBP1-expressing clones (black circles). Each clone (#1-24) expresses the same gene of interest (antibody), under the same regulatory conditions, and expressing either XBP1 (RGC91) or EDEM2 (RGC92) at a transcriptionally active locus.

As shown in FIG. 1A, the average protein titers for clones isolated from RGC91 and RGC92 was 4.2 and 5.2, respectively (for 24 representative antibody-expressing clones). Ectopic expression of EDEM2 increased the number of clones that attain antibody titer above 5 g/L (FIG. 1A) compared to XBP1-expressing clones. Clonal cell lines expressing EDEM2 isolated from the RGC92 host also maintained higher (25%-100% higher) integrated cell densities when compared to clones isolated from XBP1-expressing RGC91 host (see FIG. 1B). EDEM2 clones established an ICD greater than 100 (FIG. 1B) in most clones tested. Clones isolated from EDEM2 expressing RGC92 host also resulted in significantly higher stability (FIG. 2B), as observed in flow cytometry-based autologous secretion trap (FASTR) scans (for reference, U.S. Pat. No. 6,919,183B2, issued Jul. 19, 2005) showing a homogenous producing population, in the representative sample of 24 clonal cell lines tested. Many of the clones isolated from XBP1 expressing RGC91 host appear to have a non-producing heterogeneous cell population (FIG. 2A). Without being bound to any one theory, EDEM2 facilitated the removal of misfolded proteins in the high expressing clones, thereby reducing stress in the cell during protein production and resulting in a more stable cell population.

What is claimed is:

1. A eukaryotic cell comprising:
   a. a first polynucleotide comprising a nucleic acid sequence encoding a first production enhancer protein comprising an amino acid sequence that is at least 92% identical to SEQ ID NO:9; and
   b. a second polynucleotide comprising a nucleic acid encoding a multi-subunit protein comprising an amino acid sequence of SEQ ID NO:44,
   wherein the cell produces the multi-subunit protein at a rate of at least 32 pg/cell/day.

2. The cell of claim 1 wherein the first polynucleotide further comprises a constitutive promoter operably linked to the nucleic acid encoding the first production enhancer protein.

3. The cell of claim 2 wherein the constitutive promoter of the first polynucleotide is selected from the group consisting of ubiquitin C promoter, CMV-IE promoter, and SV40 promoter.

4. The cell of claim 1 wherein the first polynucleotide is integrated at a transcriptionally active locus of the cell.

5. The cell of claim 1 wherein the first production enhancer protein comprises the amino acid sequence selected from the group consisting of SEQ ID NO: 13, SEQ ID NO:9, and SEQ ID NO:10.

6. The cell of claim 1 wherein the cell further comprises a third polynucleotide comprising a nucleic acid sequence encoding a second production enhancer protein comprising an amino acid sequence that is at least 92% identical to SEQ ID NO: 1.

7. The cell of claim 6 wherein the third polynucleotide further comprises a constitutive promoter operably linked to the nucleic acid encoding the second production enhancer protein.

8. The cell of claim 7 wherein the constitutive promoter is selected from the group consisting of ubiquitin C promoter, CMV-IE promoter, and SV40 promoter.

9. The cell of claim 6 wherein the second production enhancer protein comprises the amino acid sequence selected from the group consisting of SEQ ID NO: 8, SEQ ID NO:1, SEQ ID NO:2, SEQ ID NO:3, SEQ ID NO:4, SEQ ID NO:5, and SEQ ID NO:6.

10. The cell of claim 6 wherein the cell produces the multi-subunit protein at a rate of at least 37 pg/cell/day.

11. The cell of claim 1 wherein the multi-subunit protein is an antibody.

12. The cell of claim 11 wherein the antibody comprises a light chain with an amino acid sequence of SEQ ID NO:46.

13. The cell of claim 12 wherein the antibody is an anti-GDF8 antibody, an anti-Ang2 antibody, or an anti-AngPtl4 antibody.

14. The cell of claim 1 wherein the cell is a modified CHO-K1 cell.

15. The cell of claim 6 further comprising a fourth polynucleotide encoding a cell surface capture molecule that binds the multi-subunit protein.

16. A cell line comprising a plurality of cells descended by clonal expansion from the cell of claim 1.

17. A method of making a multi-subunit protein comprising:
   a. culturing in media a plurality of eukaryotic cells descended by clonal expansion from a eukaryotic cell comprising:
      i. a first polynucleotide comprising a nucleic acid encoding a first production enhancer protein comprising an amino acid sequence that is at least 92% identical to SEQ ID NO:9, and
      ii. a second polynucleotide comprising a nucleic acid encoding a multi-subunit protein comprising an amino acid sequence of SEQ ID NO:44;
   b. allowing the cells to secrete the multi-subunit protein into the media at a rate greater than 32 pg/cell/day; and
   c. purifying the multi-subunit protein from the media by affinity chromatography, ion exchange chromatography, or a combination of affinity chromatography and ion exchange chromatography.

18. The method of claim 17 wherein the first production enhancer protein comprises an amino acid sequence selected from the group consisting of SEQ ID NO:9, SEQ ID NO:10, and SEQ ID NO:13.

19. The method of claim 17 wherein the nucleic acid encoding the first production enhancer protein is operably linked to a constitutive ubiquitous promoter.

20. The method of claim 19 wherein the constitutive promoter is selected from the group consisting of ubiquitin C promoter, CMV-IE promoter, and SV40 promoter.

21. The method of claim 18 wherein the first polynucleotide comprises the nucleic acid sequence of SEQ ID NO:18.

22. The method of claim 21 wherein the first polynucleotide comprises the nucleic acid sequence of SEQ ID NO:17.

23. The method of claim 17 further comprising prior to step a. the steps of:
aa. in any order,
   i. transfecting the cell with the first polynucleotide, and
   ii. transfecting the cell with the second polynucleotide; and
bb. clonally expanding the cell comprising the first polynucleotide and the second polynucleotide.

24. The method of claim 17 wherein the cell further comprises a third polynucleotide comprising a nucleic acid encoding a second production enhancer protein comprising an amino acid sequence that is at least 92% identical to SEQ ID NO:1, and allowing the cells at step (b) to secrete the multi-subunit protein into the media at a rate ≥37 pg/cell/day.

25. The method of claim 24 wherein the second production enhancer protein comprises an amino acid sequence selected from the group consisting of SEQ ID NO:1, SEQ ID NO:2, SEQ ID NO:3, SEQ ID NO:4, SEQ ID NO:5, SEQ ID NO:6 and SEQ ID NO:8.

26. The method of claim 24 wherein the nucleic acid encoding the second production enhancer protein is operably linked to a constitutive promoter.

27. The method of claim 26 wherein the constitutive promoter is selected from the group consisting of ubiquitin C promoter, CMV-IE promoter, and SV40 promoter.

28. The method of claim 25 wherein the third polynucleotide comprises the nucleic acid sequence of SEQ ID NO:16.

29. The method of claim 28 wherein the third polynucleotide comprises the nucleic acid sequence of SEQ ID NO:14 or 15.

30. The method of claim 24 further comprising prior to step a. the steps of:
aa. in any order,
   i. transfecting the cell with the first polynucleotide,
   ii. transfecting the cell with the second polynucleotide, and
   iii. transfecting the cell with the third polynucleotide; and
bb. clonally expanding the cell comprising the first polynucleotide, the second polynucleotide, and the third polynucleotide.

31. The method of claim 17 wherein the multi-subunit protein accumulates in the media to a titer of ≥2.1 g/L, ≥3.8 g/L, or ≥4.2 g/L.

32. The method of claim 24 wherein the multi-subunit protein accumulates in the media to a titer of ≥5.3 g/L, ≥5.9 g/L, or ≥8.1 g/L.

33. The method of claim 17 wherein the multi-subunit protein is an antibody.

34. The method of claim 33 wherein the antibody further comprises a polypeptide with an amino acid sequence of SEQ ID NO:46.

35. The method of claim 34 wherein the antibody is an anti-GDF8 antibody, an anti-Ang2 antibody, or an anti-AngPtl4 antibody.

* * * * *